US010802030B2

(12) United States Patent
Tarca et al.

(10) Patent No.: US 10,802,030 B2
(45) Date of Patent: Oct. 13, 2020

(54) SYSTEMS AND METHODS TO PREDICT RISK FOR PRETERM LABOR AND/OR PRETERM BIRTH

(71) Applicants: WAYNE STATE UNIVERSITY, Detroit, MI (US); The United States of America as Represented by the Secretary, Department of Health and Human Service, Bethesda, MD (US)

(72) Inventors: Adi L. Tarca, Canton, MI (US); Offer Erez, Detroit, MI (US); Tinnakorn Chaiworapongsa, Grosse Pointe Park, MI (US); Sonia S. Hassan, Novi, MI (US); Roberto Romero, Grosse Pointe, MI (US)

(73) Assignees: Wayne State University, Detroit, MI (US); The United States of America as Represented by the Secretary, Department of Health and Human Service, Bethesda, MD (US)

( * ) Notice: Subject to any disclaimer, the term of this patent is extended or adjusted under 35 U.S.C. 154(b) by 0 days.

(21) Appl. No.: 15/958,959

(22) Filed: Apr. 20, 2018

(65) Prior Publication Data

US 2018/0306803 A1 Oct. 25, 2018

Related U.S. Application Data

(60) Provisional application No. 62/488,653, filed on Apr. 21, 2017.

(51) Int. Cl.
*G01N 33/53* (2006.01)
*G01N 33/68* (2006.01)

(52) U.S. Cl.
CPC ..... *G01N 33/689* (2013.01); *C12Q 2600/158* (2013.01); *G01N 2333/705* (2013.01); *G01N 2800/368* (2013.01); *G01N 2800/60* (2013.01)

(58) Field of Classification Search
None
See application file for complete search history.

(56) References Cited

U.S. PATENT DOCUMENTS

2011/0144076 A1* 6/2011 Williams ............. C12Q 1/6883
514/177

OTHER PUBLICATIONS

Van Der Vekiens et al., Human and equine cardiovascular endocrinology: beware to compare, Cardiovascular Endocrinology 2013, vol. 2, No. 4, pp. 67-76 (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Chaiworapongsa, et al., "The prediction of fetal death with a simple maternal blood test at 24-28 weeks: a role for angiogenic index-1 (PIGF/sVEGFR-1 ratio)" Am. J. Obstet. Gynecol., vol. 217, No. 6, 2017, pp. 682.e1-682.e13.
Jelliffe-Pawlowski, et al., "Association of Early Preterm Birth with Abnormal Levels of Routinely Collected First and Second Trimester Biomarkers," Am. J. Obstet. Gynecol., vol. 208, No. 6, pp. 1-21, 2013.
Kallioniemi, et al., "Early pregnancy vaginal fluid phosphorylated insulin-like growth factor binding protein-1 predicts preterm delivery," Prenat. Diagn., vol. 33, No. 4, 2013, pp. 378-383.
Lannaman, et al., "Fetal death: an extreme manifestation of maternal anti-fetal rejection," J. Perinat. Med., vol. 45, No. 7, 2017, pp. 851-868.
Stout, et al., "First trimester serum analytes, maternal characteristics and ultrasound markers to predict pregnancies at risk for preterm birth," Placenta, vol. 34, No. 1, 2013, pp. 14-19.

* cited by examiner

*Primary Examiner* — Gary Counts
(74) *Attorney, Agent, or Firm* — C. Rachal Winger; Tanya M. Harding

(57) ABSTRACT

Provided are systems and methods to identify subjects at risk for preterm labor and/or preterm birth. The systems and methods utilize biomarkers. Also provided are systems and methods for decreasing the risk of preterm labor by administering a treatment following a positive risk identification.

2 Claims, 22 Drawing Sheets

Specification includes a Sequence Listing.

Sensitivity=56%
Specificity=81%
LR (+)=2.9

Bootstrap estimates:
Sensitivity=39%
Specificity=80%
LR (+)=1.96
Freq. of proteins in best model out of 200 bootstrap trials:
CAMK2B (56%)
CAMK2D (30%)
CAMK2A (19%)
Angiostatin (16%)
BMP-1 (14%)

Sensitivity=67%
Specificity=78%
LR (+)=3.0

Bootstrap estimates:
Sensitivity=28%
Specificity=80%
LR (+)=1.4
Freq. of proteins in best model
out of 200 bootstrap trials:
BMP-1 (19%)
CAMK2B (16%)
CAMK2A (13%)
Angiostatin (12%)
Esterase D (12%)
PDGF Rb (10%)

FIG. 3

|  | PTL (n=41) | Normal (n=77) | p-value |
|---|---|---|---|
| Age | 24 (21-27) | 24 (21-28) | 0.49 |
| Gestational age at delivery | 35 (33.1-36.1) | 39.3 (39-40.1) | 0 |
| Race | | | |
| Black | 38 (92.68%) | 73 (94.81%) | 0.71 |
| Hispanic | 1 (2.44%) | 0 (0%) | |
| Other | 1 (2.44%) | 2 (2.6%) | |
| White | 1 (2.44%) | 2 (2.6%) | |
| Smoking | 8 (19.51%) | 14 (18.42%) | 1 |
| Prior Preterm Births | 25 (60.98%) | 8 (10.39%) | 0 |
| Nulliparity | 7 (17.07%) | 20 (25.97%) | 0.36 |
| Abruption | 0 | 0 | 1 |
| Chronic Hypertension | 8 (19.51%) | 0 (0%) | 0.001 |

FIG. 3 (cont'd)

| PTL Placental lesions | Amniotic Fluid Infection | 10 (24.4%) | |
|---|---|---|---|
| | Chronic Chorioamnionitis or Villitis of Unknown Etiology | 13 (31.7%) | |
| | Maternal Vascular Underperfusion | 8 (19.5%) | |
| | No Lesions | 10 (24.4%) | |

FIG. 7

| SYMBOL | Name | Fold change | p-value | q-value |
|---|---|---|---|---|
| CAMK2B | Calcium/calmodulin-dependent protein kinase type II subunit beta | -1.4 | 0.0000 | 0.004 |
| CAMK2D | Calcium/calmodulin-dependent protein kinase type II subunit delta | -1.4 | 0.0000 | 0.007 |
| Integrin a1b1 | Integrin alpha-I: beta-1 complex | -1.3 | 0.0001 | 0.022 |
| CAMK2A | Calcium/calmodulin-dependent protein kinase type II subunit alpha | -1.2 | 0.0002 | 0.051 |
| BMP-1 | Bone morphogenetic protein 1 | 1.1 | 0.0008 | 0.134 |
| SHC1 | SHC-transforming protein 1 | -1.2 | 0.0009 | 0.134 |
| Moesin | Moesin | -1.2 | 0.0011 | 0.134 |
| FER | Tyrosine-protein kinase Fer | -1.3 | 0.0013 | 0.134 |
| PDPK1 | 3-phosphoinositide-dependent protein kinase 1 | -1.2 | 0.0013 | 0.134 | q<0.25; fold change> 1.1

FIG. 8

| Name | N | Proteins | OR | P | q |
|---|---|---|---|---|---|
| synaptic transmission | 4 | CAMK2B; CAMK2D; CAMK2A; PDPK1 | 53.7 | 0.000 | 0.000 |
| G1/S transition of mitotic cell cycle | 4 | CAMK2B; CAMK2D; Integrin a1b1; CAMK2A | 41.1 | 0.000 | 0.000 |
| protein autophosphorylation | 5 | CAMK2B; CAMK2D; CAMK2A; PDPK1; FER | 23.8 | 0.000 | 0.000 |
| calcium ion transport | 3 | CAMK2B; CAMK2D; CAMK2A | 54.6 | 0.000 | 0.000 |
| protein phosphorylation | 5 | CAMK2B; CAMK2D; CAMK2A; PDPK1; FER | 16.4 | 0.000 | 0.000 |
| interferon-gamma-mediated signaling pathway | 3 | CAMK2B; CAMK2D; CAMK2A | 36.6 | 0.000 | 0.001 |
| cytokine-mediated signaling pathway | 4 | CAMK2B; CAMK2D; CAMK2A; FER | 12.4 | 0.002 | 0.002 |
| leukocyte migration | 3 | Integrin a1b1; SHC1; Moesin | 13.2 | 0.004 | 0.005 |
| Fc-epsilon receptor signaling pathway | 3 | SHC1; PDPK1; FER | 8.2 | 0.013 | 0.016 |
| blood coagulation | 3 | Integrin a1b1; SHC1; PDPK1 | 4.3 | 0.061 | 0.067 |
| positive regulation of cell proliferation | 3 | Integrin a1b1; SHC1; FER | 3.5 | 0.097 | 0.097 |

FIG. 9

| SYMBOL | Name | Fold Change | p-value | q-value |
|---|---|---|---|---|
| TBP | TATA-box-binding protein | 1.275 | 0.000 | 0.06 |
| CAMK2B* | Calcium/calmodulin-dependent protein kinase type II subunit beta | -1.399 | 0.000 | 0.06 |
| CAMK2D* | Calcium/calmodulin-dependent protein kinase type II subunit delta | -1.384 | 0.000 | 0.08 |
| ENA-78 | C-X-C motif chemokine 5 | 1.124 | 0.000 | 0.09 |
| BMP-1* | Bone morphogenetic protein 1 | 1.168 | 0.001 | 0.09 |
| Integrin a1b1* | Integrin alpha-I: beta-1 complex | -1.368 | 0.001 | 0.17 |
| LRRT1 | Leucine-rich repeat transmembrane neuronal protein 1 | 1.259 | 0.001 | 0.17 |
| Neurotrophin-5 | Neurotrophin-4 | 1.162 | 0.002 | 0.17 |
| CAMK2A* | Calcium/calmodulin-dependent protein kinase type II subunit alpha | -1.198 | 0.002 | 0.17 |
| PDGF Rb | Platelet-derived growth factor receptor beta | -1.256 | 0.003 | 0.23 |
| FER* | Tyrosine-protein kinase Fer | -1.342 | 0.003 | 0.23 |

* Also differentially abundant with PTL<37

FIG. 11

>Homo sapiens CAMK2A isoform A (Uniprot Accession Q9UQM7-1)
MATITCTRFTEEYQLFEELGKGAFSVVRRCVKVLAGQEYAAKIINTKKLSARDHQKLEREARICR
LLKHPNIVRLHDSISEEGHHYLIFDLVTGGELFEDIVAREYYSEADASHCIQQILEAVLHCHQMGV
VHRDLKPENLLLASKLKGAAVKLADFGLAIEVEGEQQAWFGFAGTPGYLSPEVLRKDPYGKPV
DLWACGVILYILLVGYPPFWDEDQHRLYQQIKAGAYDFPSPEWDTVTPEAKDLINKMLTINPSK
RITAAEALKHPWISHRSTVASCMHRQETVDCLKKFNARRKLKGAILTTMLATRNFSGGKSGGN
KKSDGVKESSESTNTTIEDEDTKVRKQEIIKVTEQLIEAISNGDFESYTKMCDPGMTAFEPEALG
NLVEGLDFHRFYFENLWSRNSKPVHTTILNPHIHLMGDESACIAYIRITQYLDAGGIPRTAQSEE
TRVWHRRDGKWQIVHFHRSGAPSVLPH (SEQ ID NO: 1)

>Homo sapiens CAMK2B isoform 4 (Uniprot Accession Q13554-1)
MATTVTCTRFTDEYQLYEDIGKGAFSVVRRCVKLCTGHEYAAKIINTKKLSARDHQKLEREARIC
RLLKHSNIVRLHDSISEEGFHYLVFDLVTGGELFEDIVAREYYSEADASHCIQQILEAVLHCHQM
GVVHRDLKPENLLLASKCKGAAVKLADFGLAIEVQGDQQAWFGFAGTPGYLSPEVLRKEAYGK
PVDIWACGVILYILLVGYPPFWDEDQHKLYQQIKAGAYDFPSPEWDTVTPEAKNLINQMLTINPA
KRITAHEALKHPWVCQRSTVASMMHRQETVECLKKFNARRKLKGAILTTMLATRNFSVGRQTT
APATMSTAASGTTMGLVEQAKSLLNKKADGVKPQTNSTKNSAAATSPKGTLPPAALEPQTTVI
HNPVDGIKESSDSANTTIEDEDAKAPRVPDILSSVRRGSGAPEAEGPLCPSPAPFSPLPAPSP
RISDILNSVRRGSGTPEAEGPLSAGPPPCLSPALLGPLSSPSPRISDILNSVRRGSGTPEAEGPS
PVGPPPCPSPTIPGPLPTPSRKQEIIKTTEQLIEAVNNGDFEAYAKICDPGLTSFEPEALGNLVEG
MDFHRFYFENLLAKNSKPIHTTILNPHVHVIGEDAACIAYIRLTQYIDGQGRPRTSQSEETRVWH
RRDGKWQNVHFHCSGAPVAPLQ (SEQ ID NO: 2)

>Homo sapiens CAMK2D isoform Delta 2 (Uniprot Accession Q13557-1)
MASTTTCTRFTDEYQLFEELGKGAFSVVRRCMKIPTGQEYAAKIINTKKLSARDHQKLEREARIC
RLLKHPNIVRLHDSISEEGFHYLVFDLVTGGELFEDIVAREYYSEADASHCIQQILESVNHCHLN
GIVHRDLKPENLLLASKSKGAAVKLADFGLAIEVQGDQQAWFGFAGTPGYLSPEVLRKDPYGK
PVDMWACGVILYILLVGYPPFWDEDQHRLYQQIKAGAYDFPSPEWDTVTPEAKDLINKMLTINP
AKRITASEALKHPWICQRSTVASMMHRQETVDCLKKFNARRKLKGAILTTMLATRNFSAAKSLL
KKPDGVKESTESSNTTIEDEDVKARKQEIIKVTEQLIEAINNGDFEAYTKICDPGLTAFEPEALGN
LVEGMDFHRFYFENALSKSNKPIHTIILNPHVHLVGDDAACIAYIRLTQYMDGSGMPKTMQSEE
TRVWHRRDGKWQNVHFHRSGSPTVPIKPPCIPNGKENFSGGTSLWQNI (SEQ ID NO: 3)

FIG. 11 cont'd.

>Homo sapiens BMP1 isoform BMP1-3 (Uniprot Accession P13497-1)
MPGVARLPLLLGLLLLPRPGRPLDLADYTYDLAEEDDSEPLNYKDPCKAAAFLGDIALDEEDLR
AFQVQQAVDLRRHTARKSSIKAAVPGNTSTPSCQSTNGQPQRGACGRWRGRSRSRRAATSR
PERVWPDGVIPFVIGGNFTGSQRAVFRQAMRHWEKHTCVTFLERTDEDSYIVFTYRPCGCCS
YVGRRGGGPQAISIGKNCDKFGIVVHELGHVVGFWHEHTRPDRDRHVSIVRENIQPGQEYNFL
KMEPQEVESLGETYDFDSIMHYARNTFSRGIFLDTIVPKYEVNGVKPPIGQRTRLSKGDIAQAR
KLYKCPACGETLQDSTGNFSSPEYPNGYSAHMHCVWRISVTPGEKIILNFTSLDLYRSRLCWY
DYVEVRDGFWRKAPLRGRFCGSKLPEPIVSTDSRLWVEFRSSSNWVGKGFFAVYEAICGGDV
KKDYGHIQSPNYPDDYRPSKVCIWRIQVSEGFHVGLTFQSFEIERHDSCAYDYLEVRDGHSES
STLIGRYCGYEKPDDIKSTSSRLWLKFVSDGSINKAGFAVNFFKEVDECSRPNRGGCEQRCLN
TLGSYKCSCDPGYELAPDKRRCEAACGGFLTKLNGSITSPGWPKEYPPNKNCIWQLVAPTQY
RISLQFDFFETEGNDVCKYDFVEVRSGLTADSKLHGKFCGSEKPEVITSQYNNMRVEFKSDNT
VSKKGFKAHFFSDKDECSKDNGGCQQDCVNTFGSYECQCRSGFVLHDNKHDCKEAGCDHKV
TSTSGTITSPNWPDKYPSKKECTWAISSTPGHRVKLTFMEMDIESQPECAYDHLEVFDGRDAK
APVLGRFCGSKKPEPVLATGSRMFLRFYSDNSVQRKGFQASHATECGGQVRADVKTKDLYSH
AQFGDNNYPGGVDCEWVIVAEEGYGVELVFQTFEVEEETDCGYDYMELFDGYDSTAPRLGRY
CGSGPPEEVYSAGDSVLVKFHSDDTITKKGFHLRYTSTKFQDTLHSRK (SEQ ID NO: 4)

>Homo sapiens angiostatin (amino acids 79-466 of plasminogen, UniProt Accession P00747)
NRKSSIIRMRDVVLFEKKVYLSECKTGNGKNYRGTMSKTKNGITCQKWSSTSPHRPRFSPATH
PSEGLEENYCRNPDNDPQGPWCYTTDPEKRYDYCDILECEEECMHCSGENYDGKISKTMSGL
ECQAWDSQSPHAGYIPSKFPNKNLKKNYCRNPDRELRPWCFTTDPNKRWELCDIPRCTTPP
PSSGPTYQCLKGTGENYRGNVAVTVSGHTCQHWSAQTPHTHNRTPENFPCKNLDENYCRNP
DGKRAPWCHTTNSQVRWEYCKIPSCDSSPVSTEQLAPTAPPELTPVVQDCYHGDGQSYRGT
SSTTTGKKCQSWSSMTPHRHQKTPENYPNAGLTMNYCRNPDADKGPWCFTTDPSVRWEY
CNLKKCSGTEASVVAPPP (SEQ ID NO: 5)

>Homo sapiens integrin alpha-1 (UniProt Accession P56199)
MAPRPRARPGVAVACCWLLTVVLRCCVSFNVDVKNSMTFSGPVEDMFGYTVQQYENEEGKW
VLIGSPLVGQPKNRTGDVYKCPVGRGESLPCVKLDLPVNTSIPNVTEVKENMTFGSTLVTPN
GGFLACGPLYAYRCGHLHYTTGICSDVSPTFQVVNSIAPVQECSTQLDIVIVLDGSNSIYPWDSV
TAFLNDLLERMDIGPKQTQVGIVQYGENVTHEFNLNKYSSTEEVLVAAKKIVQRGGRQTMTALG
IDTARKEAFTEARGARRGVKKVMVIVTDGESHDNHRLKKVIQDCEDENIQRFSIAILGSYNRGNL
STEKFVEEIKSIASEPTEKHFFNVSDELALVTIVKTLGERIFALEATADQSAASFEMEMSQTGFSA
HYSQDWVMLGAVGAYDWNGTVVMQKASQIIIPRNTTFNVESTKKNEPLASYLGYTVNSATASS
GDVLYIAGQPRYNHTGQVIIYRMEDGNIKILQTLSGEQIGSYFGSILTTTDIDKDSNTDILLVGAPM
YMGTEKEEQGKVYVYALNQTRFEYQMSLEPIKQTCCSSRQHNSCTTENKNEPCGARFGTAIA
AVKDLNLDGFNDIVIGAPLEDDHGGAVYIYHGSGKTIRKEYAQRIPSGGDGKTLKFFGQSIHGE
MDLNGDGLTDVTIGGLGGAALFWSRDVAVVKVTMNFEPNKVNIQKKNCHMEGKETVCINATVC
FDVKLKSKEDTIYEADLQYRVTLDSLRQISRSFFSGTQERKVQRNITVRKSECTKHSFYMLDKH
DFQDSVRITLDFNLTDPENGPVLDDSLPNSVHEYIPFAKDCGNKEKCISDLSLHVATTEKDLLIV
RSQNDKFNVSLTVKNTKDSAYNTRTIVHYSPNLVFSGIEAIQKDSCESNHNITCKVGYPFLRRG
EMVTFKILFQFNTSYLMENVTIYLSATSDSEEPPETLSDNVVNISIPVKYEVGLQFYSSASEYHISI
AANETVPEVINSTEDIGNEINIFYLIRKSGSFPMPELKLSISFPNMTSNGYPVLYPTGLSSSENAN
CRPHIFEDPFSINSGKKMTTSTDHLKRGTILDCNTCKFATITCNLTSSDISQVNVSLILWKPTFIKS
YFSSLNLTIRGELRSENASLVLSSSNQKRELAIQISKDGLPGRVPLWVILLSAFAGLLLLMLLILAL
WKIGFFKRPLKKKMEK (SEQ ID NO: 6)

FIG. 11 cont'd.

>Homo sapiens integrin beta-1 isoform 1 (UniProt Accession P05556-1)
MNLQPIFWIGLISSVCCVFAQTDENRCLKANAKSCGECIQAGPNCGWCTNSTFLQEGMPTSAR
CDDLEALKKKGCPPDDIENPRGSKDIKKNKNVTNRSKGTAEKLKPEDITQIQPQQLVLRLRSGE
PQTFTLKFKRAEDYPIDLYYLMDLSYSMKDDLENVKSLGTDLMNEMRRITSDFRIGFGSFVEKT
VMPYISTTPAKLRNPCTSEQNCTSPFSYKNVLSLTNKGEVFNELVGKQRISGNLDSPEGGFDAI
MQVAVCGSLIGWRNVTRLLVFSTDAGFHFAGDGKLGGIVLPNDGQCHLENNMYTMSHYYDYP
SIAHLVQKLSENNIQTIFAVTEEFQPVYKELKNLIPKSAVGTLSANSSNVIQLIIDAYNSLSSEVILE
NGKLSEGVTISYKSYCKNGVNGTGENGRKCSNISIGDEVQFEISITSNKCPKKDSDSFKIRPLGF
TEEVEVILQYICECECQSEGIPESPKCHEGNGTFECGACRCNEGRVGRHCECSTDEVNSEDM
DAYCRKENSSEICSNNGECVCGQCVCRKRDNTNEIYSGKFCECDNFNCDRSNGLICGGNGVC
KCRVCECNPNYTGSACDCSLDTSTCEASNGQICNGRGICECGVCKCTDPKFQGQTCEMCQT
CLGVCAEHKECVQCRAFNKGEKKDTCTQECSYFNITKVESRDKLPQPVQPDPVSHCKEKDVD
DCWFYFTYSVNGNNEVMVHVVENPECPTGPDIIPIVAGVVAGIVLIGLALLLIWKLLMIIHDRREF
AKFEKEKMNAKWDTGENPIYKSAVTTVVNPKYEGK (SEQ ID NO: 7)

>Homo sapiens SHC1 isoform p66Shc (UniProt Accession P29353-1)
MDLLPPKPKYNPLRNESLSSLEEGASGSTPPEELPSPSASSLGPILPPLPGDDSPTTLCSFFPR
MSNLRLANPAGGRPGSKGEPGRAADDGEGIVGAAMPDSGPLPLLQDMNKLSGGGGRRTRVE
GGQLGGEEWTRHGSFVNKPTRGWLHPNDKVMGPGVSYLVRYMGCVEVLQSMRALDFNTRT
QVTREAISLVCEAVPGAKGATRRRKPCSRPLSSILGRSNLKFAGMPITLTVSTSSLNLMAADCK
QIIANHHMQSISFASGGDPDTAEYVAYVAKDPVNQRACHILECPEGLAQDVISTIGQAFELRFKQ
YLRNPPKLVTPHDRMAGFDGSAWDEEEEEPPDHQYYNDFPGKEPPLGGVVDMRLREGAAPG
AARPTAPNAQTPSHLGATLPVGQPVGGDPEVRKQMPPPPPCPGRELFDDPSYVNVQNLDKA
RQAVGGAGPPNPAINGSAPRDLFDMKPFEDALRVPPPPQSVSMAEQLRGEPWFHGKLSRRE
AEALLQLNGDFLVRESTTTPGQYVLTGLQSGQPKHLLLVDPEGVVRTKDHRFESVSHLISYHM
DNHLPIISAGSELCLQQPVERKL (SEQ ID NO: 8)

>Homo sapiens Moesin (MSN) (UniProt Accession P26038)
MPKTISVRVTTMDAELEFAIQPNTTGKQLFDQVVKTIGLREVWFFGLQYQDTKGFSTWLKLNKK
VTAQDVRKESPLLFKFRAKFYPEDVSEELIQDITQRLFFLQVKEGILNDDIYCPPETAVLLASYAV
QSKYGDFNKEVHKSGYLAGDKLLPQRVLEQHKLNKDQWEERIQVWHEEHRGMLREDAVLEYL
KIAQDLEMYGVNYFSIKNKKGSELWLGVDALGLNIYEQNDRLTPKIGFPWSEIRNISFNDKKFVIK
PIDKKAPDFVFYAPRLRINKRILALCMGNHELYMRRRKPDTIEVQQMKAQAREEKHQKQMERA
MLENEKKKREMAEKEKEKIEREKEELMERLKQIEEQTKKAQQELEEQTRRALELEQERKRAQS
EAEKLAKERQEAEEAKEALLQASRDQKKTQEQLALEMAELTARISQLEMARQKKESEAVEWQ
QKAQMVQEDLEKTRAELKTAMSTPHVAEPAENEQDEQDENGAEASADLRADAMAKDRSEEE
RTTEAEKNERVQKHLKALTSELANARDESKKTANDMIHAENMRLGRDKYKTLRQIRQGNTKQR
IDEFESM (SEQ ID NO: 9)

FIG. 11 cont'd.

>Homo sapiens FER isoform 1 (UniProt Accession P16591-1)
MGFGSDLKNSHEAVLKLQDWELRLLETVKKFMALRIKSDKEYASTLQNLCNQVDKESTVQMNY
VSNVSKSWLLMIQQTEQLSRIMKTHAEDLNSGPLHRLTMMIKDKQQVKKSYIGVHQQIEAEMIK
VTKTELEKLKCSYRQLIKEMNSAKEKYKEALAKGKETEKAKERYDKATMKLHMLHNQYVLALK
GAQLHQNQYYDITLPLLLDSLQKMQEEMIKALKGIFDEYSQITSLVTEEIVNVHKEIQMSVEQIDP
STEYNNFIDVHRTTAAKEQEIEFDTSLLEENENLQANEIMWNNLTAESLQVMLKTLAEELMQTQ
QMLLNKEEAVLELEKRIEESSETCEKKSDIVLLLSQKQALEELKQSVQQLRCTEAKFSAQKELLE
QKVQENDGKEPPPVVNYEEDARSVTSMERKERLSKFESIRHSIAGIIRSPKSALGSSALSDMISI
SEKPLAEQDWYHGAIPRIEAQELLKKQGDFLVRESHGKPGEYVLSVYSDGQRRHFIIQYVDNM
YRFEGTGFSNIPQLIDHHYTTKQVITKKSGVVLLNPIPKDKKWILSHEDVILGELLGKGNFGEVYK
GTLKDKTSVAVKTCKEDLPQELKIKFLQEAKILKQYDHPNIVKLIGVCTQRQPVYIIMELVSGGDF
LTFLRRKKDELKLKQLVKFSLDAAAGMLYLESKNCIHRDLAARNCLVGENNVLKISDFGMSRQE
DGGVYSSSGLKQIPIKWTAPEALNYGRYSSESDVWSFGILLWETFSLGVCPYPGMTNQQARE
QVERGYRMSAPQHCPEDISKIMMKCWDYKPENRPKFSELQKELTIIKRKLT (SEQ ID NO: 10)

>Homo sapiens PDPK1 isoform 1 (UniProt Accession O15530-1)
MARTTSQLYDAVPIQSSVVLCSCPSPSMVRTQTESSTPPGIPGGSRQGPAMDGTAAEPRPGA
GSLQHAQPPPQPRKKRPEDFKFGKILGEGSFSTVVLARELATSREYAIKILEKRHIIKENKVPYVT
RERDVMSRLDHPFFVKLYFTFQDDEKLYFGLSYAKNGELLKYIRKIGSFDETCTRFYTAEIVSAL
EYLHGKGIIHRDLKPENILLNEDMHIQITDFGTAKVLSPESKQARANSFVGTAQYVSPELLTEKSA
CKSSDLWALGCIIYQLVAGLPPFRAGNEYLIFQKIIKLEYDFPEKFFPKARDLVEKLLVLDATKRL
GCEEMEGYGPLKAHPFFESVTWENLHQQTPPKLTAYLPAMSEDDEDCYGNYDNLLSQFGCM
QVSSSSSSHSLSASDTGLPQRSGSNIEQYIHDLDSNSFELDLQFSEDEKRLLLEKQAGGNPWH
QFVENNLILKMGPVDKRKGLFARRRQLLLTEGPHLYYVDPVNKVLKGEIPWSQELRPEAKNFKT
FFVHTPNRTYYLMDPSGNAHKWCRKIQEVWRQRYQSHPDAAVQ (SEQ ID NO: 11)

>Homo sapiens TBP isoform 1 (UniProt Accession P20226-1)
MDQNNSLPPYAQGLASPQGAMTPGIPIFSPMMPYGTGLTPQPIQNTNSLSILEEQQRQQQQQ
QQQQQQQQQQQQQQQQQQQQQQQQQQQAVAAAAVQQSTSQQATQGTSGQAP
QLFHSQTLTTAPLPGTTPLYPSPMTPMTPITPATPASESSGIVPQLQNIVSTVNLGCKLDLKTIAL
RARNAEYNPKRFAAVIMRIREPRTTALIFSSGKMVCTGAKSEEQSRLAARKYARVVQKLGFPAK
FLDFKIQNMVGSCDVKFPIRLEGLVLTHQQFSSYEPELFPGLIYRMIKPRIVLLIFVSGKVVLTGA
KVRAEIYEAFENIYPILKGFRKTT (SEQ ID NO: 12)

>Homo sapiens ENA-78 (CXCL5) (UniProt Accession P42830)
MSLLSSRAARVPGPSSSLCALLVLLLLLTQPGPIASAGPAAAVLRELRCVCLQTTQGVHPKMIS
NLQVFAIGPQCSKVEVVASLKNGKEICLDPEAPFLKKVIQKILDGGNKEN (SEQ ID NO: 13)

>Homo sapiens neurotrophin-4 (NTF4; synonym is neurotrophin-5) (UniProt Accession P34130)
MLPLPSCSLPILLLFLLPSVPIESQPPPSTLPPFLAPEWDLLSPRVVLSRGAPAGPPLLFLLEAGA
FRESAGAPANRSRRGELAVCDAVSGWVTDRRTAVDLRGREVEVLGEVPAA
GGSPLRQYFFETRCKADNAEEGGPGAGGGGCRGVDRRHWVSECKAKQSYVRALTADAQGR
VGWRWIRIDTACVCTLLSRTGRA (SEQ ID NO: 14)

FIG. 11 cont'd.

>Homo sapiens PDGF Rb isoform 1 (UniProt Accession P09619-1)
MRLPGAMPALALKGELLLLSLLLLLEPQISQGLVVTPPGPELVLNVSSTFVLTCSGSAPVVWER
MSQEPPQEMAKAQDGTFSSVLTLTNLTGLDTGEYFCTHNDSRGLETDERKRLYIFVPDPTVGF
LPNDAEELFIFLTEITEITIPCRVTDPQLVVTLHEKKGDVALPVPYDHQRGFSGIFEDRSYICKTTI
GDREVDSDAYYVYRLQVSSINVSVNAVQTVVRQGENITLMCIVIGNEVVNFEWTYPRKESGRL
VEPVTDFLLDMPYHIRSILHIPSAELEDSGTYTCNVTESVNDHQDEKAINITVVESGYVRLLGEV
GTLQFAELHRSRTLQVVFEAYPPPTVLWFKDNRTLGDSSAGEIALSTRNVSETRYVSELTLVRV
KVAEAGHYTMRAFHEDAEVQLSFQLQINVPVRVLELSESHPDSGEQTVRCRGRGMPQPNIIWS
ACRDLKRCPRELPPTLLGNSSEEESQLETNVTYWEEEQEFEVVSTLRLQHVDRPLSVRCTLRN
AVGGQDTQEVIVVPHSLPFKVVVISAILALVVLTIISLIILIMLWQKKPRYEIRWKVIESVSSDGHEYIY
VDPMQLPYDSTWELPRDQLVLGRTLGSGAFGQVVEATAHGLSHSQATMKVAVKMLKSTARSS
EKQALMSELKIMSHLGPHLNVVNLLGACTKGGPIYIITEYCRYGDLVDYLHRNKHTFLQHHSDK
RRPPSAELYSNALPVGLPLPSHVSLTGESDGGYMDMSKDESVDYVPMLDMKGDVKYADIESS
NYMAPYDNYVPSAPERTCRATLINESPVLSYMDLVGFSYQVANGMEFLASKNCVHRDLAARN
VLICEGKLVKICDFGLARDIMRDSNYISKGSTFLPLKWMAPESIFNSLYTTLSDVWSFGILLWEIF
TLGGTPYPELPMNEQFYNAIKRGYRMAQPAHASDEIYEIMQKCWEEKFEIRPPFSQLVLLLERL
LGEGYKKKYQQVDEEFLRSDHPAILRSQARLPGFHGLRSPLDTSSVLYTAVQPNEGDNDYIIPL
PDPKPEVADEGPLEGSPSLASSTLNEVNTSSTISCDSPLEPQDEPEPEPQLELQVEPEPELEQL
PDSGCPAPRAEAEDSFL (SEQ ID NO: 15)

>Homo sapiens PlGF isoform 1 (UniProt Accession Q07326-1)
MKDNDIKRLLYTHLLCIFSIILSVFIPSLFLENFSILETHLTWLCICSGFVTAVNLVLYLVVKPNTSSK
RSSLSHKVTGFLKCCIYFLMSCFSFHVIFVLYGAPLIELALETFLFAVILSTFTTVPCLCLLGPNLK
AWLRVFSRNGVTSIWENSLQITTISSFVGAWLGALPIPLDWERPWQVWPISCTLGATFGYVAGL
VISPLWIYWNRKQLTYKNN (SEQ ID NO: 16)

>Homo sapiens LRRT1 (UniProt Accession Q86UE6)
MDFLLLGLCLYWLLRRPSGVVLCLLGACFQMLPAAPSGCPQLCRCEGRLLYCEALNLTEAPHN
LSGLLGLSLRYNSLSELRAGQFTGLMQLTWLYLDHNHICSVQGDAFQKLRRVKELTLSSNQITQ
LPNTTFRPMPNLRSVDLSYNKLQALAPDLFHGLRKLTTLHMRANAIQFVPVRIFQDCRSLKFLDI
GYNQLKSLARNSFAGLFKLTELHLEHNDLVKVNFAHFPRLISLHSLCLRRNKVAIVVSSLDWVV
NLEKMDLSGNEIEYMEPHVFETVPHLQSLQLDSNRLTYIEPRILNSWKSLTSITLAGNLWDCGR
NVCALASWLNNFQGRYDGNLQCASPEYAQGEDVLDAVYAFHLCEDGAEPTSGHLLSAVTNRS
DLGPPASSATTLADGGEGQHDGTFEPATVALPGGEHAENAVQIHKVVTGTMALIFSFLIVVLVL
YVSWKCFPASLRQLRQCFVTQRRKQKQKQTMHQMAAMSAQEYYVDYKPNHIEGALVIINEYG
SCTCHQQPARECEV (SEQ ID NO: 17)

>Homo sapiens esterase D (S-formylglutathione hydrolase) (UniProt Accession P10768)
MALKQISSNKCFGGLQKVFEHDSVELNCKMKFAVYLPPKAETGKCPALYWLSGLTCTEQNFIS
KSGYHQSASEHGLVVIAPDTSPRGCNIKGEDESWDFGTGAGFYVDATEDPWKTNYRMYSYVT
EELPQLINANFPVDPQRMSIFGHSMGGHGALICALKNPGKYKSVSAFAPICNPVLCPWGKKAFS
GYLGTDQSKWKAYDATHLVKSYPGSQLDILIDQGKDDQFLLDGQLLPDNFIAACTEKKIPVVFRL
QEGYDHSYYFIATFITDHIRHHAKYLNA (SEQ ID NO: 18)

FIG. 11 cont'd.

>Homo sapiens plasminogen (UniProt Accession P00747)
MEHKEVVLLLLLFLKSGQGEPLDDYVNTQGASLFSVTKKQLGAGSIEECAAKCEEDEEFTCRAF
QYHSKEQQCVIMAENRKSSIIIRMRDVVLFEKKVYLSECKTGNGKNYRGTMSKTKNGITCQKW
SSTSPHRPRFSPATHPSEGLEENYCRNPDNDPQGPWCYTTDPEKRYDYCDILECEEECMHCS
GENYDGKISKTMSGLECQAWDSQSPHAHGYIPSKFPNKLKKNYCRNPDRELRPWCFTTDPN
KRWELCDIPRCTTPPPSSGPTYQCLKGTGENYRGNVAVTVSGHTCQHWSAQTPHTHNRTPE
NFPCKNLDENYCRNPDGKRAPWCHTTNSQVRWEYCKIPSCDSSPVSTEQLAPTAPPELTPVV
QDCYHGDGQSYRGTSSTTTTGKKCQSWSSMTPHRHQKTPENYPNAGLTMNYCRNPDADKG
PWCFTTDPSVRWEYCNLKKCSGTEASVVAPPPVVLLPDVETPSEEDCMFGNGKGYRGKRATT
VTGTPCQDWAAQEPHRHSIFTPETNPRAGLEKNYCRNPDGDVGGPWCYTTNPRKLYDYCDV
PQCAAPSFDCGKPQVEPKKCPGRVVGGCVAHPHSWPWQVSLRTRFGMHFCGGTLISPEWVL
TAAHCLEKSPRPSSYKVILGAHQEVNLEPHVQEIEVSRLFLEPTRKDIALLKLSSPAVITDKVIPA
CLPSPNYVVADRTECFITGWGETQGTFGAGLLKEAQLPVIENKVCNRYEFLNGRVQSTELCAG
HLAGGTDSCQGDSGGPLVCFEKDKYILQGVTSWGLGCARPNKPGVYVRVSRFVTWIEGVMR
NN (SEQ ID NO: 19)

>Homo sapiens CAMK2A isoform A cds (nucleotides 216-1652 of NCBI Reference Sequence: NM_171825.2)
ATGGCCACCATCACCTGCACCCGCTTCACGGAAGAGTACCAGCTCTTCGAGGAATTGGGC
AAGGGAGCCTTCTCGGTGGTGCGAAGGTGTGTGAAGGTGCTGGCTGGCCAGGAGTATGC
TGCCAAGATCATCAACACAAAGAAGCTGTCAGCCAGAGACCATCAGAAGCTGGAGCGTGA
AGCCCGCATCTGCCGCCTGCTGAAGCACCCCAACATCGTCCGACTACATGACAGCATCTC
AGAGGAGGGACACCACTACCTGATCTTCGACCTGGTCACTGGTGGGGAACTGTTTGAAGA
TATCGTGGCCCGGGAGTATTACAGTGAGGCGGATGCCAGTCACTGTATCCAGCAGATCCT
GGAGGCTGTGCTGCACTGCCACCAGATGGGGGTGGTGCACCGGGACCTGAAGCCTGAGA
ATCTGTTGCTGGCCTCCAAGCTCAAGGGTGCCGCAGTGAAGCTGGCAGACTTTGGCCTGG
CCATAGAGGTGGAGGGGGAGCAGCAGGCATGGTTTGGGTTTGCAGGGACTCCTGGATAT
CTCTCCCCAGAAGTGCTGCGGAAGGACCCGTACGGGAAGCCTGTGGACCTGTGGGCTTG
TGGGGTCATCCTGTACATCCTGCTGGTTGGGTACCCCCGTTCTGGGATGAGGACCAGCA
CCGCCTGTACCAGCAGATCAAAGCCGGCGCCTATGATTTCCCATCGCCGGAATGGGACAC
TGTCACCCCGGAAGCCAAGGATCTGATCAATAAGATGCTGACCATTAACCCATCCAAACGC
ATCACAGCTGCCGAAGCCCTTAAGCACCCTGGATCTCGCACCGCTCCACCGTGGCATCC
TGCATGCACAGACAGGAGACCGTGGACTGCCTGAAGAAGTTCAATGCCAGGAGGAAACTG
AAGGGAGCCATTCTCACCACGATGCTGGCCACCAGGAACTTCTCCGGAGGGAAGAGTGG
GGGAAACAAGAAGAGCGATGGTGTGAAGGAATCCTCAGAGAGCACCAACACCACCATCGA
GGATGAAGACACCAAAGTGCGGAAACAGGAAATTATAAAAGTGACAGAGCAGCTGATTGAA
GCCATAAGCAATGGAGATTTTGAGTCCTACACGAAGATGTGCGACCCTGGCATGACAGCC
TTCGAACCTGAGGCCCTGGGGAACCTGGTTGAGGGCCTGGACTTCCATCGATTCTATTTTG
AAAACCTGTGGTCCCGGAACAGCAAGCCCGTGCACACCACCATCCTGAATCCCCACATCC
ACCTGATGGGCGACGAGTCAGCCTGCATCGCCTACATCCGCATCACGCAGTACCTGGACG
CTGGCGGCATCCCACGCACCGCCCAGTCGGAGGAGACCCGTGTCTGGCACCGCCGGGAT
GGCAAATGGCAGATCGTCCACTTCCACAGATCTGGGGCGCCCTCCGTCCTGCCCCACTGA
(SEQ ID NO: 20)

FIG. 11 cont'd.

>Homo sapiens CAMK2B isoform 4 cds (nucleotides 211-2211 of NCBI Reference Sequence: NM_001220.4)
ATGGCCACCACGGTGACCTGCACCCGCTTCACCGACGAGTACCAGCTCTACGAGGATATT
GGCAAGGGGGCTTTCTCTGTGGTCCGACGCTGTGTCAAGCTCTGCACCGGCCATGAGTAT
GCAGCCAAGATCATCAACACCAAGAAGCTGTCAGCCAGAGATCACCAGAAGCTGGAGAGA
GAGGCTCGGATCTGCCGCCTTCTGAAGCATTCCAACATCGTGCGTCTCCACGACAGCATC
TCCGAGGAGGGCTTCCACTACCTGGTCTTCGATCTGGTCACTGGTGGGGAGCTCTTTGAA
GACATTGTGGCGAGAGAGTACTACAGCGAGGCTGATGCCAGTCACTGTATCCAGCAGATC
CTGGAGGCCGTTCTCCATTGTCACCAAATGGGGGTCGTCCACAGAGACCTCAAGCCGGAG
AACCTGCTTCTGGCCAGCAAGTGCAAAGGGGCTGCAGTGAAGCTGGCAGACTTCGGCCTA
GCTATCGAGGTGCAGGGGGACCAGCAGGCATGGTTTGGTTTCGCTGGCACACCAGGCTA
CCTGTCCCCTGAGGTCCTTCGCAAAGAGGCGTATGGCAAGCCTGTGGACATCTGGGCATG
TGGGGTGATCCTGTACATCCTGCTCGTGGGCTACCCACCCTTCTGGGACGAGGACCAGCA
CAAGCTGTACCAGCAGATCAAGGCTGGTGCCTATGACTTCCCGTCCCCTGAGTGGGACAC
CGTCACTCCTGAAGCCAAAAACCTCATCAACCAGATGCTGACCATCAACCCTGCCAAGCGC
ATCACAGCCCATGAGGCCCTGAAGCACCCGTGGGTCTGCCAACGCTCCACGGTAGCATCC
ATGATGCACAGACAGGAGACTGTGGAGTGTCTGAAAAAGTTCAATGCCAGGAGAAAGCTC
AAGGGAGCCATCCTCACCACCATGCTGGCCACACGGAATTTCTCAGTGGGCAGACAGACC
ACCGCTCCGGCCACAATGTCCACCGCGGCCTCCGGCACCACCATGGGGCTGGTGGAACA
AGCCAAGAGTTTACTCAACAAGAAAGCAGATGGAGTCAAGCCCCAGACGAATAGCACCAA
AAACAGTGCAGCCGCCACCAGCCCCAAGGGACGCTTCCTCCTGCCGCCCTGGAGCCTC
AAACCACCGTCATCCATAACCCAGTGGACGGGATTAAGGAGTCTTCTGACAGTGCCAATAC
CACCATAGAGGATGAAGACGCTAAAGCCCCAGGGTCCCCGACATCCTGAGCTCAGTGAG
GAGGGGCTCGGGAGCCCAGAAGCCGAGGGGCCCCTGCCCTGCCCATCTCCGGCTCCC
TTTAGCCCCCTGCCAGCCCCATCCCCCAGGATCTCTGACATCCTGAACTCTGTGAGAAGG
GGTTCAGGAACCCCAGAAGCCGAGGGCCCCTCTCAGCGGGGCCCCGCCCTGCCTGTC
TCCGGCTCTCCTAGGCCCCTGTCCTCCCCGTCCCCAGGATCTCTGACATCCTGAACTC
TGTGAGGAGGGGCTCAGGGACCCCAGAAGCCGAGGGCCCCTCGCCAGTGGGGCCCCG
CCCTGCCCATCTCCGACTATCCCTGGCCCCTGCCCACCCCATCCCGGAAGCAGGAGATC
ATTAAGACCACGGAGCAGCTCATCGAGGCCGTCAACAACGGTGACTTTGAGGCCTACGCG
AAAATCTGTGACCCAGGGCTGACCTCGTTTGAGCCTGAAGCACTGGGCAACCTGGTTGAA
GGGATGGACTTCCACAGATTCTACTTCGAGAACCTGCTGGCCAAGAACAGCAAGCCGATC
CACACGACCATCCTGAACCCACACGTGCACGTCATTGGAGAGGATGCCGCCTGCATCGCT
TACATCCGGCTCACGCAGTACATTGACGGGCAGGGCCGGCCCCGCACCAGCCAGTCTGA
GGAGACCCGCGTGTGGCACCGCCGCGACGGCAAGTGGCAGAACGTGCACTTCCACTGCT
CGGGCGCGCCTGTGGCCCCGCTGCAGTGA (SEQ ID NO: 21)

FIG. 11 cont'd.

>Homo sapiens CAMK2D isoform Delta 2 cds (nucleotides 860-2359 of NCBI Reference Sequence: NM_ 001221.3)
ATGGCTTCGACCACAACCTGCACCAGGTTCACGGACGAGTATCAGCTTTTCGAGGAGCTT
GGAAAGGGGGCATTCTCAGTGGTGAGAAGATGTATGAAAATTCCTACTGGACAAGAATATG
CTGCCAAAATTATCAACACCAAAAAGCTTTCTGCTAGGGATCATCAGAAACTAGAAAGAGAA
GCTAGAATCTGCCGTCTTTTGAAGCACCCTAATATTGTGCGACTTCATGATAGCATATCAGA
AGAGGGCTTTCACTACTTGGTGTTTGATTTAGTTACTGGAGGTGAACTGTTTGAAGACATAG
TGGCAAGAGAATACTACAGTGAAGCTGATGCCAGTCATTGTATACAGCAGATTCTAGAAAG
TGTTAATCATTGTCACCTAAATGGCATAGTTCACAGGGACCTGAAGCCTGAGAATTTGCTTT
TAGCTAGCAAATCCAAGGGAGCAGCTGTGAAATTGGCAGACTTTGGCTTAGCCATAGAAGT
TCAAGGGGACCAGCAGGCGTGGTTTGGTTTTGCTGGCACACCTGGATATCTTTCTCCAGAA
GTTTTACGTAAAGATCCTTATGGAAAGCCAGTGGATATGTGGGCATGTGGTGTCATTCTCT
ATATTCTACTTGTGGGGTATCCACCCTTCTGGGATGAAGACCAACACAGACTCTATCAGCA
GATCAAGGCTGGAGCTTATGATTTTCCATCACCAGAATGGGACACGGTGACTCCTGAAGCC
AAAGACCTCATCAATAAAATGCTTACTATCAACCCTGCCAAACGCATCACAGCCTCAGAGG
CACTGAAGCACCCATGGATCTGTCAACGTTCTACTGTTGCTTCCATGATGCACAGACAGGA
GACTGTAGACTGCTTGAAGAAATTTAATGCTAGAAGAAAACTAAAGGGTGCCATCTTGACA
ACTATGCTGGCTACAAGGAATTTCTCAGCAGCCAAGAGTTTGTTGAAGAAACCAGATGGAG
TAAAGGAGTCAACTGAGAGTTCAAATACAACAATTGAGGATGAAGATGTGAAAGCACGAAA
GCAAGAGATTATCAAAGTCACTGAACAACTGATCGAAGCTATCAACAATGGGGACTTTGAA
GCCTACACAAAATCTGTGACCCAGGCCTTACTGCTTTTGAACCTGAAGCTTTGGGTAATTT
AGTGGAAGGGATGGATTTTCACCGATTCTACTTTGAAAATGCTTTGTCCAAAAGCAATAAAC
CAATCCACACTATTATTCTAAACCCTCATGTACATCTGGTAGGGGATGATGCCGCCTGCAT
AGCATATATTAGGCTCACACAGTACATGGATGGCAGTGGAATGCCAAAGACAATGCAGTCA
GAAGAGACTCGTGTGTGGCACCGCCGGGATGGAAAGTGGCAGAATGTTCATTTTCATCGC
TCGGGGTCACCAACAGTACCCATCAAGCCACCCTGTATTCCAAATGGGAAAGAAAACTTCT
CAGGAGGCACCTCTTTGTGGCAAAACATCTAA (SEQ ID NO: 22)

FIG. 11 cont'd.

>Homo sapiens BMP1 cds (nucleotides 267-3227 of NCBI Reference Sequence: NM_006129.4)
ATGCCCGGCGTGGCCCGCCTGCCGCTGCTGCTCGGGCTGCTGCTGCTCCCGCGTCCCGG
CCGGCCGCTGGACTTGGCCGACTACACCTATGACCTGGCGGAGGAGGACGACTCGGAGC
CCCTCAACTACAAAGACCCCTGCAAGGCGGCTGCCTTTCTTGGGGACATTGCCCTGGACG
AAGAGGACCTGAGGGCCTTCCAGGTACAGCAGGCTGTGGATCTCAGACGGCACACAGCT
CGTAAGTCCTCCATCAAAGCTGCAGTTCCAGGAAACACTTCTACCCCCAGCTGCCAGAGCA
CCAACGGGCAGCCTCAGAGGGGAGCCTGTGGGAGATGGAGAGGTAGATCCCGTAGCCGG
CGGGCGGCGACGTCCCGACCAGAGCGTGTGTGGCCCGATGGGGTCATCCCCTTTGTCAT
TGGGGGAAACTTCACTGGTAGCCAGAGGGCAGTCTTCCGGCAGGCCATGAGGCACTGGG
AGAAGCACACCTGTGTCACCTTCCTGGAGCGCACTGACGAGGACAGCTATATTGTGTTCAC
CTATCGACCTTGCGGGTGCTGCTCCTACGTGGGTCGCCGCGGCGGGGGCCCCAGGCCA
TCTCCATCGGCAAGAACTGTGACAAGTTCGGCATTGTGGTCCACGAGCTGGGCCACGTCG
TCGGCTTCTGGCACGAACACACTCGGCCAGACCGGGACCGCCACGTTTCCATCGTTCGTG
AGAACATCCAGCCAGGGCAGGAGTATAACTTCCTGAAGATGGAGCCTCAGGAGGTGGAGT
CCCTGGGGGAGACCTATGACTTCGACAGCATCATGCATTACGCTCGGAACACATTCTCCA
GGGGCATCTTCCTGGATACCATTGTCCCCAAGTATGAGGTGAACGGGGTGAAACCTCCCA
TTGGCCAAAGGACACGGCTCAGCAAGGGGACATTGCCCAAGCCCGCAAGCTTTACAAGT
GCCCAGCCTGTGGAGAGACCCTGCAAGACAGCACAGGCAACTTCTCCTCCCCTGAATACC
CCAATGGCTACTCTGCTCACATGCACTGCGTGTGGCGCATCTCTGTCACACCCGGGGAGA
AGATCATCCTGAACTTCACGTCCCTGGACCTGTACCGCAGCCGCCTGTGCTGGTACGACT
ATGTGGAGGTCCGAGATGGCTTCTGGAGGAAGGCGCCCCTCCGAGGCCGCTTCTGCGGG
TCCAAACTCCCTGAGCCTATCGTCTCCACTGACAGCCGCCTCTGGGTTGAATTCCGCAGCA
GCAGCAATTGGGTTGGAAAGGGCTTCTTTGCAGTCTACGAAGCCATCTGCGGGGGTGATG
TGAAAAAGGACTATGGCCACATTCAATCGCCCAACTACCCAGACGATTACCGGCCCAGCAA
AGTCTGCATCTGGCGGATCCAGGTGTCTGAGGGCTTCCACGTGGGCCTCACATTCCAGTC
CTTTGAGATTGAGCGCCACGACAGCTGTGCCTACGACTATCTGGAGGTGCGCGACGGGCA
CAGTGAGAGCAGCACCCTCATCGGGCGCTACTGTGGCTATGAGAAGCCTGATGACATCAA
GAGCACGTCCAGCCGCCTCTGGCTCAAGTTCGTCTCTGACGGGTCCATTAACAAAGCGGG
CTTTGCCGTCAACTTTTTCAAAGAGGTGGACGAGTGCTCTCGGCCCAACCGCGGGGGCTG
TGAGCAGCGGTGCCTCAACACCCTGGGCAGCTACAAGTGCAGCTGTGACCCCGGGTACG
AGCTGGCCCCAGACAAGCGCCGCTGTGAGGCTGCTTGTGGCGGATTCCTCACCAAGCTCA
ACGGCTCCATCACCAGCCCGGGCTGGCCCAAGGAGTACCCCCCAACAAGAACTGCATCT
GGCAGCTGGTGGCCCCCACCCAGTACCGCATCTCCCTGCAGTTTGACTTCTTTGAGACAG
AGGGCAATGATGTGTGCAAGTACGACTTCGTGGAGGTGCGCAGTGGACTCACAGCTGACT
CCAAGCTGCATGGCAAGTTCTGTGGTTCTGAGAAGCCCGAGGTCATCACCTCCCAGTACA
ACAACATGCGCGTGGAGTTCAAGTCCGACAACACCGTGTCCAAAAAGGGCTTCAAGGCCC
ACTTCTTCTCAGACAAGGACGAGTGCTCCAAGGATAACGGCGGCTGCCAGCAGGACTGCG
TCAACACGTTCGGCAGTTATGAGTGCCAATGCCGCAGTGGCTTCGTCCTCCATGACAACAA
GCACGACTGCAAAGAAGCCGGCTGTGACCACAAGGTGACATCCACCAGTGGTACCATCAC
CAGCCCCAACTGGCCTGACAAGTATCCAGCAAGAAGGAGTGCACGTGGGCCATCTCCAG
CACCCCCGGGCACCGGGTCAAGCTGACCTTCATGGAGATGGACATCGAGTCCCAGCCTG
AGTGTGCCTACGACCACCTAGAGGTGTTCGACGGGCGAGACGCCAAGGCCCCCGTCCTC
GGCCGCTTCTGTGGGAGCAAGAAGCCCGAGCCCGTCCTGGCCACAGGCAGCCGCATGTT
CCTGCGCTTCTACTCAGATAACTCGGTCCAGCGAAAGGGCTTCCAGGCCTCCCACGCCAC
AGAGTGCGGGGGCCAGGTACGGGCAGACGTGAAGACCAAGGACCTTTACTCCCACGCCC
AGTTTGGCGACAACAACTACCCTGGGGGTGTGGACTGTGAGTGGGTCATTGTGGCCGAGG
AAGGCTACGGCGTGGAGCTCGTGTTCCAGACCTTTGAGGTGGAGGAGGAGACCGACTGC
GGCTATGACTACATGGAGCTCTTCGACGGCTACGACAGCACAGCCCCCAGGCTGGGGCG

FIG. 11 cont'd.

CTACTGTGGCTCAGGGCCTCCTGAGGAGGTGTACTCGGCGGGAGATTCTGTCCTGGTGAA
GTTCCACTCGGATGACACCATCACCAAAAAAGGTTTCCACCTGCGATACACCAGCACCAAG
TTCCAGGACACACTCCACAGCAGGAAGTGA (SEQ ID NO: 23)

>Homo sapiens angiostatin cds (nucleotides 347-1511 of NCBI Reference Sequence: NM_000301.3)
AACAGGAAGTCCTCCATAATCATTAGGATGAGAGATGTAGTTTTATTTGAAAAGAAAGTGTA
TCTCTCAGAGTGCAAGACTGGGAATGGAAAGAACTACAGAGGGACGATGTCCAAAACAAA
AAATGGCATCACCTGTCAAAAATGGAGTTCCACTTCTCCCCACAGACCTAGATTCTCACCT
GCTACACACCCCTCAGAGGGACTGGAGGAGAACTACTGCAGGAATCCAGACAACGATCCG
CAGGGGCCCTGGTGCTATACTACTGATCCAGAAAAGAGATATGACTACTGCGACATTCTTG
AGTGTGAAGAGGAATGTATGCATTGCAGTGGAGAAAACTATGACGGCAAAATTTCCAAGAC
CATGTCTGGACTGGAATGCCAGGCCTGGGACTCTCAGAGCCCACACGCTCATGGATACAT
TCCTTCCAAATTTCCAAACAAGAACCTGAAGAAGAATTACTGTCGTAACCCCGATAGGGAG
CTGCGGCCTTGGTGTTTCACCACCGACCCCAACAAGCGCTGGGAACTTTGTGACATCCCC
CGCTGCACAACACCTCCACCATCTTCTGGTCCCACCTACCAGTGTCTGAAGGGAACAGGT
GAAAACTATCGCGGGAATGTGGCTGTTACCGTGTCCGGGCACACCTGTCAGCACTGGAGT
GCACAGACCCCTCACACACATAACAGGACACCAGAAAACTTCCCCTGCAAAAATTTGGATG
AAAACTACTGCCGCAATCCTGACGGAAAAAGGGCCCCATGGTGCCATACAACCAACAGCC
AAGTGCGGTGGGAGTACTGTAAGATACCGTCCTGTGACTCCTCCCAGTATCCACGGAAC
AATTGGCTCCCACAGCACCACCTGAGCTAACCCCTGTGGTCCAGGACTGCTACCATGGTG
ATGGACAGAGCTACCGAGGCACATCCTCCACCACCACCACAGGAAAGAAGTGTCAGTCTT
GGTCATCTATGACACCACACCGGCACCAGAAGACCCCAGAAAACTACCCAAATGCTGGCC
TGACAATGAACTACTGCAGGAATCCAGATGCCGATAAAGGCCCCTGGTGTTTTACCACAGA
CCCCAGCGTCAGGTGGGAGTACTGCAACCTGAAAAAATGCTCAGGAACAGAAGCGAGTGT
TGTAGCACCTCCGCCTG (SEQ ID NO: 24)

FIG. 11 cont'd.

>Homo sapiens plasminogen cds (nucleotides 113-2545 from NCBI Reference Sequence: NM_000301.3)
ATGGAACATAAGGAAGTGGTTCTTCTACTTCTTTTATTTCTGAAATCAGGTCAAGGAGAGCC
TCTGGATGACTATGTGAATACCCAGGGGGCTTCACTGTTCAGTGTCACTAAGAAGCAGCTG
GGAGCAGGAAGTATAGAAGAATGTGCAGCAAATGTGAGGAGGACGAAGAATTCACCTGC
AGGGCATTCCAATATCACAGTAAAGAGCAACAATGTGTGATAATGGCTGAAAACAGGAAGT
CCTCCATAATCATTAGGATGAGAGATGTAGTTTTATTTGAAAAGAAAGTGTATCTCTCAGAG
TGCAAGACTGGGAATGGAAAGAACTACAGAGGGACGATGTCCAAAACAAAAAATGGCATC
ACCTGTCAAAAATGGAGTTCCACTTCTCCCCACAGACCTAGATTCTCACCTGCTACACACC
CCTCAGAGGGACTGGAGGAGAACTACTGCAGGAATCCAGACAACGATCCGCAGGGGCCC
TGGTGCTATACTACTGATCCAGAAAAGAGATATGACTACTGCGACATTCTTGAGTGTGAAG
AGGAATGTATGCATTGCAGTGGAGAAAACTATGACGGCAAAATTTCCAAGACCATGTCTGG
ACTGGAATGCCAGGCCTGGGACTCTCAGAGCCCACACGCTCATGGATACATTCCTTCCAA
ATTTCCAAACAAGAACCTGAAGAAGAATTACTGTCGTAACCCCGATAGGGAGCTGCGGCCT
TGGTGTTTCACCACCGACCCCAACAAGCGCTGGGAACTTTGTGACATCCCCGCTGCACA
ACACCTCCACCATCTTCTGGTCCCACCTACCAGTGTCTGAAGGGAACAGGTGAAAACTATC
GCGGGAATGTGGCTGTTACCGTGTCCGGGCACACCTGTCAGCACTGGAGTGCACAGACC
CCTCACACACATAACAGGACACCAGAAAACTTCCCCTGCAAAAATTTGGATGAAAACTACT
GCCGCAATCCTGACGGAAAAAGGGCCCCATGGTGCCATACAACCAACAGCCAAGTGCGGT
GGGAGTACTGTAAGATACCGTCCTGTGACTCCTCCCAGTATCCACGGAACAATTGGCTCC
CACAGCACCACCTGAGCTAACCCCTGTGGTCCAGGACTGCTACCATGGTGATGGACAGAG
CTACCGAGGCACATCCTCCACCACCACCACAGGAAAGAAGTGTCAGTCTTGGTCATCTATG
ACACCACACCGGCACCAGAAGACCCCAGAAAACTACCCAAATGCTGGCCTGACAATGAAC
TACTGCAGGAATCCAGATGCCGATAAAGGCCCTGGTGTTTTACCACAGACCCCAGCGTC
AGGTGGGAGTACTGCAACCTGAAAAAATGCTCAGGAACAGAAGCGAGTGTTGTAGCACCT
CCGCCTGTTGTCCTGCTTCCAGATGTAGAGACTCCTTCCGAAGAAGACTGTATGTTTGGGA
ATGGGAAAGGATACCGAGGCAAGAGGGCGACCACTGTTACTGGGACGCCATGCCAGGAC
TGGGCTGCCCAGGAGCCCCATAGACACAGCATTTTCACTCCAGAGACAAATCCACGGGCG
GGTCTGGAAAAAATTACTGCCGTAACCCTGATGGTGATGTAGGTGGTCCCTGGTGCTACA
CGACAAATCCAAGAAAACTTTACGACTACTGTGATGTCCCTCAGTGTGCGGCCCCTTCATT
TGATTGTGGGAAGCCTCAAGTGGAGCCGAAGAAATGTCCTGGAAGGGTTGTAGGGGGGT
GTGTGGCCCACCCACATTCCTGGCCCTGGCAAGTCAGTCTTAGAACAAGGTTTGGAATGC
ACTTCTGTGGAGGCACCTTGATATCCCCAGAGTGGGTGTTGACTGCTGCCCACTGCTTGG
AGAAGTCCCCAAGGCCTTCATCCTACAAGGTCATCCTGGGTGCACACCAAGAAGTGAATCT
CGAACCGCATGTTCAGGAAATAGAAGTGTCTAGGCTGTTCTTGGAGCCCACACGAAAGAT
ATTGCCTTGCTAAAGCTAAGCAGTCCTGCCGTCATCACTGACAAAGTAATCCCAGCTTGTC
TGCCATCCCCAAATTATGTGGTCGCTGACCGGACCGAATGTTTCATCACTGGCTGGGGAG
AAACCCAAGGTACTTTTGGAGCTGGCCTTCTCAAGGAAGCCCAGCTCCCTGTGATTGAGAA
TAAAGTGTGCAATCGCTATGAGTTTCTGAATGGAAGAGTCCAATCCACCGAACTCTGTGCT
GGGCATTTGGCCGGAGGCACTGACAGTTGCCAGGGTGACAGTGGAGGTCCTCTGGTTTG
CTTCGAGAAGGACAAATACATTTTACAAGGAGTCACTTCTTGGGGTCTTGGCTGTGCACGC
CCCAATAAGCCTGGTGTCTATGTTCGTGTTTCAAGGTTTGTTACTTGGATTGAGGGAGTGA
TGAGAAATAATTAA (SEQ ID NO: 25)

SYSTEMS AND METHODS TO PREDICT RISK FOR PRETERM LABOR AND/OR PRETERM BIRTH

CROSS REFERENCE TO RELATED APPLICATIONS

This application claims priority to U.S. provisional application Ser. No. 62/488,653, filed Apr. 21, 2017, which is incorporated by reference herein in its entirety as if fully set forth herein.

STATEMENT REGARDING FEDERALLY SPONSORED RESEARCH OR DEVELOPMENT

This invention was made with government support under grant HSN275201300006C awarded by the National Institutes of Health. The government has certain rights in the invention.

FIELD OF THE DISCLOSURE

Provided are systems and methods to identify subjects at risk for preterm labor (PTL). The systems and methods utilize biomarkers. Also provided are systems and methods for decreasing the risk for PTL by administering a treatment following a positive risk identification.

STATEMENT REGARDING SEQUENCE LISTING

The Sequence Listing associated with this application is provided in text format in lieu of a paper copy, and is hereby incorporated by reference into the specification. The name of the text file containing the Sequence Listing is WSU 17-1434_ST25.txt. The text file is 109 KB, was created on Apr. 17, 2018, and is being submitted electronically via EFS-Web.

BACKGROUND OF THE DISCLOSURE

Preterm birth is the birth of an infant before 37 weeks of pregnancy. According to the United Nations World Health Organization (WHO), an estimated 15 million babies (more than 1 in 10) are born preterm every year. The occurrence of preterm births is also increasing due to factors such as labor treatments, induced fertility, infections, poor prenatal care, inappropriate maternal age, obesity, and smoking.

Preterm birth is the leading cause of neonatal morbidity and mortality, and is also a leading cause of long-term disabilities. Common disabilities faced by preterm individuals include breathing problems, feeding difficulties, cerebral palsy, developmental delay, vision problems, and hearing impairment. Additionally, babies born earlier than 7 months need specialized care in a hospital's neonatal intensive care unit (NICU), which adds cost.

Screening for risk of preterm birth can help identify patients who could benefit from medical interventions to reduce the likelihood of preterm birth. Short-term prediction methods that measure the extent to which premature labor has already begun can include assessing changes in the cervix and assessing fetal breathing movements. A health care professional may perform a pelvic exam for changes in the cervix and may also need to monitor contractions, usually several times over a period of a few hours. A transvaginal ultrasound exam may be done to measure the length of the cervix, as cervical length is inversely related to the rate of preterm delivery. Diagnostic tests to detect conditions that predispose to premature labor can include: cervical smears and measurement of vaginal pH for diagnosis of infection; amniotic fluid testing for amniotic fluid proteins; tests to determine the level of fetal fibronectin (fFN), a protein which has been linked to preterm birth, in vaginal discharge; and palpation for cervical assessment (bishop score) to subjectively assess cervical stage. Diagnostic tests to assess the condition of the fetus can also be done to determine whether delivery of the baby is necessary. Abdominal ultrasonography of the fetus can measure amniotic fluid volume and detect discordant fetal growth, and Doppler ultrasonography of the utero-placental and fetoplacental vessels can assess placental insufficiency and/or inadequate blood supply to the fetus. First trimester markers have been used to predict preterm birth, but only in combination with transabdominal ultrasound to examiner uterine arteries. Stout et al. (2013) Placenta 34(1): 14-19.

Yet diagnosis of preterm labor (PTL) can still be subjective and unreliable, and in particular, simple and more reliable tests are needed early in pregnancy. False positive diagnoses of PTL can often result in the use of unnecessary and potentially harmful medications including tocolytics (to inhibit uterine contractions), corticosteroids (to induce fetal lung maturation), and antibiotics (to treat local or systemic infection), and in costly and disruptive hospitalizations. On the flip side, false negative diagnoses of PTL can lead to missed opportunities to improve outcome for premature babies.

Thus, there is a need in the art for systems and methods that can identify women at risk of preterm delivery early in pregnancy (before 14 weeks of gestation), with better prediction performance without the requirement of multiple measurement procedures (e.g., such as the combination of protein assays and ultrasound).

SUMMARY OF THE DISCLOSURE

The present disclosure provides systems and methods to identify subjects at risk for preterm labor (PTL). The systems and methods utilize biomarkers. Also provided are systems and methods for decreasing the risk for PTL by administering a treatment following a positive risk identification.

In particular embodiments, the systems and methods predict PTL at <37 weeks gestation. In particular embodiments, the systems and methods predict PTL at <35 weeks gestation. In particular embodiments, the systems and methods predict PTL between 8 and 14 weeks gestation. In particular embodiments, biomarkers that can predict PTL at <37 weeks gestation include CAMK2A, CAMK2B, CAMK2D, BMP-1, and angiostatin. In particular embodiments, biomarkers that can predict PTL at <35 weeks gestation include CAMK2A, CAMK2B, and BMP-1.

BRIEF DESCRIPTION OF THE DRAWINGS

Many of the figures submitted herein are better understood in color. Applicants consider the color versions of the drawings as part of the original submission and reserve the right to present color images of the drawings in later proceedings.

Example 1 Figures.

Figure 1:
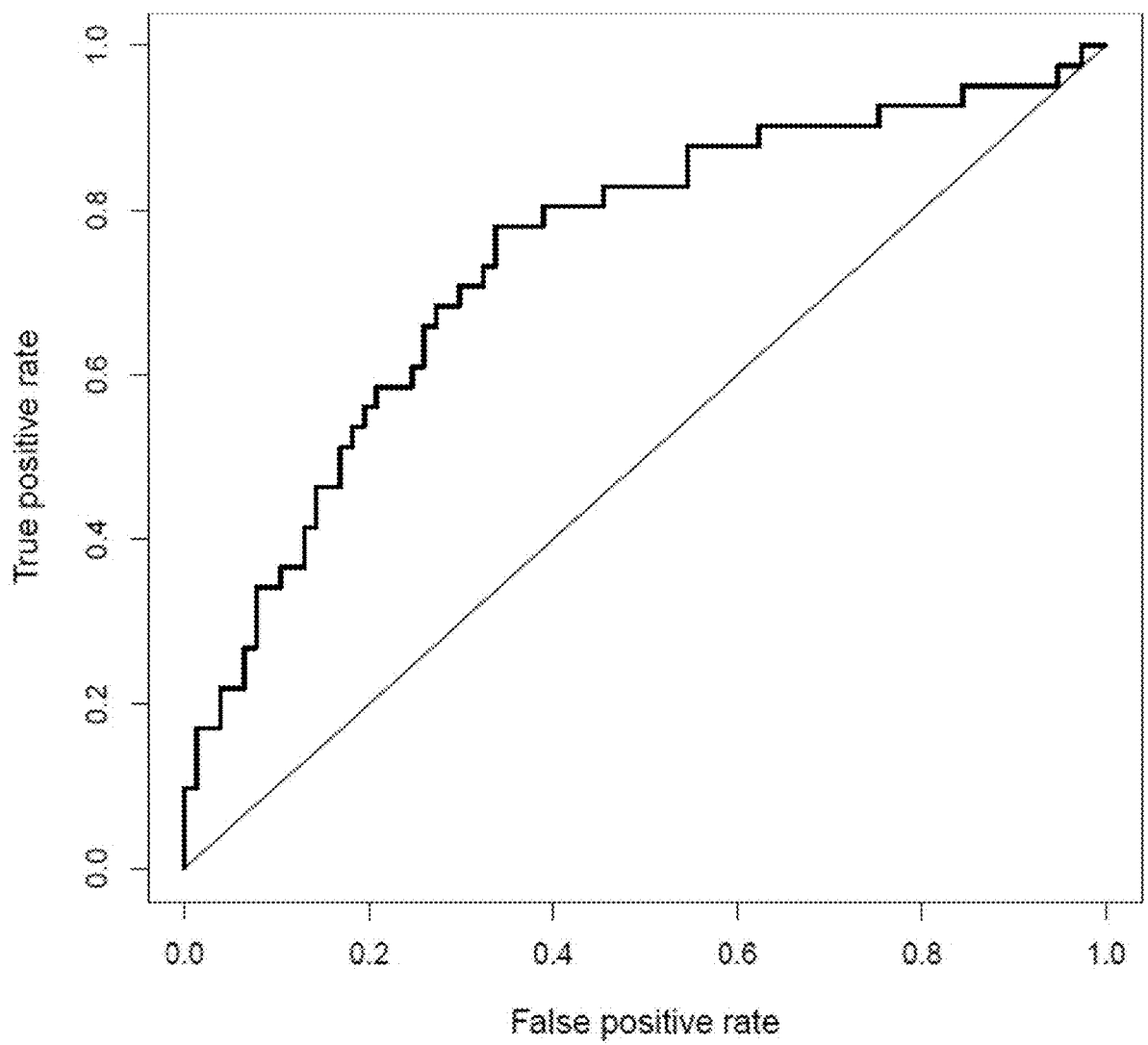
FIG. 1. Receiver operating characteristic (ROC) curve estimated by leave-one-out-cross-validation for CAMK2B predicting PTD<37 weeks (sensitivity of 56% at 80% specificity, AUC (area under the ROC curve)=0.74).

Example 2 Figures.

FIGS. 3-10. Additional supporting description and data, some of which overlaps with Example 1.

FIG. 11. Sequences supporting the disclosure.

DETAILED DESCRIPTION

Preterm birth is the birth of an infant before 37 weeks of pregnancy. According to the United Nations World Health Organization (WHO), an estimated 15 million babies (more than 1 in 10) are born preterm every year. The occurrence of preterm births is also increasing due to factors such as labor treatments, induced fertility, infections, poor prenatal care, inappropriate maternal age, obesity, and smoking.

Preterm birth is the leading cause of neonatal morbidity and mortality, and is also a leading cause of long-term disabilities. Common disabilities faced by preterm individuals include breathing problems, feeding difficulties, cerebral palsy, developmental delay, vision problems, and hearing impairment. Additionally, babies born earlier than 7 months need specialized care in a hospital's neonatal intensive care unit (NICU), which adds cost.

Screening for risk of preterm birth can help identify patients who could benefit from medical interventions to reduce the likelihood of preterm birth. Short-term prediction methods that measure the extent to which premature labor has already begun can include assessing changes in the cervix and assessing fetal breathing movements. A health care professional may perform a pelvic exam for changes in the cervix and may also need to monitor contractions, usually several times over a period of a few hours. A transvaginal ultrasound exam may be done to measure the length of the cervix, as cervical length is inversely related to the rate of preterm delivery. Diagnostic tests to detect conditions that predispose to premature labor can include: cervical smears and measurement of vaginal pH for diagnosis of infection; amniotic fluid testing for amniotic fluid proteins; tests to determine the level of fetal fibronectin (fFN), a protein which has been linked to preterm birth, in vaginal discharge; and palpation for cervical assessment (bishop score) to subjectively assess cervical stage. Diagnostic tests to assess the condition of the fetus can also be done to determine whether delivery of the baby is necessary. Abdominal ultrasonography of the fetus can measure amniotic fluid volume and detect discordant fetal growth, and Doppler ultrasonography of the utero-placental and fetoplacental vessels can assess placental insufficiency and/or inadequate blood supply to the fetus.

Methods have been developed to screen for risk of preterm birth using markers of placental dysfunction. For instance, PAPP-A (pregnancy associated plasma protein A), that is part of the first trimester screening, has an odds ratio of 2.09 (95% confidence interval out of 1.87 to 2.33 and a likelihood ratio positive of 1.84 (Morris et al. (2017) Prenat Diagn, 37: 253-265). In a different study, the incorporation of PAPP-A, PP-13 (placental protein 13), and uterine artery Doppler had a sensitivity for preterm delivery of 74% (at 95% specificity), 75% (at 90% specificity), and 77% (at 80% specificity). This model has a similar diagnostic performance when only preterm deliveries prior to 33 weeks of gestation were considered, yet it requires not only molecular markers but also Doppler velocimetry (Stout et al. (2013) Placenta 34: 14-19). In a cohort study, the combination of low PAPP-A in the first trimester and elevated alpha fetoprotein inhibin at the second trimester carries an odds ratio of 2.3 to 3.6 for early premature delivery (before 30 weeks of gestation). An abnormal result of PAPP-A at the first trimester carries an increased risk for a preterm delivery before 37 weeks of gestation (Jelliffe-Pawlowski et al. (2013) Am J Obstet Gynecol 208: 24; Pummara et al. (2016) 55: 72-75). Hughes et al. measured the maternal concentration of alkaline phosphatase during the first trimester and reported that it had a sensitivity of 57.14, a specificity of 85.71% for preterm birth before 37 weeks of gestation. The diagnostic performance of alkaline phosphatase did not reach statistical significance for preterm delivery before 34 weeks. Hughes, K, et al. (2017) Aust N Z J Obstet Gynaecol. The measurement of cystatin C at 11-14 weeks of gestation with a cut-off of 0.505 mg/L had a sensitivity of 91.9%, a specificity of 27.7%, and a positive likelihood ratio of 1.27 for detection in patients who would subsequently develop spontaneous preterm delivery and premature rupture of membranes (Gursoy et al. (2016) J Perinat Med 44: 295-299). The measurement of insulin-like growth factor binding protein-1 in vaginal or cervical samples of women in the first trimester has a cut-off of 10 mcg/L, an odds ratio of 8.6 for vaginal samples and 3.6 for cervical samples for predicting preterm delivery before 32 weeks of gestation, and an odds ratio of 3.0 for vaginal samples and 1.9 in cervical samples for the prediction of preterm delivery before 37 weeks of gestation (Kallioniemi et al. (2013) Prenat Diagn 33: 378-383).

Thus, diagnosis of preterm labor (PTL) can still be subjective and unreliable, and in particular, simple and more reliable tests are needed early in pregnancy. False positive diagnoses of PTL can often result in the use of unnecessary and potentially harmful medications including tocolytics (to inhibit uterine contractions), corticosteroids (to induce fetal lung maturation), and antibiotics (to treat local or systemic infection), and in costly and disruptive hospitalizations. On the flip side, false negative diagnoses of PTL can lead to missed opportunities to improve outcome for premature babies.

Therefore, there is a need in the art for systems and methods that can identify women at risk of preterm delivery early in pregnancy (before 14 weeks of gestation), with better prediction performance without the requirement of multiple measurement procedures (e.g., such as the combination of protein assays and ultrasound).

The present disclosure provides systems and methods to identify subjects at risk for PTL. The systems and methods utilize protein biomarkers. In particular embodiments, the systems and methods predict PTL at <37 weeks gestation. In particular embodiments, the systems and methods predict PTL at <35 weeks gestation. In particular embodiments, the systems and methods predict PTL between 8 and 14 weeks gestation. In particular embodiments, biomarkers that can predict PTL at <37 weeks gestation include CAMK2A, CAMK2B, CAMK2D, BMP-1, and angiostatin. In particular embodiments, biomarkers that can predict PTL at <35 weeks gestation include CAMK2A, CAMK2B, and BMP-1. Also provided are systems and methods for decreasing the risk for PTL by administering a treatment following a positive risk identification.

The following aspects of the disclosure are now described in additional detail: (i) Definitions supporting the disclosure; (ii) Subjects and samples; (iii) Binding ligands; (iv) Panel of binding ligands for biomarkers; (v) Reference levels and control populations; (vi) Methods; and (vii) Kits.

(i) Definitions supporting the disclosure. A "biomarker" described or disclosed herein include a biological product including proteins, nucleic acids, or a fragment of either thereof. In particular embodiments, one or more biomarkers of the present disclosure can be used in systems and methods of the present disclosure to identify a pregnant subject at risk of PTL, or to predict a positive or negative risk of PTL in a pregnant subject.

"Preterm labor" or "PTL" means the onset of labor symptoms at less than 37 weeks gestational age for humans. Labor symptoms include cramps or contractions, watery discharge from the vagina, backache, severe pelvic pressure, and blood from the vagina. PTL often leads to preterm birth. In particular embodiments, PTL means labor that begins on or after 22 weeks gestational age. These times may be adjusted for non-human subjects, as understood by one of ordinary skill in the art. In particular embodiments, PTL (e.g., for non-human subjects) includes labor occurring at less than 90% of term.

For humans, "preterm birth" means a birth <37 weeks completed gestational age and term birth means >37 completed weeks gestational age. These times may be adjusted for non-human subjects, as understood by one of ordinary skill in the art. In particular embodiments, preterm birth (e.g., for non-human subjects) includes birth less than 90% of term.

"Risk for preterm labor" or "risk for PTL" means an increase in the probability level that a subject will develop PTL as compared to a reference level obtained from a defined control population of subjects who experience full term labor. For example, the control population of subjects may include a single healthy pregnant subject at a comparative time of pregnancy, or a population of multiple healthy pregnant subjects at comparative time of pregnancy, who did not develop PTL. In addition, "risk for preterm labor" or "risk for PTL" can mean no change in the probability level that a subject will develop PTL as compared to a reference level obtained from a defined control population of subjects who experience PTL. For example, the control population of subjects may include a single healthy pregnant subject at a comparative time of pregnancy, or a population of multiple healthy pregnant subjects at comparative time of pregnancy, who did develop PTL. A "positive risk identification" means that a subject is at risk for PTL as determined by one of ordinary skill in the art practicing the teachings of the present disclosure. A "negative risk identification" means that a subject is not at risk for PTL as determined by one of ordinary skill in the art practicing the teachings of the present disclosure. In particular embodiments, a positive or negative risk for PTL can be determined by measuring expression of one or more biomarkers described herein and comparing the measurements to a reference level.

In particular embodiments, the risk for PTL can be monitored over time by analyzing subject samples and comparing levels of protein biomarkers to a control reference level. For example, more than one sample may be taken from the subject over time to analyze protein biomarkers levels. Further, control reference levels assembled from full term birth profiles taken at different time points throughout pregnancy can be used to compare to subject samples at equivalent gestational time periods. For example, subject samples may be taken at least once during each trimester and compared to equivalent time full term birth controls to monitor the risk for preterm birth throughout the pregnancy. Intra-subject controls and reference levels may also be used. In particular embodiments, the systems and methods predict PTL at <37 weeks gestation. In particular embodiments, the systems and methods predict PTL at <35 weeks gestation.

While the present disclosure is directed toward the identification of subjects at risk for PTL, the present disclosure can also be utilized to identify subjects who will most likely experience full term birth.

The discriminative ability of a diagnostic test can be quantified by measures of diagnostic accuracy, for example, sensitivity, specificity, likelihood ratio, and the area under the ROC curve (AUC). These measures can take into account four subgroups considering parameter values of interest, such as expression levels of one or more biomarkers disclosed herein: true positive (TP) subjects experiencing PTL have values above a cut-off value; false positive (FP) subjects not experiencing PTL have values above the cut-off; true negative (TN) subjects not experiencing PTL have values below the cut-off; and false negative (FN) subjects experiencing PTL have values below the cut-off. Sensitivity can be expressed in percentage and can define the proportion of true positive subjects experiencing PTL in a total group of subjects experiencing PTL (TP/TP+FN). In particular embodiments, sensitivity can be defined as the probability of getting a positive test result in subjects experiencing PTL. In particular embodiments, sensitivity relates to the potential of a test to recognize subjects experiencing PTL. Specificity is complementary to sensitivity. Specificity can define the proportion of subjects not experiencing PTL in a total group of subjects not experiencing PTL (TN/TN+FP). In particular embodiments, specificity can represent the probability of a negative test result in a subject not experiencing PTL. In particular embodiments, specificity describes the test ability to recognize subjects not experiencing PTL. A likelihood ratio (LR) can be used to determine whether a test result usefully changes the probability that PTL exists. In particular embodiments, the LR can indicate how many times more likely a given test result occurs in subjects experiencing PTL than in those not experiencing PTL. Likelihood ratio positive (LR+) can be defined as the ratio of the probability of a subject experiencing PTL testing positive to the probability of a subject not experiencing PTL testing positive. LR+ can be calculated by the following formula: LR+=sensitivity/(1−specificity). On the other hand, likelihood ratio negative (LR−) can be defined as the ratio of the probability of a subject experiencing PTL testing negative to the probability of a subject not experiencing PTL testing negative. LR− can be calculated by the following formula: LR−=(1−sensitivity)/specificity. An ROC graph can be plotted with 1-specificity on the x-axis and sensitivity on the y-axis. In particular embodiments, the shape of an ROC curve and the AUC can help estimate how high the discriminative power of a diagnostic test is. In particular embodiments, the closer the curve is located in the upper left-hand corner and the larger the AUC, the better the test is at discriminating between subjects experiencing PTL and subject not experiencing PTL.

(ii) Subjects and samples. When assessing a subject to identify the risk for PTL, a sample can be obtained from the subject. A subject can be any pregnant individual (most often a female, with certain limited exceptions). Subjects can be humans, veterinary animals (dogs, cats, reptiles, birds, etc.) livestock (horses, cattle, goats, pigs, chickens, etc.) and research animals (monkeys, rats, mice, fish, etc.).

A sample can be derived from any biological source, such as tissues, extracts, or cell cultures, including cells, cell lysates, and physiological fluids, including whole blood, plasma, serum, saliva, ocular lens fluid, cerebral spinal fluid, sputum, sweat, urine, milk, ascites fluid, synovial fluid, peritoneal fluid, and the like. In particular embodiments, samples are blood, urine and/or amniotic fluid. In particular embodiments, the sample is plasma and/or serum. In particular embodiments, the sample is urine.

In particular embodiments, samples can be obtained during pregnancy until the risk for PTL or delivery has passed (e.g., 37 weeks). For example, samples can be obtained during the first trimester of pregnancy, the second trimester of pregnancy or the third trimester of pregnancy. In humans, the first trimester of pregnancy refers to the 1st week to the 12th week of pregnancy. The second trimester of pregnancy refers to the 13th week to the 27th week of pregnancy. The third trimester of pregnancy refers to the 28th week of pregnancy until birth, which is the 40th week for a full-term pregnancy.

In particular embodiments, the sample may be obtained in the $14^{th}$ week of gestation or earlier. In particular embodiments, the sample may be obtained between the $8^{th}$ week and the $14^{th}$ week of gestation.

Particular embodiments include systems and methods for assessing a subject for risk for preterm labor. After obtaining a sample, the sample is processed to determine the level of one or more protein biomarkers in the sample. The protein biomarkers include one or more of: CAMK2A (calcium/calmodulin-dependent protein kinase type II subunit alpha); CAMK2B (calcium/calmodulin-dependent protein kinase type II subunit beta); CAMK2D (calcium/calmodulin-dependent protein kinase type II subunit delta); integrin a1b1 (integrin alpha-1:beta-1 complex); BMP-1 (bone morphogenetic protein 1); angiostatin; SHC1 (SHC transforming protein 1); Moesin; FER (tyrosine protein kinase Fer); PDPK1 (3-phosphoinositide-dependent protein kinase 1); TBP (TATA-box binding protein); ENA-78 (epithelial-derived neutrophil-activating peptide (ENA-78), also known as C-X-C motif chemokine ligand 5 (CXCL5)); neurotrophin-5 (also known as neurotrophin-4); PDGF Rb (platelet-derived growth factor receptor beta); PIGF (phosphatidylinositol-glycan biosynthesis class F protein); LRRT1 (leucine-rich repeat transmembrane neuronal protein 1); and/or esterase D. In particular embodiments, protein biomarkers of the present disclosure include SEQ ID NOs: 1-19. In particular embodiments, protein biomarkers of the present disclosure include isoforms of the protein biomarkers described or disclosed herein. In particular embodiments, one of ordinary skill in the art can obtain genes, mRNA, cDNA, coding sequences, and/or other nucleic acids encoding protein biomarkers of the present disclosure and measure expression levels of the genes mRNA, cDNA, coding sequences, and/or other nucleic acids to predict risk for PTL. In particular embodiments, biomarkers of the present disclosure include SEQ ID NOs: 20-25.

Samples can be collected and processed according to procedures known to those of ordinary skill in the art. In particular embodiments, the one or more protein biomarkers can be detected using any suitable method, such as immunoassay techniques including enzyme-linked immunosorbent assays (ELISAs), Enzyme Multiplied Immunoassay Technique, radioimmunoassays, enzyme immunoassays, fluorescence immunoassays, western blotting, immunoprecipitation and particle-based immunoassays. Exemplary methods for detection also include refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry (LC-MS), matrix-assisted laser desorption ionization-time of flight (MALDI-TOF) combined with mass spectrometry, ion spray spectroscopy combined with mass spectrometry, capillary electrophoresis, NMR and IR detection. Particular embodiments utilize LC-MS.

(iii) Binding ligands. A binding ligand to detect a biomarker can include a moiety that specifically binds to a selected biomarker. In particular embodiments, a binding ligand can include an aptamer, a ligand, a receptor, an allosteric regulator, an antibody, an affibody, or a fragment of any thereof. In particular embodiments, binding ligands can include antibodies, variable regions of antibodies, and/or binding fragments of an antibody, (e.g., Fv, Fab, Fab', F(ab')$_2$, Fc, and single chain Fv fragments (scFvs)).

In particular embodiments, a binding ligand binds to a biomarker. Bind means that the two relevant molecules associate with each other with a dissociation constant Kd of $10^{-8}$ M or less, in particular embodiments of from $10^{-5}$ M to $10^{-15}$ M, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-15}$ M.

In particular embodiments, a detection entity that binds to or otherwise associated with the binding ligand can be used for detection and/or quantitation of one or more biomarkers. In particular embodiments, the detection entity can include an enzyme, a colloidal metal, carbon, a biotin label, a visible label, a fluorescent label, latex beads impregnated with visual or fluorescent dyes, or a combination of these. In particular embodiments, the enzyme can include horseradish peroxidase, alkaline phosphatase, glucose oxidase, and β-galactosidase. In particular embodiments, the enzyme is used in conjunction with a colorimetric, fluorogenic or chemiluminescent substrate for visualization. In particular embodiments, the fluorescent label can include fluorescein (FITC), tetramethylrhodamine (TRITC), Rhodamine Red, Cyanine fluorophores, Texas Red, phycoerythrin (PE), R-phycoerythrin, allophycocyanin (APC), DyLight™ (Thermo Fisher Scientific, Waltham, Mass.), AlexaFluor™ (Thermo Fisher Scientific, Waltham, Mass.), or Atto dyes (Sigma-Aldrich, St. Louis, Mo.). Analysis with an appropriate instrument allows the identification of a given biomarker/binding ligand/detection entity complex and the magnitude of the signal from the detection entity.

Methods to detect nucleic acids encoding biomarkers described herein are known in the art. Such methods include methods based on hybridization analysis of nucleic acids, methods based on sequencing of nucleic acids, or polymerase chain reaction (PCR). The most commonly used methods known in the art for the quantification of mRNA expression in a sample include northern blotting and in situ hybridization; RNAse protection assays; and PCR-based methods, such as reverse transcription polymerase chain reaction (RT-PCR) or quantitative PCR (qPCR). Exemplary commercial products for performance of assays include MassARRAY-based method (Sequenom, Inc., San Diego, Calif.), differential display, amplified fragment length polymorphism (AFLP), and BeadArray™ technology (Illumina, San Diego, Calif.).

(iv) Panel of binding ligands for biomarkers. In particular embodiments, the present disclosure provides a panel for assessing subjects for the risk for PTL. In particular embodiments, the panel may include binding ligands that bind biomarkers listed in Table 1 and/or Table 2. The panel may include one or more binding ligands that bind at least one of the protein biomarkers disclosed herein. In particular embodiments, the panel may include one or more binding ligands that bind at least two of the protein biomarkers or at least three of the protein biomarkers disclosed herein. In particular embodiments, the panel includes one or more binding ligands that bind CAMK2A. In particular embodiments, the panel includes one or more binding ligands that bind CAMK2B. In particular embodiments, the panel includes one or more binding ligands that bind CAMK2D. In particular embodiments, the panel includes one or more binding ligands that bind integrin a1b1. In particular embodiments, the panel includes one or more binding ligands that bind BMP-1. In particular embodiments, the panel includes one or more binding ligands that bind angiostatin. In particular embodiments, the panel includes one or more binding ligands that bind SHC1. In particular embodiments, the panel includes one or more binding ligands that bind Moesin. In particular embodiments, the panel includes one or more binding ligands that bind FER. In particular embodiments, the panel includes one or more binding ligands that bind PDPK1. In particular embodiments, the panel includes one or more binding ligands that bind TBP. In particular embodiments, the panel includes one or more binding ligands that bind ENA-78. In particular embodiments, the panel includes one or more binding ligands that bind neurotrophin-5. In particular embodiments, the panel includes one or more binding ligands that bind PDGF Rb. In particular embodiments, the panel includes one or more binding ligands that bind PIGF. In particular embodiments, the panel includes one or more binding ligands that bind LRRT1. In particular embodiments, the panel includes one or more binding ligands that bind esterase D. In particular embodiments, the panel includes one or more binding ligands that bind each of CAMK2A, CAMK2B, and BMP-1. In particular embodiments, the panel includes one or more binding ligands that bind each of CAMK2A, CAMK2B, CAMK2D, BMP-1, and angiostatin.

Exemplary combinations of biomarkers disclosed herein that can be detected by binding ligands are listed here and in FIG. 8:

| | |
|---|---|
| CAMK2A, CAMK2B | CAMK2A, CAMK2B, CAM2KD |
| CAMK2A, CAMK2D | CAMK2A, CAMK2B, Integrin a1b1 |
| CAMK2A, Integrin a1b1 | CAMK2A, CAMK2B, BMP-1 |
| CAMK2A, BMP-1 | CAMK2A, CAMK2B, angiostatin |
| CAMK2A, angiostatin | CAMK2A, CAMK2B, SHC1 |
| CAMK2A, SHC1 | CAMK2A, CAMK2B, Moesin |
| CAMK2A, Moesin | CAMK2A, CAMK2B, FER |
| CAMK2A, FER | CAMK2A, CAMK2B, PDPK1 |
| CAMK2A, PDPK1 | CAMK2A, CAMK2B, TBP |
| CAMK2A, TBP | CAMK2A, CAMK2B, ENA-78 |
| CAMK2A, ENA-78 | CAMK2A, CAMK2B, Neurotrophin-5 |
| CAMK2A, Neurotrophin-5 | CAMK2A, CAMK2B, PDGF Rb |
| CAMK2A, PDGF Rb | CAMK2A, CAMK2B, PIGF |
| CAMK2A, PIGF | CAMK2A, CAMK2B, LRRT1 |
| CAMK2A, LRRT1 | CAMK2A, CAMK2B, Esterase D |
| CAMK2A, Esterase D | CAMK2A, CAMK2D, Integrin a1b1 |
| CAMK2B, CAMK2D | CAMK2A, CAMK2D, BMP-1 |
| CAMK2B, Integrin a1b1 | CAMK2A, CAMK2D, angiostatin |
| CAMK2B, BMP-1 | CAMK2A, CAMK2D, SHC1 |
| CAMK2B, angiostatin | CAMK2A, CAMK2D, Moesin |
| CAMK2B, SHC1 | CAMK2A, CAMK2D, FER |
| CAMK2B, Moesin | CAMK2A, CAMK2D, PDPK1 |
| CAMK2B, FER | CAMK2A, CAMK2D, TBP |
| CAMK2B, PDPK1 | CAMK2A, CAMK2D, ENA-78 |
| CAMK2B, TBP | CAMK2A, CAMK2D, Neurotrophin-5 |
| CAMK2B, ENA-78 | CAMK2A, CAMK2D, PDGF Rb |
| CAMK2B, Neurotrophin-5 | CAMK2A, CAMK2D, PIGF |
| CAMK2B, PDGF Rb | CAMK2A, CAMK2D, LRRT1 |
| CAMK2B, PIGF | CAMK2A, CAMK2D, Esterase D |
| CAMK2B, LRRT1 | CAMK2B, CAMK2D, Integrin a1b1 |
| CAMK2B, Esterase D | CAMK2B, CAMK2D, BMP-1 |
| CAMK2D, Integrin a1b1 | CAMK2B, CAMK2D, angiostatin |
| CAMK2D, BMP-1 | CAMK2B, CAMK2D, SHC1 |
| CAMK2D, angiostatin | CAMK2B, CAMK2D, Moesin |
| CAMK2D, SHC1 | CAMK2B, CAMK2D, FER |
| CAMK2D, Moesin | CAMK2B, CAMK2D, PDPK1 |
| CAMK2D, FER | CAMK2B, CAMK2D, TBP |
| CAMK2D, PDPK1 | CAMK2B, CAMK2D, ENA-78 |
| CAMK2D, TBP | CAMK2B, CAMK2D, Neurotrophin-5 |
| CAMK2D, ENA-78 | CAMK2B, CAMK2D, PDGF Rb |
| CAMK2D, Neurotrophin-5 | CAMK2B, CAMK2D, PIGF |
| CAMK2D, PDGF Rb | CAMK2B, CAMK2D, LRRT1 |
| CAMK2D, PIGF | CAMK2B, CAMK2D, Esterase D |
| CAMK2D, LRRT1 | Integrin a1b1, SHC1, CAM2KA |
| CAMK2D, Esterase D | Integrin a1b1, SHC1, CAM2KB |
| BMP-1, Integrin a1b1 | Integrin a1b1, SHC1, CAM2KD |
| BMP-1, angiostatin | Integrin a1b1, SHC1, Moesin |
| BMP-1, SHC1 | Integrin a1b1, SHC1, FER |
| BMP-1, Moesin | Integrin a1b1, SHC1, PDPK1 |
| BMP-1, FER | BMP-1, angiostatin, CAMK2A |
| BMP-1, PDPK1 | BMP-1, angiostatin, CAMK2B |
| BMP-1, TBP | BMP-1, angiostatin, CAMK2D |
| BMP-1, ENA-78 | BMP-1, angiostatin, Integrin a1b1 |
| BMP-1, Neurotrophin-5 | BMP-1, angiostatin, SHC1 |
| BMP-1, PDGF Rb | BMP-1, angiostatin, Moesin |
| BMP-1, PIGF | BMP-1, angiostatin, FER |
| BMP-1, LRRT1 | BMP-1, angiostatin, PDPK1 |
| BMP-1, Esterase D | CAM2KA, Integrin a1b1, BMP-1 |
| Angiostatin, SHC1 | CAM2KB, Integrin a1b1, BMP-1 |
| Angiostatin, Moesin | CAM2KD, Integrin a1b1, BMP-1 |
| Angiostatin, FER | CAM2KA, BMP-1, SHC1 |
| Angiostatin, PDPK1 | CAM2KB, BMP-1, SHC1 |
| Angiostatin, TBP | CAM2KD, BMP-1, SHC1 |
| Angiostatin, ENA-78 | SHC1, PDPK1, FER |
| Angiostatin, Neurotrophin-5 | CAMK2A, CAMK2B, BMP-1, angiostatin |
| Angiostatin, PDGF Rb | CAMK2A, CAMK2D, BMP-1, angiostatin |
| Angiostatin, PIGF | CAMK2B, CAMK2D, BMP-1, angiostatin |
| Angiostatin, LRRT1 | CAMK2A, CAMK2B, CAMK2D, angiostatin |
| Angiostatin, Esterase D | CAMK2A, CAMK2B, CAMK2D, BMP-1 |
| TBP, ENA-78, BMP-1 | CAMK2A, CAMK2B, CAMK2D, Integrin a1b1 |
| CAM2KA, ENA-78, BMP-1 | CAMK2A, CAMK2B, CAMK2D, SHC1 |
| CAM2KB, ENA-78, BMP-1 | CAMK2A, CAMK2B, CAMK2D, Moesin |
| CAM2KD, ENA-78, BMP-1 | CAMK2A, CAMK2B, CAMK2D, FER |
| Integrin a1b1, ENA-78, BMP-1 | CAMK2A, CAMK2B, CAMK2D, PDPK1 |
| Neurotrophin-5, ENA-78, BMP-1 | CAMK2A, CAMK2B, CAMK2D, PDPK1, FER |
| PDGF Rb, ENA-78, BMP-1 | CAMK2A, CAMK2B, CAMK2D, BMP-1, angiostatin |
| FER, ENA-78, BMP-1 | |

Binding ligands that can be used are commercially available and/or can be obtained or derived from sequences disclosed herein and/or accessed from publicly available databases.

To be diagnostic of a risk for PTL, at least one protein biomarker disclosed herein is present in a sample obtained from a subject. In particular embodiments, presence of at least one protein biomarker in the sample is sufficient to identify a subject as at risk for PTL. In particular embodiments, at least one protein biomarker must be present at a level that represents a statistically-significant increase over a control reference level from a population that did not experience PTL. In particular embodiments, at least one protein biomarker must be present at a level that represents a statistically-significant decrease over a control reference level from a population that did not experience PTL.

In particular embodiments, an increase in expression of a biomarker over a reference level of 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200% or more can identify a subject as at risk for preterm labor.

In particular embodiments, a decrease in expression of a biomarker over a reference level of 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% can identify a subject as at risk for preterm labor.

In particular embodiments, at least one protein biomarker must be present at a level that represents lack of a statistically significantly difference from a control reference level from a population that did experience PTL. A measure is not statistically significantly different if the difference is within a level that would be expected to occur based on chance alone.

In particular embodiments, the systems and methods assess the risk for PTL with a sensitivity of 40% or greater, 45% or greater, 50% or greater, 55% or greater, 58% or greater, 60% or greater, 65% or greater, 70% or greater, 75% or greater, 80% or greater, 85% or greater, 87.5%% or greater, 90% or greater, or 95% or greater, 99% or greater, and/or 100%.

In particular embodiments, the systems and methods assess the risk for PTL with a specificity of 40% or greater, 45% or greater, 50% or greater, 55% or greater, 58% or greater, 60% or greater, 65% or greater, 70% or greater, 75% or greater, 80% or greater, 85% or greater, 87.5%% or greater, 90% or greater, or 95% or greater, 99% or greater, and/or 100%.

In particular embodiments, the systems and methods assess the risk for PTL with an AUC of between 0.60 and 1.0. In particular embodiments, the systems and methods assess the risk for PTL with an AUC 0.60 or greater, 0.70 or greater, 0.80 or greater, or 0.90 or greater, or 1.0.

(v) Reference levels and control populations. In particular embodiments, obtained values for parameters associated with identifying subjects at risk for PTL described herein can be compared to a reference level derived from a control population. Parameters associated with risk for PTL can include expression of biomarkers described herein. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual datapoints; e.g., mean, median, median of the mean, etc. Alternatively, a reference level or dataset to create a reference level can be obtained from a service provider such as a laboratory, or from a database or a server on which the dataset has been stored. A reference level from a dataset can be derived from previous measures derived from a control population.

A "control population" is any grouping of subjects or samples of like specified characteristics. The grouping could be according to, for example, clinical parameters, clinical assessments, time of pregnancy, medical history, etc. In particular embodiments, the grouping is based on age range of subjects (e.g., 24-35 years) and gestational age at sampling. In particular embodiments, a normal control population includes individuals that are age-matched to a test subject and at 14 weeks gestation.

In particular embodiments, a control population can include a population of subjects who experience full term birth. In particular embodiments, a control population can include a population of subjects who experience birth at 37 weeks or later, at 38 weeks or later, at 39 weeks or later, or at 40 weeks or later. In particular embodiments, a control population can include a population of subjects who experience birth at 40 weeks.

In particular embodiments, a control population can include a population of subjects who experience PTL. In particular embodiments, a control population can include a population of subjects who experience birth at earlier than 37 weeks, earlier than 36 weeks, earlier than 35 weeks, earlier than 34 weeks, earlier than 33 weeks, earlier than 32 weeks, earlier than 31 weeks, earlier than 30 weeks, or earlier.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered significant (not random chance) at a p-value less than or equal to 0.05. In particular embodiments, a sample value is "comparable to" a reference level derived from a normal control population if the sample value and the reference level are not statistically significantly different.

In particular embodiments, values obtained about expression of biomarkers disclosed or described herein and/or other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained value with a reference level, a linear algorithm, a quadratic algorithm, a decision tree algorithm, or a voting algorithm. The analytic process may set a threshold for determining the probability that a sample belongs to a given class. The probability preferably is at least at least 60%, at least 70%, at least 80%, at least 90%, at least 95% or higher.

In particular embodiments, when more than one gene or protein disclosed or described herein is assayed, expression values of the detected genes or proteins can be calculated into a score. Each expression value can be weighted evenly within an algorithm generating a score, or the expression values for particular genes or proteins disclosed or described herein can be weighted more heavily in reaching the score. For example, genes or proteins disclosed or described herein with higher sensitivity and/or specificity scores could be weighted more heavily than genes or proteins disclosed or described herein with lower sensitivity and/or specificity scores. In particular embodiments, expression values of genes or proteins for diagnosing PTL may be weighted as follows (from highest weight to lowest weight): CAM2 KB;

CAM2KA; BMP-1; CAM2KD; angiostatin; integrin alb1; TBP; ENA-78; SHC1; Moesin; FER; PDPK1; neurotrophin-5; esterase D; PDGF Rb; LRRT1. In particular embodiments, expression values of genes or proteins for diagnosing PTL<37 weeks of gestation may be weighted as follows (from highest weight to lowest weight): CAM2 KB; CAM2KD; CAM2KA; BMP-1; angiostatin; integrin alb1; SHC1; Moesin; FER; PDPK1. In particular embodiments, expression values of genes or proteins for diagnosing PTL<35 weeks of gestation may be weighted as follows (from highest weight to lowest weight): CAM2 KB; CAM2KA; BMP-1; CAM2KD; angiostatin; TBP; ENA-78; neurotrophin-5; PDGF Rb; FER.

Genes or proteins disclosed or described herein may also be grouped into classes, and each class given a weighted score. In particular embodiments, expression values of genes or proteins for diagnosing PTL may be grouped into classes and weighted as follows (from highest weight to lowest weight): Class 1: CAM2 KB; CAM2KA; BMP-1; CAM2KD and angiostatin; Class 2: integrin alb1; TBP and ENA-78; Class 3: SHC1 and Moesin; Class 4: FER; PDPK1 and neurotrophin-5; and Class 5: esterase D; PDGF Rb and LRRT1. In particular embodiments, expression values of genes or proteins for diagnosing PTL may be grouped into classes and weighted as follows (from highest weight to lowest weight): Class 1: CAM2 KB; CAM2KA; BMP-1; CAM2KD; angiostatin; integrin alb1; TBP and ENA-78; Class 2: SHC1; Moesin; FER; PDPK1 and neurotrophin-5; Class 3: esterase D; PDGF Rb and LRRT1. In particular embodiments, expression values of genes or proteins for diagnosing PTL<37 weeks gestation may be grouped into classes and weighted as follows (from highest weight to lowest weight): Class 1: CAM2 KB and CAM2KD; Class 2: CAM2KA and BMP-1; Class 3: angiostatin and integrin alb1; Class 4: SHC1 and Moesin; and Class 5: FER and PDPK1. In particular embodiments, expression values of genes or proteins for diagnosing PTL<37 weeks gestation may be grouped into classes and weighted as follows (from highest weight to lowest weight): Class 1: CAM2 KB; CAM2KD; CAM2KA; BMP-1 and angiostatin; Class 2: integrin alb1 and SHC1; Class 3: Moesin; FER and PDPK1. In particular embodiments, expression values of genes or proteins for diagnosing PTL<35 weeks gestation may be grouped into classes and weighted as follows (from highest weight to lowest weight): Class 1: CAM2 KB; CAM2KA and BMP-1; Class 2: CAM2KD and angiostatin; Class 3: TBP and ENA-78; Class 4: neurotrophin-5 and PDGF Rb; Class 5: FER. In particular embodiments, expression values of genes or proteins for diagnosing PTL<35 weeks gestation may be grouped into classes and weighted as follows (from highest weight to lowest weight): Class 1: CAM2 KB; CAM2KA; BMP-1 and CAM2KD; Class 2: angiostatin; TBP and ENA-78; Class 3: neurotrophin-5; PDGF Rb and FER.

Any gene or protein described or disclosed herein or class of genes or proteins described or disclosed herein can be excluded from a particular value calculation. For example, in particular embodiments, Class 5 is excluded. In particular embodiments, Class 4 is excluded. In particular embodiments, Class 3 is excluded. In particular embodiments, Class 2 is excluded. In particular embodiments, Class 1 is excluded. In further embodiments, groups of classes can be excluded, for example, Classes 5 and 4; 5 and 3; 5 and 2; 4 and 3; 4 and 2; 3 and 2; etc.

(vi) Methods. Particular embodiments disclosed herein include obtaining a sample derived from a pregnant subject; and assaying the sample to obtain expression values of one or more biomarkers described herein.

Particular embodiments disclosed herein also include obtaining a sample derived from a pregnant subject; assaying the sample to obtain expression values of one or more biomarkers described herein; comparing the expression values of the one or more biomarkers described herein to a reference level; and predicting a positive or negative risk of PTL and/or preterm birth in the pregnant subject based on the assaying.

Additional diagnostic criteria may also be considered in combination with the protein biomarkers disclosed herein. Additional diagnostic criteria include cervical length, maternal microbiome (including microbiota, among other possible sites, from the vagina and gastrointestinal tract), ethnicity, weight before and during pregnancy, age and gestational age at sampling, education, race, smoking status, height, previous live births, previous PTL or birth, diabetes (pre-pregnancy and gestational), pre-pregnancy hypertension, and presence or absence of sexually transmitted diseases.

When a risk for PTL is identified, the systems and methods disclosed herein provide effective interventions. Any treatments that prevent, delay, reduce and/or stop PTL may be used. Exemplary treatments include antenatal corticosteroids, antibiotics, tocolytics, progesterone, cerclage, and bed rest. In particular embodiments, treating a pregnant subject includes delivering a therapeutically effective amount of a treatment. A therapeutically effective amount include those that provide effective amounts, prophylactic treatments, and/or therapeutic treatments.

An "effective amount" is the amount of a treatment necessary to result in a desired physiological change in the subject. Effective amounts are often administered for research purposes. Effective amounts disclosed herein can prevent, delay reduce, and/or stop PTL.

A "prophylactic treatment" includes a treatment administered to a subject who was identified as at risk for PTL but who does not yet display symptoms of PTL, or displays only early signs or symptoms of PTL or displayed signs or symptoms of PTL in a previous pregnancy, such that treatment is administered for the purpose of decreasing the risk for PTL. Thus, a prophylactic treatment functions as a preventative treatment against PTL.

A "therapeutic treatment" includes a treatment administered to a subject who displays symptoms of PTL and is administered to the subject for the purpose of diminishing or eliminating those symptoms. The therapeutic treatment can reduce and/or stop PTL.

The actual dose or treatment administered to a particular subject can be determined by a physician, veterinarian or researcher taking into account parameters such as physical and physiological factors including target, body weight, severity of risk for PTL, severity of PTL, previous or concurrent therapeutic interventions, idiopathy of the subject, and route of administration.

Exemplary doses can include from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, etc.

(vii) Kits. Systems disclosed herein include kits to detect the biomarkers disclosed herein. In particular embodiments, a kit of the present disclosure is used to predict risk of PTL and/or preterm birth in a pregnant subject. Kits can include reagents to detect expression of one or more biomarkers disclosed herein. Reagents to detect expression of one or more biomarkers include one or more binding ligands. Binding ligands can include an aptamer, a ligand, a receptor, an allosteric regulator, an antibody, an affibody, or a fragment of any thereof. In particular embodiments, a kit of the disclosure includes detection reagents which create quantifiable signals based on concentration dependent reactions with biomarker species in the sample. For example, biomarker panel analysis may employ enzymes, colloidal metals, carbon, biotin labels, visible labels, fluorescent labels, latex beads impregnated with visual or fluorescent dyes, or a combination of these for detection of biomarker expression. A kit may further include elements such as reference standards of the biomarkers to be measured.

In particular embodiments, a kit can include physical elements of a quantitative multiplex assay, for example a direct assay, an indirect assay, a sandwich assay, or a competitive assay, as known in the art, for example, an ELISA assay, wherein the assay elements enable the detection of multiple biomarkers. Exemplary multiplex assay platforms include those described in U.S. Pat. No. 8,075,854, US 2002/0127740, and US 2004/0241776. In particular embodiments, a kit includes a solid support to which one or more individually addressable patches of binding ligands are present. In particular embodiments, the binding ligands of each patch are directed to a specific biomarker predictive of PTL. In particular embodiments, individually addressable patches of absorbent or adsorbing material are present, onto which individual aliquots of sample may be immobilized. Solid supports may include, for example, a chip, wells of a microtiter plate, a bead or resin. The chip or plate of the kit may include a chip configured for automated reading, as known in the art. In particular embodiments, a kit includes an array that measures expression of one or more biomarkers disclosed herein. In particular embodiments, the array includes one or more wells coated with ligands that bind one or more biomarkers disclosed herein. In particular embodiments, a kit of the disclosure include aptamers present on a solid support, which can capture selected biomarkers from the sample and release them in response to a desorption treatment for mass spectroscopic analysis.

Associated with such kits can be a safety notice. In particular embodiments, the kits may include instructions for using the kit in the methods disclosed herein. In particular embodiments, the kit may include instructions regarding preparation of samples, when to obtain samples, use of components of the kit to measure expression of one or more biomarkers disclosed herein, use of measurements obtained on biomarkers to predict risk of PTL and/or preterm birth, therapeutic interventions if a risk of PTL and/or preterm birth is detected, proper disposal of the related waste, and the like. The instructions can be in the form of printed instructions provided inside a carton containing the kit. The instructions can also be printed on the carton and/or on other portions of the kit. Instructions may be in the form of a sheet, pamphlet, brochure, CD-Rom, or computer-readable device, or can provide directions to instructions at a remote location, such as a website. The instructions may be in English and/or in any national or regional language.

In particular embodiments, the kits described herein include some or all of the necessary supplies needed to use the kit, thereby eliminating the need to locate and gather such supplies. The supplies can include pipettes, pipette tips, buffers, reagents, plates, films, tubes, tube racks, gloves, sterilizing liquids, and the like.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. A method including:
   obtaining a sample derived from a subject;
   contacting the sample with one or more binding ligands that bind one or more of biomarkers CAMK2A, CAMK2B, CAMK2D, BMP-1, and angiostatin; and
   detecting binding of the one or more binding ligands with one or more of biomarkers CAMK2A, CAMK2B, CAMK2D, BMP-1, and angiostatin.
2. A method of embodiment 1, wherein the detecting binding indicates a risk determination for preterm labor (PTL).
3. A method of embodiment 1 or 2, wherein the one or more biomarkers includes a sequence selected from SEQ ID NOs: 1-5.
4. A method of any of embodiments 1-3, wherein the one or more biomarkers are encoded by a sequence selected from SEQ ID NOs: 20-24.
5. A method of any of embodiments 1-4 further including:
   contacting the sample with one or more binding ligands that bind one or more of biomarkers Integrin alb1, SHC1, Moesin, FER, PDPK1, TBP, ENA-78, neurotrophin-5, PDGF Rb, PIGF, LRRT1, and/or esterase D; and detecting binding of the one or more binding ligands with one or more of biomarkers Integrin alb1, SHC1, Moesin, FER, PDPK1, TBP, ENA-78, neurotrophin-5, PDGF Rb, PIGF, LRRT1, and/or esterase D.
6. A method of embodiment 5, wherein the one or more biomarkers includes a sequence selected from SEQ ID NOs: 6-18.
7. A method of any of embodiments 1-6, wherein the sample is amniotic fluid, blood, serum, or urine.
8. A method of any of embodiments 1-7, wherein the sample is obtained between the $8^{th}$ and $14^{th}$ weeks of gestation.
9. A method of any of embodiments 1-7, wherein the sample is obtained during the 8th week of pregnancy or later.
10. A method of any of embodiments 1-9, wherein a positive risk determination is predictive of PTL at <37 weeks of gestation.
11. A method of any of embodiments 1-10, wherein a positive risk determination is predictive of PTL at <35 weeks of gestation.
12. A method of any of embodiments 1-11, wherein if the risk determination is positive, a prophylactic treatment is administered to the subject.
13. A method of embodiment 12, wherein the treatment is antenatal corticosteroids, antibiotics, tocolytics, progesterone, cerclage, and/or bed rest.
14. A kit for practicing a method of any of embodiments 1-13.

15. A biomarker panel including one or more binding ligands that bind biomarkers selected from CAMK2A, CAMK2B, CAMK2D, BMP-1, and angiostatin.
16. A biomarker panel of embodiment 15 including one or more binding ligands that bind biomarkers selected from CAMK2A, CAMK2B, and BMP-1.
17. A method for detecting risk of PTL and/or preterm birth in a pregnant subject including:
    (i) assaying a sample obtained from the pregnant subject for expression of one or more of biomarkers CAMK2A, CAMK2B, CAMK2D, BMP-1, and/or angiostatin; and
    (ii) predicting a positive or negative risk of PTL and/or preterm birth in the pregnant subject based on the assaying.
18. A method of embodiment 17 wherein the assaying includes measuring expression of CAMK2A, CAMK2B, CAMK2D, BMP-1, and angiostatin.
19. A method of embodiment 17 or 18 wherein the assaying includes measuring expression of CAMK2A, CAMK2B, and BMP-1.
20. A method of any of embodiments 17-19, wherein the measuring expression includes loading samples into
    one or more wells coated with CAMK2A binding ligands,
    one or more wells coated with CAMK2B binding ligands,
    one or more wells coated with CAMK2D binding ligands,
    one or more wells coated with BMP-1 binding ligands, and/or
    one or more wells coated with angiostatin binding ligands.
21. A method of any of embodiments 17, 18, and 20, wherein the predicting a positive or negative risk of PTL and/or preterm birth is based on measuring expression of CAMK2A, CAMK2B, CAMK2D, BMP-1, and angiostatin.
22. A method of any of embodiments 17, 19, and 20, wherein the predicting a positive or negative risk of PTL and/or preterm birth is based on measuring expression of CAMK2A, CAMK2B, and BMP-1.
23. A method of any of embodiments 17-22, wherein the assaying further includes measuring expression of one or more of biomarkers Integrin alb1, SHC1, Moesin, FER, PDPK1, TBP, ENA-78, neurotrophin-5, PDGF Rb, PIGF, LRRT1, and/or esterase D.
24. A method of embodiment 23, wherein the assaying further includes loading samples into
    one or more wells coated with Integrin alb1 binding ligands,
    one or more wells coated with SHC1 binding ligands,
    one or more wells coated with Moesin binding ligands,
    one or more wells coated with FER binding ligands,
    one or more wells coated with PDPK1 binding ligands,
    one or more wells coated with TBP binding ligands,
    one or more wells coated with ENA-78 binding ligands,
    one or more wells coated with neurotrophin-5 binding ligands,
    one or more wells coated with PDGF Rb binding ligands,
    one or more wells coated with PIGF binding ligands,
    one or more wells coated with LRRT1 binding ligands, and/or
    one or more wells coated with esterase D binding ligands.
25. A method of embodiment 23 or 24, wherein the predicting a positive or negative risk of PTL and/or preterm birth is based on measuring expression of Integrin alb1, SHC1, Moesin, FER, PDPK1, TBP, ENA-78, neurotrophin-5, PDGF Rb, PIGF, LRRT1, and/or esterase D.
26. A method of any of embodiments 23-25, wherein the one or more biomarkers includes a sequence selected from SEQ ID NOs: 6-18.
27. A method of any of embodiments 17-26, wherein the sample is obtained between the 8th and 14th week of the pregnant subject's gestation.
28. A method of any of embodiments 17-27, wherein predicting a positive risk of PTL and/or preterm birth includes predicting PTL and/or preterm birth at <37 weeks of gestation.
29. A method of any of embodiments 17-28, wherein predicting a positive risk of PTL and/or preterm birth includes predicting PTL and/or preterm birth at <35 weeks of gestation.
30. A method of any of embodiments 17-29, wherein the one or more biomarkers includes a sequence selected from SEQ ID NOs: 1-5.
31. A method of any of embodiments 17-30, wherein the one or more biomarkers are encoded by a sequence selected from SEQ ID NOs: 20-24.
32. A method of any of embodiments 17-31, wherein if the predicting a risk of PTL and/or preterm birth is positive, a prophylactic treatment is administered to the subject.
33. A method of embodiment 32, wherein the treatment is antenatal corticosteroids, antibiotics, tocolytics, progesterone, cerclage, and/or bed rest.
34. A kit for predicting risk of PTL and/or preterm birth in a pregnant subject including:
    (i) an array that measures expression of one or more of biomarkers CAMK2A, CAMK2B, CAMK2D, BMP-1, and/or angiostatin; and
    (ii) instructions that (a) direct assaying a sample obtained from the pregnant subject for one or more of biomarkers CAMK2A, CAMK2B, CAMK2D, BMP-1, and/or angiostatin, and (b) provide reference levels to predict a positive risk of PTL and/or preterm birth in the pregnant subject based on the assaying.
35. A kit of embodiment 34 wherein the array measures CAMK2A, CAMK2B, CAMK2D, BMP-1, and angiostatin.
36. A kit of embodiment 34 or 35 including instructions that direct use of the measurement of CAMK2A, CAMK2B, CAMK2D, BMP-1, and angiostatin to predict risk of PTL and/or preterm birth at less than 37 weeks of gestation.
37. A kit of embodiment 34 wherein the array measures CAMK2A, CAMK2B, and BMP-1.
38. A kit of embodiment 37 including instructions that direct use of the measurement of CAMK2A, CAMK2B, and BMP-1 to predict risk of PTL and/or preterm birth at less than 35 weeks of gestation.
39. A kit of any of embodiments 34-38 wherein the array includes:
    one or more wells coated with CAMK2A binding ligands,
    one or more wells coated with CAMK2B binding ligands,
    one or more wells coated with CAMK2D binding ligands,
    one or more wells coated with BMP-1 binding ligands, and/or
    one or more wells coated with angiostatin binding ligands.
40. A kit of any of embodiments 34-39, wherein the one or more biomarkers include a sequence selected from SEQ ID NOs: 1-5.
41. A kit of any of embodiments 34-40, wherein the one or more biomarkers are encoded by a sequence selected from SEQ ID NOs: 20-24.

42. A kit of any of embodiments 34-41, wherein the instructions direct that the sample be obtained between the 8th and 14th week of the pregnant subject's gestation.
43. A kit of any of embodiments 34-42, wherein the instructions direct that the sample is a blood or serum sample.
44. A kit of any of embodiments 34-43, wherein the instructions direct a therapeutic intervention when a risk of PTL and/or preterm birth is detected.
45. A kit of embodiment 44 wherein the therapeutic intervention is selected from antenatal corticosteroids, antibiotics, tocolytics, progesterone, cerclage, and/or bed rest.
46. A method including:
obtaining a sample derived from a subject;
contacting the sample with one or more binding ligands that bind one or more biomarkers of Table 1, Table 2, or FIGS. 1-10; and
detecting binding of the one or more binding ligands with the one or more biomarkers of Table 1, Table 2, or FIGS. 1-10.
47. A method of embodiment 46, wherein the detecting binding indicates a risk determination for preterm labor (PTL).
48. A method of embodiment 46 or 47, wherein the one or more biomarkers includes a sequence selected from SEQ ID NOs: 1-18.
49. A method of any of embodiments 46-48, wherein the one or more biomarkers are encoded by a sequence selected from SEQ ID NOs: 20-24.
50. A method of any of embodiments 46-49, wherein the sample is amniotic fluid, blood, serum, or urine.
51. A method of any of embodiments 46-50, wherein the sample is obtained between the $8^{th}$ and $14^{th}$ weeks of gestation.
52. A method of any of embodiments 46-50, wherein the sample is obtained during the 8th week of pregnancy or later.
53. A method of any of embodiments 46-52, wherein a positive risk determination is predictive of PTL at <37 weeks of gestation.
54. A method of any of embodiments 46-53, wherein a positive risk determination is predictive of PTL at <35 weeks of gestation.
55. A method of any of embodiments 46-54, wherein if the risk determination is positive, a prophylactic treatment is administered to the subject.
56. A method of embodiment 55, wherein the treatment is antenatal corticosteroids, antibiotics, tocolytics, progesterone, cerclage, and/or bed rest.
57. A kit for practicing a method of any of embodiments 46-56.
58. A biomarker panel including one or more binding ligands that bind biomarkers described in Table 1, Table 2, or FIGS. 1-10.

EXAMPLES

Example 1

This example describes a non-invasive test that can be performed by taking a maternal plasma sample at 8-14 weeks of gestation and measure a panel of proteins to identify the women at risk for preterm delivery.

The tables below list the proteins predictive of preterm delivery (PTD) at <37 weeks (Table 1) and PTD<35 weeks (Table 2) providing the identity of the proteins (Protein Symbol, Name, and Uniprot database ID), and a measures of their discrimination between cases and controls (Fold change: signed ratio of average abundance with negative values representing lower levels in cases; p: probability value from a two sample t-test; q=adjusted p-value using the false discovery rate method; AUC: area under the receiver operating characteristic curve estimated by leave-one-out-cross-validation).

TABLE 1

Proteins predictive of preterm delivery at <37 weeks of gestation

| Marker | UniProt | Fold change | p | q | AUC |
|---|---|---|---|---|---|
| CAMK2B | Q13554 | −1.4 | 0.0000 | 0.004 | 0.74 |
| CAMK2D | Q13557 | −1.4 | 0.0000 | 0.007 | 0.73 |
| Integrin a1b1 | P56199, P05556 | −1.3 | 0.0001 | 0.022 | 0.71 |
| CAMK2A | Q9UQM7 | −1.2 | 0.0002 | 0.051 | 0.71 |
| BMP-1 | P13497 | 1.1 | 0.0008 | 0.134 | 0.66 |
| SHC1 | P29353 | −1.2 | 0.0009 | 0.134 | 0.68 |
| Moesin | P26038 | −1.2 | 0.0011 | 0.134 | 0.66 |
| FER | P16591 | −1.3 | 0.0013 | 0.134 | 0.67 |
| PDPK1 | O15530 | −1.2 | 0.0013 | 0.134 | 0.66 |

TABLE 2

Proteins predictive of preterm delivery at <35 weeks of gestation

| SYMBOL | UniProt | Fold change | p | q | AUC |
|---|---|---|---|---|---|
| TBP | P20226 | 1.3 | 0.0001 | 0.055 | 0.64 |
| CAMK2B | Q13554 | −1.4 | 0.0001 | 0.055 | 0.74 |
| CAMK2D | Q13557 | −1.4 | 0.0003 | 0.080 | 0.73 |
| ENA-78 | P42830 | 1.1 | 0.0004 | 0.088 | 0.66 |
| BMP-1 | P13497 | 1.2 | 0.0005 | 0.088 | 0.73 |
| Integrin a1b1 | P56199, P05556 | −1.4 | 0.0011 | 0.173 | 0.72 |
| Neurotrophin-5 | P34130 | 1.2 | 0.0016 | 0.173 | 0.7 |
| CAMK2A | Q9UQM7 | −1.2 | 0.0017 | 0.173 | 0.73 |
| PDGF Rb | P09619 | −1.3 | 0.0029 | 0.225 | 0.71 |
| FER | P16591 | −1.3 | 0.0029 | 0.225 | 0.69 |

Based on the full set of patients (N=77 normal pregnancies, N=44 PTD<37 weeks), it was determined that the best combination of proteins to predict PTD<37 weeks included only CAMK2B, reaching a sensitivity of 56% at 80% specificity, likelihood ratio positive 2.8 (see FIG. 1 for full ROC curve). However, when subsets of patients were selected with replacement (bootstrap) and combinations of up to 5 proteins were combined in a linear discriminant analysis model (LDA), several proteins were frequently selected in the best combination such as: CAMK2B (56% of the 200 bootstrap trials), CAMK2D (30%), CAMK2A (19%), Angiostatin (16%), BMP-1 (14%).

Figure 2:
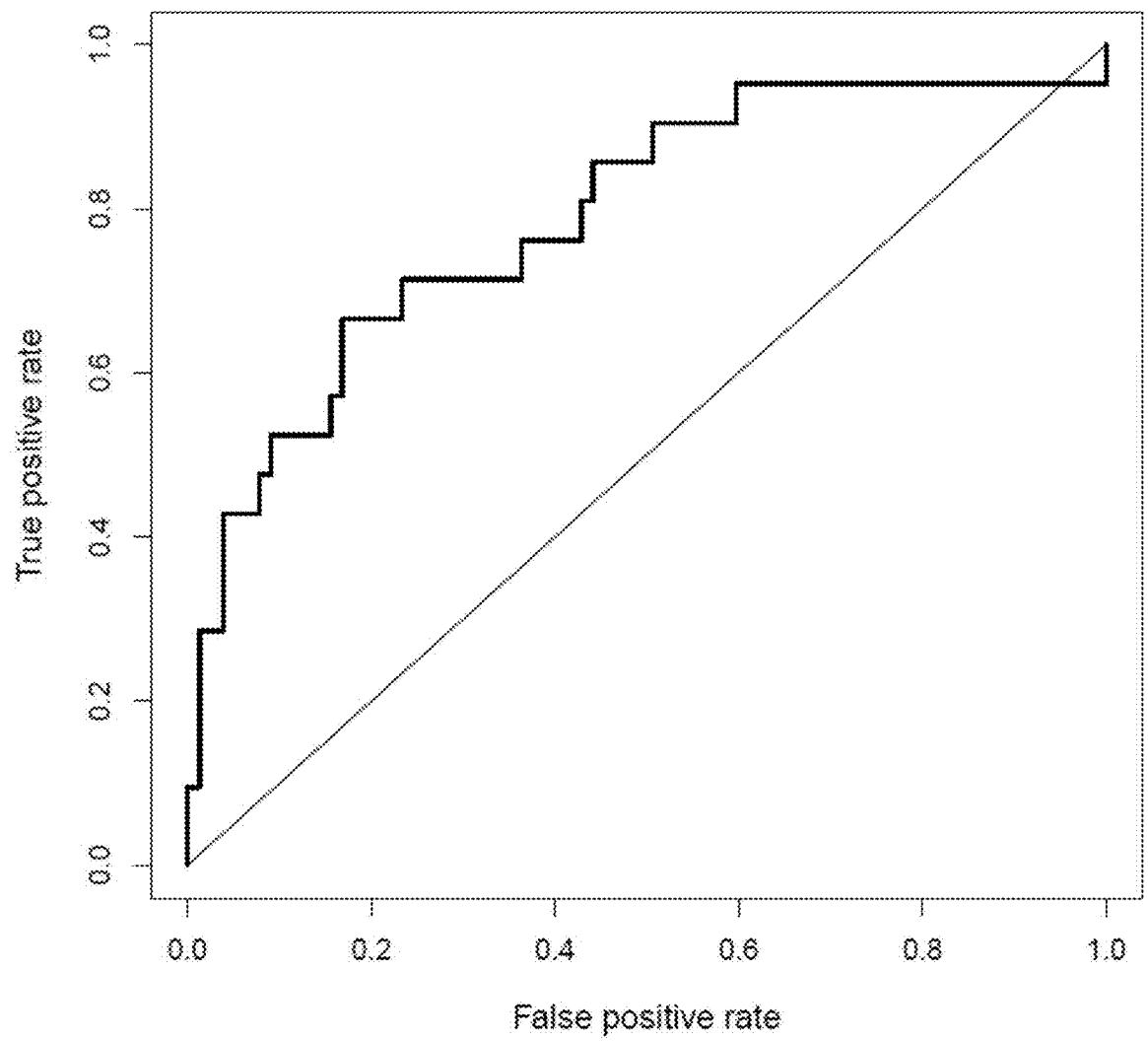
FIG. 2. Receiver operating characteristic curve estimated by leave-one-out-cross-validation for CAMK2A+CAMK2B+BMP-1 in predicting PTD<37 weeks (sensitivity of 66% at 78% specificity, AUC=0.79).
Figure 4:
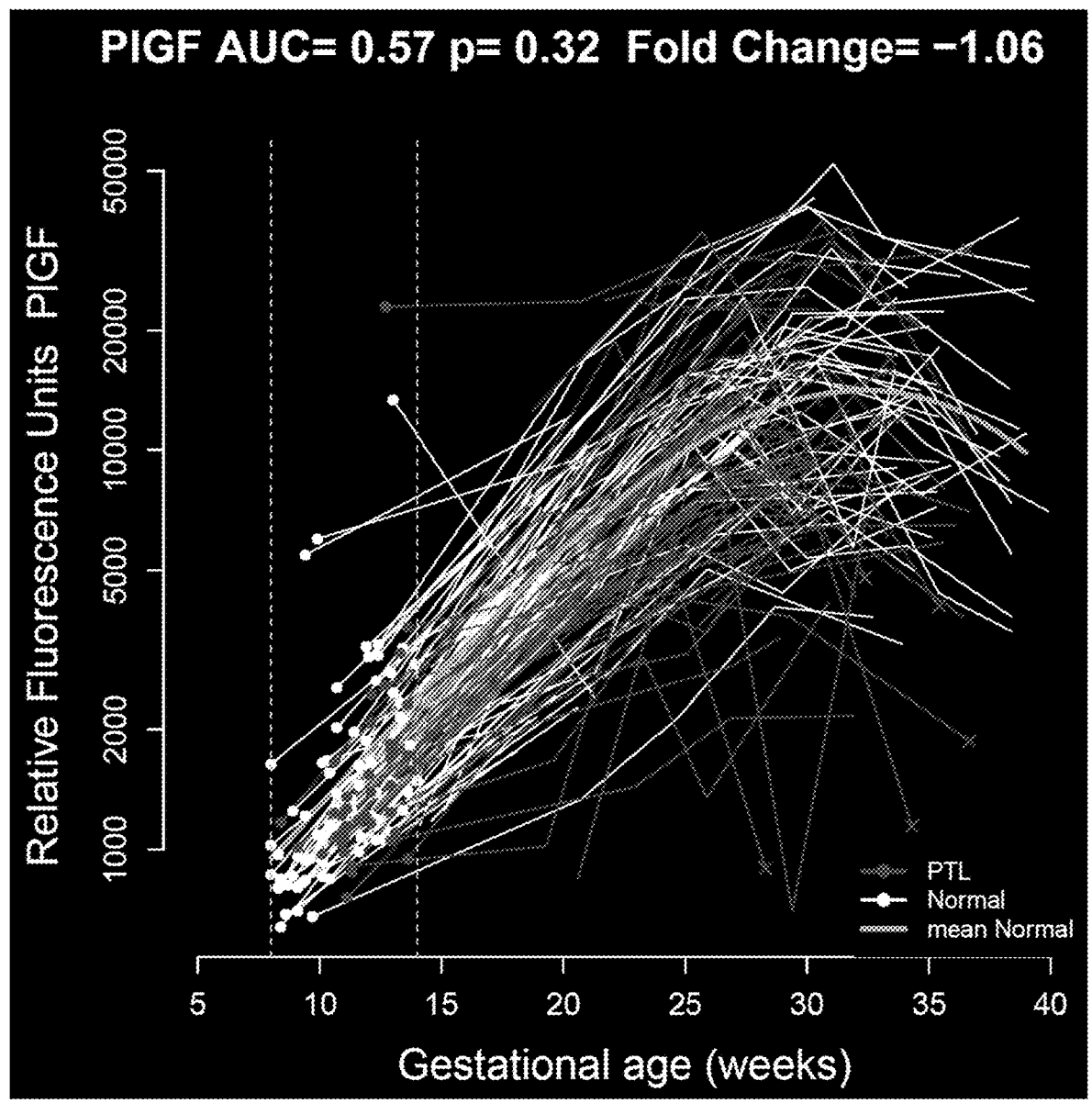
Figure 5:
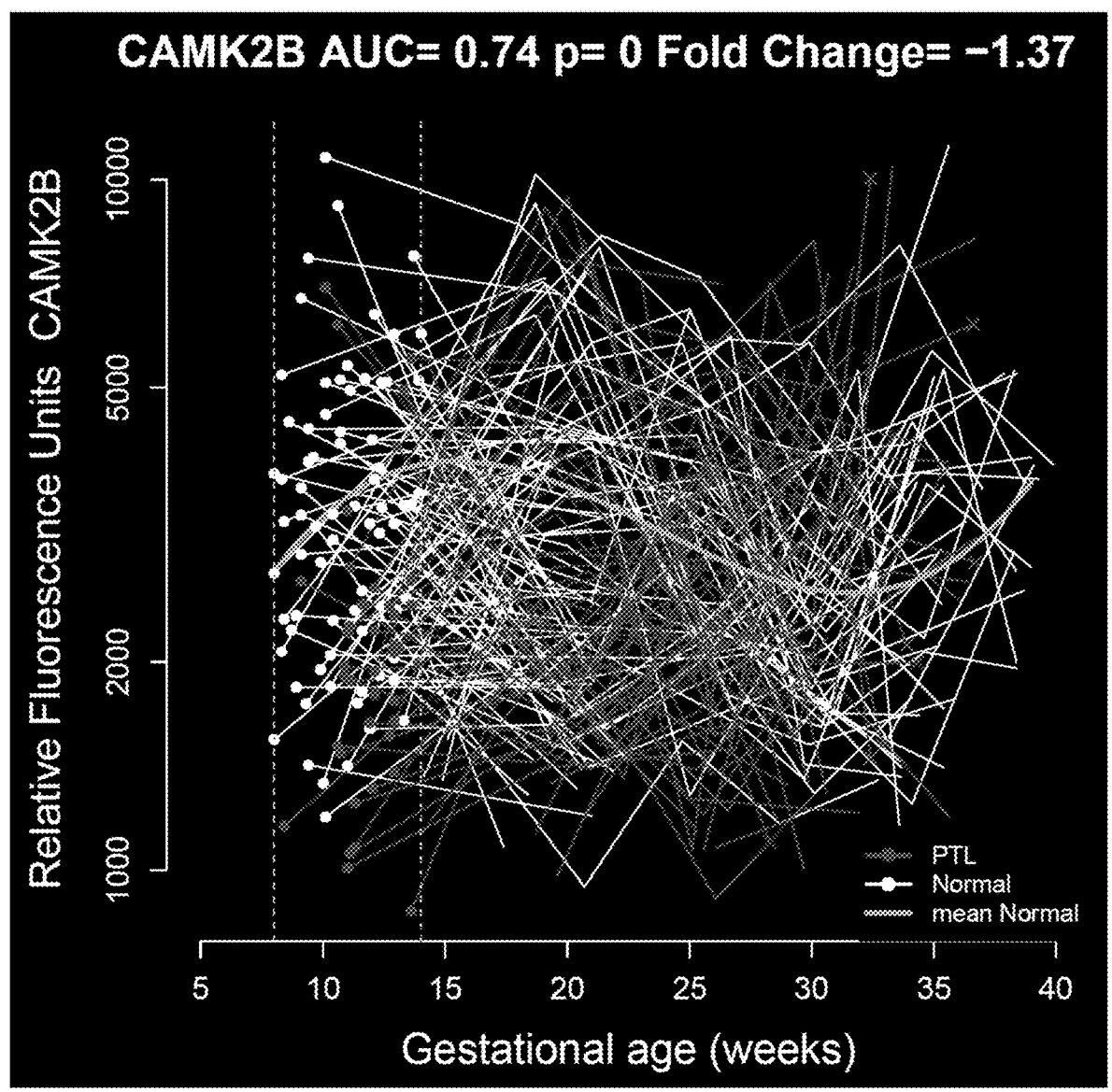
Figure 6:
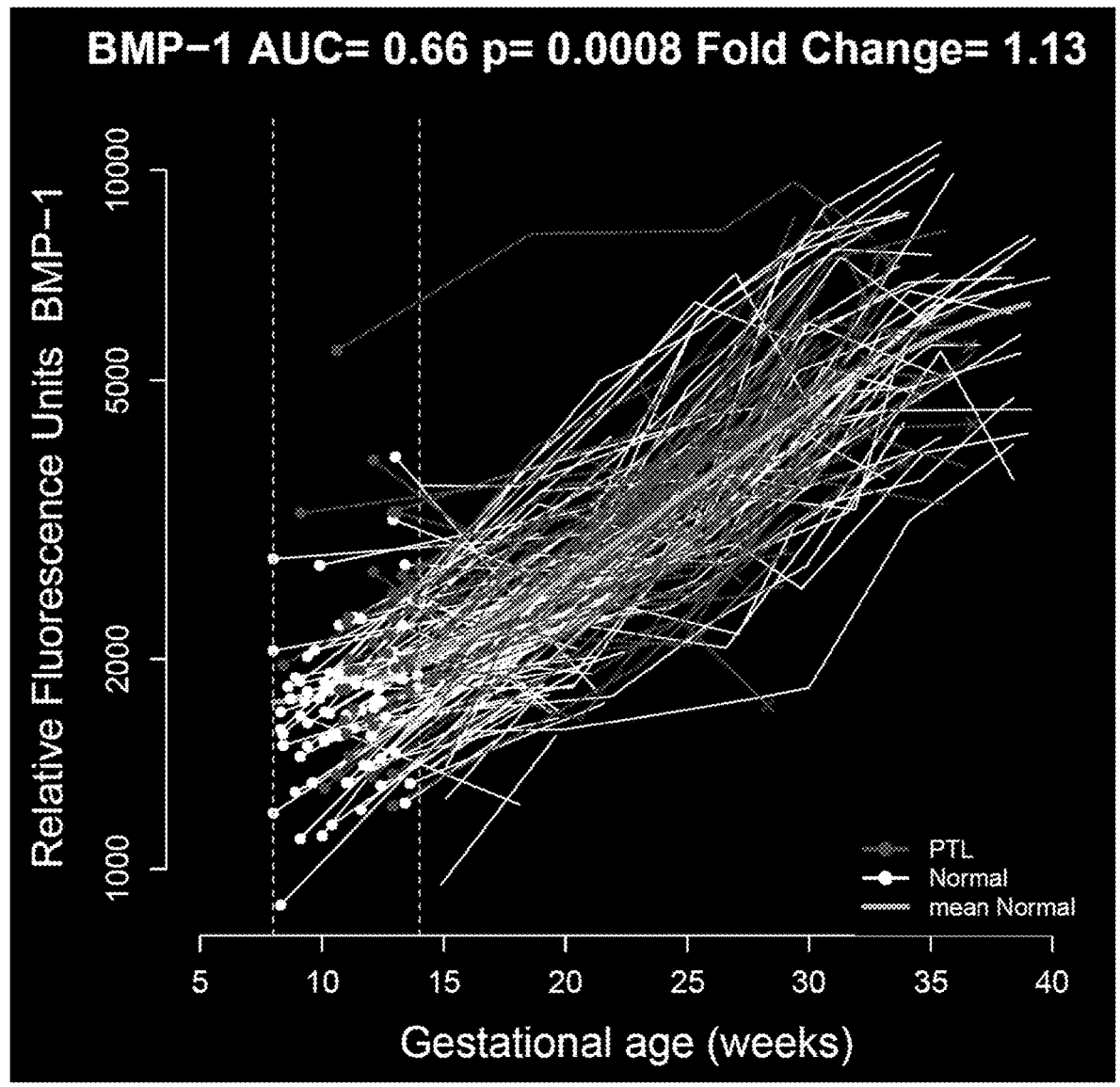
Figure 10:
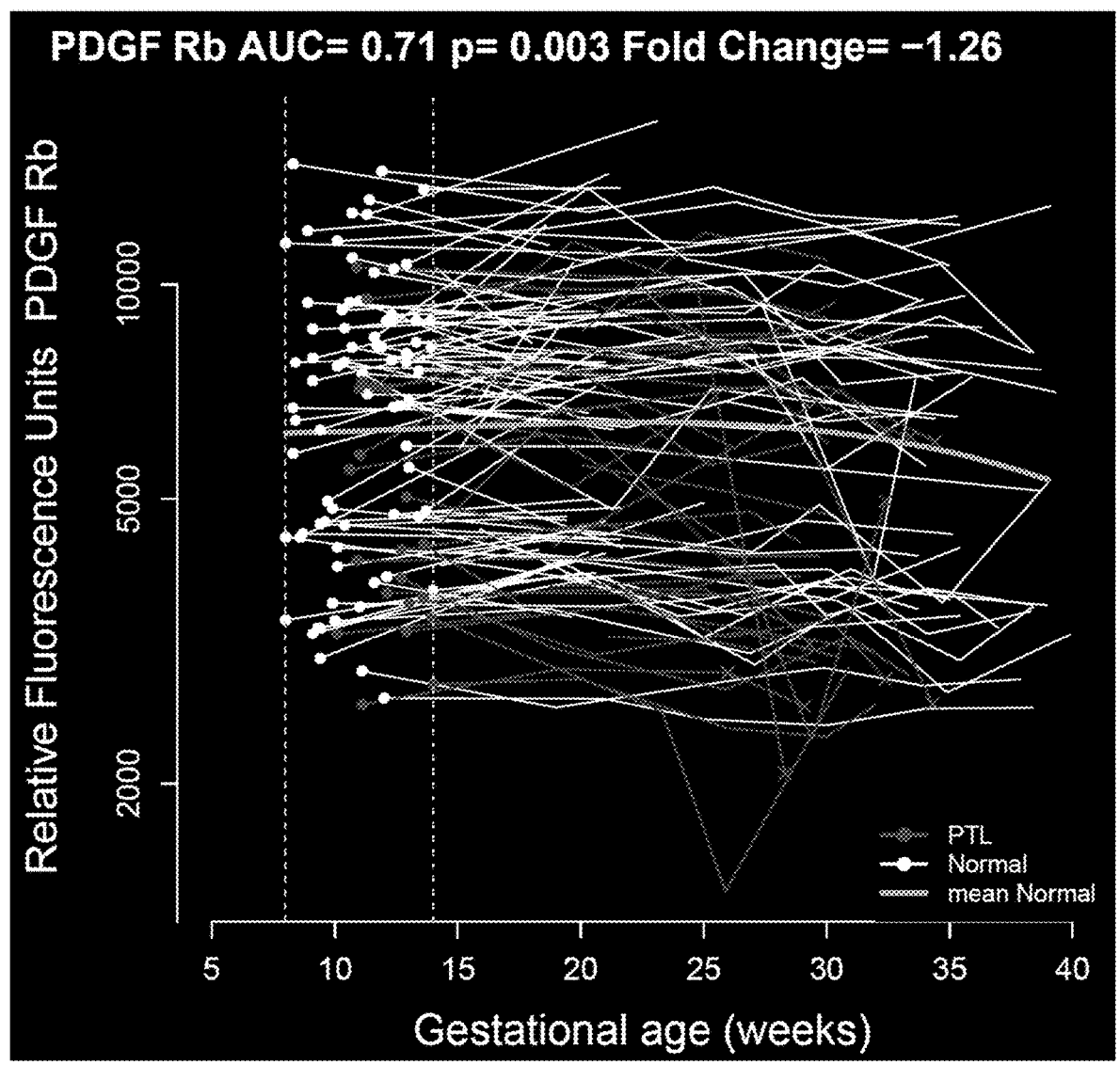

Similarly, based on the available sample size (N=77 normal pregnancies, N=21 PTD<35 weeks), the best combination of proteins to predict PTD<35 weeks included CAMK2A, CAMK2B, and BMP-1, combination reaching a sensitivity of 66% at 78% specificity, likelihood ratio positive 3.0 (see FIG. 2 for full ROC curve).

Example 2

Proteomics of maternal plasma to predict spontaneous PTL. Portions of this example overlap with data and methods described in Example 1.

Study Objective. The objective of the study was to identify maternal plasma proteins that are predictive of spontaneous PTL before 14 weeks of gestation.

Study Design. Study participants included 90 subjects with normal pregnancies (median 1, range 2-6), and 83 subjects with PTL (<37 weeks; median 4, range 2-5).

Materials and Methods. For proteomics, Slow Off-rate Modified Aptamers (SOMAmer) nucleotides were used. The SOMAmers bind to native folded proteins and can demonstrate stronger and longer binding than antibodies (Davies et al. Proc Natl Acad Sci USA 2012; 109:19971-19976). Protein abundance was expressed as Z-scores (mean and SD estimated by linear mixed-effects models). Gestational age interval for analysis was 8-14 weeks. Proteins were ranked based on partial AUC (FPR=50%). The optimal number of proteins for the model was determined, and Linear Discriminant Analysis (LDA) models were fit to predict PTL. Bootstrap was employed to obtain unbiased prediction performance estimate.

FIGS. 3-10 provide additional description and results.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in the specificity of the assessment of the risk for PTL.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The particulars shown herein are by way of example and for purposes of illustrative discussion of the preferred embodiments of the present invention only and are presented in the cause of providing what is believed to be the most useful and readily understood description of the principles and conceptual aspects of particular embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method comprising:

obtaining a plasma or serum sample derived from a pregnant human subject in the 8$^{th}$ to 14$^{th}$ week of gestation;

contacting the sample with:

(A) one or more binding ligands that bind protein biomarker CAMK2A; one or more binding ligands that bind biomarker protein CAMK2B; one or more binding ligands that bind biomarker protein CAMK2D; one or more binding ligands that bind biomarker protein BMP-1; and one or more binding ligands that bind one biomarker protein angiostatin; or (B) one or more binding ligands that bind biomarker protein CAMK2A; one or more binding ligands that bind biomarker protein CAMK2B; and one or more binding ligands that bind biomarker protein BMP-1; and detecting binding of the ligands with the biomarker proteins.

2. A method comprising:

assaying a serum or plasma sample obtained from a pregnant subject in the 8$^{th}$ to 14$^{th}$ week of gestation or earlier for expression level of biomarker proteins:

(A) CAMK2A, CAMK2B, CAMK2D, BMP-1, and angiostatin; or (B) CAMK2A, CAMK2B, and BMP-1.

* * * * *

SEQUENCE LISTING

```
<160> NUMBER OF SEQ ID NOS: 25

<210> SEQ ID NO 1
<211> LENGTH: 478
<212> TYPE: PRT
<213> ORGANISM: Homo sapiens

<400> SEQUENCE: 1

Met Ala Thr Ile Thr Cys Thr Arg Phe Thr Glu Glu Tyr Gln Leu Phe
1               5                   10                  15

Glu Glu Leu Gly Lys Gly Ala Phe Ser Val Val Arg Arg Cys Val Lys
            20                  25                  30

Val Leu Ala Gly Gln Glu Tyr Ala Ala Lys Ile Ile Asn Thr Lys Lys
        35                  40                  45

Leu Ser Ala Arg Asp His Gln Lys Leu Glu Arg Glu Ala Arg Ile Cys
    50                  55                  60

Arg Leu Leu Lys His Pro Asn Ile Val Arg Leu His Asp Ser Ile Ser
65                  70                  75                  80

Glu Glu Gly His His Tyr Leu Ile Phe Asp Leu Val Thr Gly Gly Glu
                85                  90                  95

Leu Phe Glu Asp Ile Val Ala Arg Glu Tyr Tyr Ser Glu Ala Asp Ala
            100                 105                 110

Ser His Cys Ile Gln Gln Ile Leu Glu Ala Val Leu His Cys His Gln
        115                 120                 125

Met Gly Val Val His Arg Asp Leu Lys Pro Glu Asn Leu Leu Leu Ala
    130                 135                 140

Ser Lys Leu Lys Gly Ala Ala Val Lys Leu Ala Asp Phe Gly Leu Ala
145                 150                 155                 160

Ile Glu Val Glu Gly Glu Gln Gln Ala Trp Phe Gly Phe Ala Gly Thr
                165                 170                 175

Pro Gly Tyr Leu Ser Pro Glu Val Leu Arg Lys Asp Pro Tyr Gly Lys
            180                 185                 190

Pro Val Asp Leu Trp Ala Cys Gly Val Ile Leu Tyr Ile Leu Leu Val
        195                 200                 205

Gly Tyr Pro Pro Phe Trp Asp Glu Asp Gln His Arg Leu Tyr Gln Gln
    210                 215                 220

Ile Lys Ala Gly Ala Tyr Asp Phe Pro Ser Pro Glu Trp Asp Thr Val
225                 230                 235                 240

Thr Pro Glu Ala Lys Asp Leu Ile Asn Lys Met Leu Thr Ile Asn Pro
                245                 250                 255

Ser Lys Arg Ile Thr Ala Ala Glu Ala Leu Lys His Pro Trp Ile Ser
            260                 265                 270

His Arg Ser Thr Val Ala Ser Cys Met His Arg Gln Glu Thr Val Asp
        275                 280                 285

Cys Leu Lys Lys Phe Asn Ala Arg Arg Lys Leu Lys Gly Ala Ile Leu
    290                 295                 300

Thr Thr Met Leu Ala Thr Arg Asn Phe Ser Gly Gly Lys Ser Gly Gly
305                 310                 315                 320

Asn Lys Lys Ser Asp Gly Val Lys Glu Ser Ser Glu Ser Thr Asn Thr
```

```
                   325                 330                 335
Thr Ile Glu Asp Glu Asp Thr Lys Val Arg Lys Gln Glu Ile Ile Lys
                340                 345                 350
Val Thr Glu Gln Leu Ile Glu Ala Ile Ser Asn Gly Asp Phe Glu Ser
                355                 360                 365
Tyr Thr Lys Met Cys Asp Pro Gly Met Thr Ala Phe Glu Pro Glu Ala
            370                 375                 380
Leu Gly Asn Leu Val Glu Gly Leu Asp Phe His Arg Phe Tyr Phe Glu
385                 390                 395                 400
Asn Leu Trp Ser Arg Asn Ser Lys Pro Val His Thr Thr Ile Leu Asn
                405                 410                 415
Pro His Ile His Leu Met Gly Asp Glu Ser Ala Cys Ile Ala Tyr Ile
            420                 425                 430
Arg Ile Thr Gln Tyr Leu Asp Ala Gly Gly Ile Pro Arg Thr Ala Gln
                435                 440                 445
Ser Glu Glu Thr Arg Val Trp His Arg Arg Asp Gly Lys Trp Gln Ile
            450                 455                 460
Val His Phe His Arg Ser Gly Ala Pro Ser Val Leu Pro His
465                 470                 475

<210> SEQ ID NO 2
<211> LENGTH: 666
<212> TYPE: PRT
<213> ORGANISM: Homo sapiens

<400> SEQUENCE: 2

Met Ala Thr Thr Val Thr Cys Thr Arg Phe Thr Asp Glu Tyr Gln Leu
1               5                   10                  15
Tyr Glu Asp Ile Gly Lys Gly Ala Phe Ser Val Val Arg Arg Cys Val
                20                  25                  30
Lys Leu Cys Thr Gly His Glu Tyr Ala Ala Lys Ile Ile Asn Thr Lys
            35                  40                  45
Lys Leu Ser Ala Arg Asp His Gln Lys Leu Glu Arg Glu Ala Arg Ile
        50                  55                  60
Cys Arg Leu Leu Lys His Ser Asn Ile Val Arg Leu His Asp Ser Ile
65                  70                  75                  80
Ser Glu Glu Gly Phe His Tyr Leu Val Phe Asp Leu Val Thr Gly Gly
                85                  90                  95
Glu Leu Phe Glu Asp Ile Val Ala Arg Glu Tyr Tyr Ser Glu Ala Asp
                100                 105                 110
Ala Ser His Cys Ile Gln Gln Ile Leu Glu Ala Val Leu His Cys His
            115                 120                 125
Gln Met Gly Val Val His Arg Asp Leu Lys Pro Glu Asn Leu Leu Leu
        130                 135                 140
Ala Ser Lys Cys Lys Gly Ala Ala Val Lys Leu Ala Asp Phe Gly Leu
145                 150                 155                 160
Ala Ile Glu Val Gln Gly Asp Gln Gln Ala Trp Phe Gly Phe Ala Gly
                165                 170                 175
Thr Pro Gly Tyr Leu Ser Pro Glu Val Leu Arg Lys Glu Ala Tyr Gly
                180                 185                 190
Lys Pro Val Asp Ile Trp Ala Cys Gly Val Ile Leu Tyr Ile Leu Leu
            195                 200                 205
Val Gly Tyr Pro Pro Phe Trp Asp Glu Asp Gln His Lys Leu Tyr Gln
        210                 215                 220
```

-continued

```
Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
            245                 250                 255

Pro Ala Lys Arg Ile Thr Ala His Glu Ala Leu Lys His Pro Trp Val
        260                 265                 270

Cys Gln Arg Ser Thr Val Ala Ser Met Met His Arg Gln Glu Thr Val
    275                 280                 285

Glu Cys Leu Lys Lys Phe Asn Ala Arg Arg Lys Leu Lys Gly Ala Ile
290                 295                 300

Leu Thr Thr Met Leu Ala Thr Arg Asn Phe Ser Val Gly Arg Gln Thr
305                 310                 315                 320

Thr Ala Pro Ala Thr Met Ser Thr Ala Ala Ser Gly Thr Thr Met Gly
            325                 330                 335

Leu Val Glu Gln Ala Lys Ser Leu Leu Asn Lys Lys Ala Asp Gly Val
        340                 345                 350

Lys Pro Gln Thr Asn Ser Thr Lys Asn Ser Ala Ala Thr Ser Pro
    355                 360                 365

Lys Gly Thr Leu Pro Pro Ala Ala Leu Glu Pro Gln Thr Thr Val Ile
370                 375                 380

His Asn Pro Val Asp Gly Ile Lys Glu Ser Ser Asp Ser Ala Asn Thr
385                 390                 395                 400

Thr Ile Glu Asp Glu Asp Ala Lys Ala Pro Arg Val Pro Asp Ile Leu
            405                 410                 415

Ser Ser Val Arg Arg Gly Ser Gly Ala Pro Glu Ala Glu Gly Pro Leu
        420                 425                 430

Pro Cys Pro Ser Pro Ala Pro Phe Ser Pro Leu Pro Ala Pro Ser Pro
    435                 440                 445

Arg Ile Ser Asp Ile Leu Asn Ser Val Arg Arg Gly Ser Gly Thr Pro
450                 455                 460

Glu Ala Glu Gly Pro Leu Ser Ala Gly Pro Pro Pro Cys Leu Ser Pro
465                 470                 475                 480

Ala Leu Leu Gly Pro Leu Ser Ser Pro Ser Pro Arg Ile Ser Asp Ile
            485                 490                 495

Leu Asn Ser Val Arg Arg Gly Ser Gly Thr Pro Glu Ala Glu Gly Pro
        500                 505                 510

Ser Pro Val Gly Pro Pro Pro Cys Pro Ser Pro Thr Ile Pro Gly Pro
    515                 520                 525

Leu Pro Thr Pro Ser Arg Lys Gln Glu Ile Ile Lys Thr Thr Glu Gln
530                 535                 540

Leu Ile Glu Ala Val Asn Asn Gly Asp Phe Glu Ala Tyr Ala Lys Ile
545                 550                 555                 560

Cys Asp Pro Gly Leu Thr Ser Phe Glu Pro Glu Ala Leu Gly Asn Leu
            565                 570                 575

Val Glu Gly Met Asp Phe His Arg Phe Tyr Phe Glu Asn Leu Leu Ala
        580                 585                 590

Lys Asn Ser Lys Pro Ile His Thr Thr Ile Leu Asn Pro His Val His
    595                 600                 605

Val Ile Gly Glu Asp Ala Ala Cys Ile Ala Tyr Ile Arg Leu Thr Gln
610                 615                 620

Tyr Ile Asp Gly Gln Gly Arg Pro Arg Thr Ser Gln Ser Glu Glu Thr
625                 630                 635                 640

Arg Val Trp His Arg Arg Asp Gly Lys Trp Gln Asn Val His Phe His
```

-continued

```
                645                 650                 655
Cys Ser Gly Ala Pro Val Ala Pro Leu Gln
            660                 665
```

<210> SEQ ID NO 3
<211> LENGTH: 499
<212> TYPE: PRT
<213> ORGANISM: Homo sapiens

<400> SEQUENCE: 3

```
Met Ala Ser Thr Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
            20                  25                  30

Lys Ile Pro Thr Gly Gln Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile Gln Gln Ile Leu Glu Ser Val Asn His Cys His
        115                 120                 125

Leu Asn Gly Ile Val His Arg Asp Leu Lys Pro Glu Asn Leu Leu Leu
    130                 135                 140

Ala Ser Lys Ser Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Met Trp Ala Cys Gly Val Ile Leu Tyr Ile Leu Leu
        195                 200                 205

Val Gly Tyr Pro Pro Phe Trp Asp Glu Asp Gln His Arg Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asp Leu Ile Asn Lys Met Leu Thr Ile Asn
                245                 250                 255

Pro Ala Lys Arg Ile Thr Ala Ser Glu Ala Leu Lys His Pro Trp Ile
            260                 265                 270

Cys Gln Arg Ser Thr Val Ala Ser Met Met His Arg Gln Glu Thr Val
        275                 280                 285

Asp Cys Leu Lys Lys Phe Asn Ala Arg Arg Lys Leu Lys Gly Ala Ile
    290                 295                 300

Leu Thr Thr Met Leu Ala Thr Arg Asn Phe Ser Ala Ala Lys Ser Leu
305                 310                 315                 320

Leu Lys Lys Pro Asp Gly Val Lys Glu Ser Thr Glu Ser Ser Asn Thr
                325                 330                 335

Thr Ile Glu Asp Glu Asp Val Lys Ala Arg Lys Gln Glu Ile Ile Lys
            340                 345                 350
```

```
Val Thr Glu Gln Leu Ile Glu Ala Ile Asn Asn Gly Asp Phe Glu Ala
            355                 360                 365

Tyr Thr Lys Ile Cys Asp Pro Gly Leu Thr Ala Phe Glu Pro Glu Ala
370                 375                 380

Leu Gly Asn Leu Val Glu Gly Met Asp Phe His Arg Phe Tyr Phe Glu
385                 390                 395                 400

Asn Ala Leu Ser Lys Ser Asn Lys Pro Ile His Thr Ile Ile Leu Asn
                405                 410                 415

Pro His Val His Leu Val Gly Asp Ala Ala Cys Ile Ala Tyr Ile
            420                 425                 430

Arg Leu Thr Gln Tyr Met Asp Gly Ser Gly Met Pro Lys Thr Met Gln
            435                 440                 445

Ser Glu Glu Thr Arg Val Trp His Arg Arg Asp Gly Lys Trp Gln Asn
    450                 455                 460

Val His Phe His Arg Ser Gly Ser Pro Thr Val Pro Ile Lys Pro Pro
465                 470                 475                 480

Cys Ile Pro Asn Gly Lys Glu Asn Phe Ser Gly Gly Thr Ser Leu Trp
                485                 490                 495

Gln Asn Ile

<210> SEQ ID NO 4
<211> LENGTH: 986
<212> TYPE: PRT
<213> ORGANISM: Homo sapiens

<400> SEQUENCE: 4

Met Pro Gly Val Ala Arg Leu Pro Leu Leu Gly Leu Leu Leu Leu
1               5                   10                  15

Pro Arg Pro Gly Arg Pro Leu Asp Leu Ala Asp Tyr Thr Tyr Asp Leu
                20                  25                  30

Ala Glu Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Arg Ala Ala Thr Ser Arg Pro Glu Arg
            115                 120                 125

Val Trp Pro Asp Gly Val Ile Pro Phe Val Ile Gly Gly Asn Phe Thr
    130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
            195                 200                 205

Gly Ile Val Val His Glu Leu Gly His Val Val Gly Phe Trp His Glu
    210                 215                 220
```

-continued

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
            245                 250                 255

Val Glu Ser Leu Gly Glu Thr Tyr Asp Phe Asp Ser Ile Met His Tyr
        260                 265                 270

Ala Arg Asn Thr Phe Ser Arg Gly Ile Phe Leu Asp Thr Ile Val Pro
    275                 280                 285

Lys Tyr Glu Val Asn Gly Val Lys Pro Pro Ile Gly Gln Arg Thr Arg
290                 295                 300

Leu Ser Lys Gly Asp Ile Ala Gln Ala Arg Lys Leu Tyr Lys Cys Pro
305                 310                 315                 320

Ala Cys Gly Glu Thr Leu Gln Asp Ser Thr Gly Asn Phe Ser Ser Pro
            325                 330                 335

Glu Tyr Pro Asn Gly Tyr Ser Ala His Met His Cys Val Trp Arg Ile
        340                 345                 350

Ser Val Thr Pro Gly Glu Lys Ile Ile Leu Asn Phe Thr Ser Leu Asp
    355                 360                 365

Leu Tyr Arg Ser Arg Leu Cys Trp Tyr Asp Tyr Val Glu Val Arg Asp
370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
            405                 410                 415

Arg Ser Ser Ser Asn Trp Val Gly Lys Gly Phe Phe Ala Val Tyr Glu
        420                 425                 430

Ala Ile Cys Gly Gly Asp Val Lys Lys Asp Tyr Gly His Ile Gln Ser
    435                 440                 445

Pro Asn Tyr Pro Asp Asp Tyr Arg Pro Ser Lys Val Cys Ile Trp Arg
450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
            485                 490                 495

Asp Gly His Ser Glu Ser Ser Thr Leu Ile Gly Arg Tyr Cys Gly Tyr
        500                 505                 510

Glu Lys Pro Asp Asp Ile Lys Ser Thr Ser Ser Arg Leu Trp Leu Lys
    515                 520                 525

Phe Val Ser Asp Gly Ser Ile Asn Lys Ala Gly Phe Ala Val Asn Phe
530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
            565                 570                 575

Gly Tyr Glu Leu Ala Pro Asp Lys Arg Arg Cys Glu Ala Ala Cys Gly
        580                 585                 590

Gly Phe Leu Thr Lys Leu Asn Gly Ser Ile Thr Ser Pro Gly Trp Pro
    595                 600                 605

Lys Glu Tyr Pro Pro Asn Lys Asn Cys Ile Trp Gln Leu Val Ala Pro
610                 615                 620

Thr Gln Tyr Arg Ile Ser Leu Gln Phe Asp Phe Phe Glu Thr Glu Gly
625                 630                 635                 640

Asn Asp Val Cys Lys Tyr Asp Phe Val Glu Val Arg Ser Gly Leu Thr

```
                645                 650                 655
Ala Asp Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Phe Ser Asp Lys
    690                 695                 700

Asp Glu Cys Ser Lys Asp Asn Gly Gly Cys Gln Gln Asp Cys Val Asn
705                 710                 715                 720

Thr Phe Gly Ser Tyr Glu Cys Gln Cys Arg Ser Gly Phe Val Leu His
            725                 730                 735

Asp Asn Lys His Asp Cys Lys Glu Ala Gly Cys Asp His Lys Val Thr
        740                 745                 750

Ser Thr Ser Gly Thr Ile Thr Ser Pro Asn Trp Pro Asp Lys Tyr Pro
    755                 760                 765

Ser Lys Lys Glu Cys Thr Trp Ala Ile Ser Ser Thr Pro Gly His Arg
770                 775                 780

Val Lys Leu Thr Phe Met Glu Met Asp Ile Glu Ser Gln Pro Glu Cys
785                 790                 795                 800

Ala Tyr Asp His Leu Glu Val Phe Asp Gly Arg Asp Ala Lys Ala Pro
            805                 810                 815

Val Leu Gly Arg Phe Cys Gly Ser Lys Lys Pro Glu Pro Val Leu Ala
        820                 825                 830

Thr Gly Ser Arg Met Phe Leu Arg Phe Tyr Ser Asp Asn Ser Val Gln
    835                 840                 845

Arg Lys Gly Phe Gln Ala Ser His Ala Thr Glu Cys Gly Gly Gln Val
850                 855                 860

Arg Ala Asp Val Lys Thr Lys Asp Leu Tyr Ser His Ala Gln Phe Gly
865                 870                 875                 880

Asp Asn Asn Tyr Pro Gly Gly Val Asp Cys Glu Trp Val Ile Val Ala
            885                 890                 895

Glu Glu Gly Tyr Gly Val Glu Leu Val Phe Gln Thr Phe Glu Val Glu
        900                 905                 910

Glu Glu Thr Asp Cys Gly Tyr Asp Tyr Met Glu Leu Phe Asp Gly Tyr
    915                 920                 925

Asp Ser Thr Ala Pro Arg Leu Gly Arg Tyr Cys Gly Ser Gly Pro Pro
930                 935                 940

Glu Glu Val Tyr Ser Ala Gly Asp Ser Val Leu Val Lys Phe His Ser
945                 950                 955                 960

Asp Asp Thr Ile Thr Lys Lys Gly Phe His Leu Arg Tyr Thr Ser Thr
            965                 970                 975

Lys Phe Gln Asp Thr Leu His Ser Arg Lys
        980                 985

<210> SEQ ID NO 5
<211> LENGTH: 388
<212> TYPE: PRT
<213> ORGANISM: Homo sapiens

<400> SEQUENCE: 5

Asn Arg Lys Ser Ser Ile Ile Ile Arg Met Arg Asp Val Val Leu Phe
1               5                   10                  15

Glu Lys Lys Val Tyr Leu Ser Glu Cys Lys Thr Gly Asn Gly Lys Asn
            20                  25                  30
```

```
Tyr Arg Gly Thr Met Ser Lys Thr Lys Asn Gly Ile Thr Cys Gln Lys
             35                  40                  45

Trp Ser Ser Thr Ser Pro His Arg Pro Arg Phe Ser Pro Ala Thr His
 50                  55                  60

Pro Ser Glu Gly Leu Glu Glu Asn Tyr Cys Arg Asn Pro Asp Asn Asp
 65                  70                  75                  80

Pro Gln Gly Pro Trp Cys Tyr Thr Thr Asp Pro Glu Lys Arg Tyr Asp
                 85                  90                  95

Tyr Cys Asp Ile Leu Glu Cys Glu Glu Glu Cys Met His Cys Ser Gly
            100                 105                 110

Glu Asn Tyr Asp Gly Lys Ile Ser Lys Thr Met Ser Gly Leu Glu Cys
            115                 120                 125

Gln Ala Trp Asp Ser Gln Ser Pro His Ala His Gly Tyr Ile Pro Ser
130                 135                 140

Lys Phe Pro Asn Lys Asn Leu Lys Lys Asn Tyr Cys Arg Asn Pro Asp
145                 150                 155                 160

Arg Glu Leu Arg Pro Trp Cys Phe Thr Thr Asp Pro Asn Lys Arg Trp
                165                 170                 175

Glu Leu Cys Asp Ile Pro Arg Cys Thr Thr Pro Pro Ser Ser Gly
            180                 185                 190

Pro Thr Tyr Gln Cys Leu Lys Gly Thr Gly Glu Asn Tyr Arg Gly Asn
            195                 200                 205

Val Ala Val Thr Val Ser Gly His Thr Cys Gln His Trp Ser Ala Gln
210                 215                 220

Thr Pro His Thr His Asn Arg Thr Pro Glu Asn Phe Pro Cys Lys Asn
225                 230                 235                 240

Leu Asp Glu Asn Tyr Cys Arg Asn Pro Asp Gly Lys Arg Ala Pro Trp
                245                 250                 255

Cys His Thr Thr Asn Ser Gln Val Arg Trp Glu Tyr Cys Lys Ile Pro
            260                 265                 270

Ser Cys Asp Ser Ser Pro Val Ser Thr Glu Gln Leu Ala Pro Thr Ala
275                 280                 285

Pro Pro Glu Leu Thr Pro Val Val Gln Asp Cys Tyr His Gly Asp Gly
290                 295                 300

Gln Ser Tyr Arg Gly Thr Ser Ser Thr Thr Thr Gly Lys Lys Cys
305                 310                 315                 320

Gln Ser Trp Ser Ser Met Thr Pro His Arg His Gln Lys Thr Pro Glu
                325                 330                 335

Asn Tyr Pro Asn Ala Gly Leu Thr Met Asn Tyr Cys Arg Asn Pro Asp
            340                 345                 350

Ala Asp Lys Gly Pro Trp Cys Phe Thr Thr Asp Pro Ser Val Arg Trp
            355                 360                 365

Glu Tyr Cys Asn Leu Lys Lys Cys Ser Gly Thr Glu Ala Ser Val Val
370                 375                 380

Ala Pro Pro Pro
385

<210> SEQ ID NO 6
<211> LENGTH: 1179
<212> TYPE: PRT
<213> ORGANISM: Homo sapiens

<400> SEQUENCE: 6

Met Ala Pro Arg Pro Arg Ala Arg Pro Gly Val Ala Val Ala Cys Cys
 1               5                  10                  15
```

```
Trp Leu Leu Thr Val Val Leu Arg Cys Cys Val Ser Phe Asn Val Asp
             20                  25                  30
Val Lys Asn Ser Met Thr Phe Ser Gly Pro Val Glu Asp Met Phe Gly
         35                  40                  45
Tyr Thr Val Gln Gln Tyr Glu Asn Glu Glu Gly Lys Trp Val Leu Ile
     50                  55                  60
Gly Ser Pro Leu Val Gly Gln Pro Lys Asn Arg Thr Gly Asp Val Tyr
 65                  70                  75                  80
Lys Cys Pro Val Gly Arg Gly Glu Ser Leu Pro Cys Val Lys Leu Asp
                 85                  90                  95
Leu Pro Val Asn Thr Ser Ile Pro Asn Val Thr Glu Val Lys Glu Asn
             100                 105                 110
Met Thr Phe Gly Ser Thr Leu Val Thr Asn Pro Asn Gly Gly Phe Leu
         115                 120                 125
Ala Cys Gly Pro Leu Tyr Ala Tyr Arg Cys Gly His Leu His Tyr Thr
    130                 135                 140
Thr Gly Ile Cys Ser Asp Val Ser Pro Thr Phe Gln Val Val Asn Ser
145                 150                 155                 160
Ile Ala Pro Val Gln Glu Cys Ser Thr Gln Leu Asp Ile Val Ile Val
                165                 170                 175
Leu Asp Gly Ser Asn Ser Ile Tyr Pro Trp Asp Ser Val Thr Ala Phe
            180                 185                 190
Leu Asn Asp Leu Leu Glu Arg Met Asp Ile Gly Pro Lys Gln Thr Gln
        195                 200                 205
Val Gly Ile Val Gln Tyr Gly Glu Asn Val Thr His Glu Phe Asn Leu
    210                 215                 220
Asn Lys Tyr Ser Ser Thr Glu Glu Val Leu Val Ala Ala Lys Lys Ile
225                 230                 235                 240
Val Gln Arg Gly Gly Arg Gln Thr Met Thr Ala Leu Gly Ile Asp Thr
                245                 250                 255
Ala Arg Lys Glu Ala Phe Thr Glu Ala Arg Gly Ala Arg Arg Gly Val
            260                 265                 270
Lys Lys Val Met Val Ile Val Thr Asp Gly Glu Ser His Asp Asn His
        275                 280                 285
Arg Leu Lys Lys Val Ile Gln Asp Cys Glu Asp Glu Asn Ile Gln Arg
    290                 295                 300
Phe Ser Ile Ala Ile Leu Gly Ser Tyr Asn Arg Gly Asn Leu Ser Thr
305                 310                 315                 320
Glu Lys Phe Val Glu Glu Ile Lys Ser Ile Ala Ser Glu Pro Thr Glu
                325                 330                 335
Lys His Phe Phe Asn Val Ser Asp Glu Leu Ala Leu Val Thr Ile Val
            340                 345                 350
Lys Thr Leu Gly Glu Arg Ile Phe Ala Leu Glu Ala Thr Ala Asp Gln
        355                 360                 365
Ser Ala Ala Ser Phe Glu Met Glu Met Ser Gln Thr Gly Phe Ser Ala
    370                 375                 380
His Tyr Ser Gln Asp Trp Val Met Leu Gly Ala Val Gly Ala Tyr Asp
385                 390                 395                 400
Trp Asn Gly Thr Val Val Met Gln Lys Ala Ser Gln Ile Ile Ile Pro
                405                 410                 415
Arg Asn Thr Thr Phe Asn Val Glu Ser Thr Lys Lys Asn Glu Pro Leu
            420                 425                 430
```

```
Ala Ser Tyr Leu Gly Tyr Thr Val Asn Ser Ala Thr Ala Ser Ser Gly
            435                 440                 445

Asp Val Leu Tyr Ile Ala Gly Gln Pro Arg Tyr Asn His Thr Gly Gln
450                 455                 460

Val Ile Ile Tyr Arg Met Glu Asp Gly Asn Ile Lys Ile Leu Gln Thr
465                 470                 475                 480

Leu Ser Gly Glu Gln Ile Gly Ser Tyr Phe Gly Ser Ile Leu Thr Thr
                485                 490                 495

Thr Asp Ile Asp Lys Asp Ser Asn Thr Asp Ile Leu Leu Val Gly Ala
            500                 505                 510

Pro Met Tyr Met Gly Thr Glu Lys Glu Glu Gln Gly Lys Val Tyr Val
        515                 520                 525

Tyr Ala Leu Asn Gln Thr Arg Phe Glu Tyr Gln Met Ser Leu Glu Pro
    530                 535                 540

Ile Lys Gln Thr Cys Cys Ser Ser Arg Gln His Asn Ser Cys Thr Thr
545                 550                 555                 560

Glu Asn Lys Asn Glu Pro Cys Gly Ala Arg Phe Gly Thr Ala Ile Ala
                565                 570                 575

Ala Val Lys Asp Leu Asn Leu Asp Gly Phe Asn Asp Ile Val Ile Gly
            580                 585                 590

Ala Pro Leu Glu Asp Asp His Gly Gly Ala Val Tyr Ile Tyr His Gly
        595                 600                 605

Ser Gly Lys Thr Ile Arg Lys Glu Tyr Ala Gln Arg Ile Pro Ser Gly
    610                 615                 620

Gly Asp Gly Lys Thr Leu Lys Phe Phe Gly Gln Ser Ile His Gly Glu
625                 630                 635                 640

Met Asp Leu Asn Gly Asp Gly Leu Thr Asp Val Thr Ile Gly Gly Leu
                645                 650                 655

Gly Gly Ala Ala Leu Phe Trp Ser Arg Asp Val Ala Val Val Lys Val
            660                 665                 670

Thr Met Asn Phe Glu Pro Asn Lys Val Asn Ile Gln Lys Lys Asn Cys
        675                 680                 685

His Met Glu Gly Lys Glu Thr Val Cys Ile Asn Ala Thr Val Cys Phe
    690                 695                 700

Asp Val Lys Leu Lys Ser Lys Glu Asp Thr Ile Tyr Glu Ala Asp Leu
705                 710                 715                 720

Gln Tyr Arg Val Thr Leu Asp Ser Leu Arg Gln Ile Ser Arg Ser Phe
                725                 730                 735

Phe Ser Gly Thr Gln Glu Arg Lys Val Gln Arg Asn Ile Thr Val Arg
            740                 745                 750

Lys Ser Glu Cys Thr Lys His Ser Phe Tyr Met Leu Asp Lys His Asp
        755                 760                 765

Phe Gln Asp Ser Val Arg Ile Thr Leu Asp Phe Asn Leu Thr Asp Pro
    770                 775                 780

Glu Asn Gly Pro Val Leu Asp Asp Ser Leu Pro Asn Ser Val His Glu
785                 790                 795                 800

Tyr Ile Pro Phe Ala Lys Asp Cys Gly Asn Lys Glu Lys Cys Ile Ser
                805                 810                 815

Asp Leu Ser Leu His Val Ala Thr Thr Glu Lys Asp Leu Leu Ile Val
            820                 825                 830

Arg Ser Gln Asn Asp Lys Phe Asn Val Ser Leu Thr Val Lys Asn Thr
        835                 840                 845

Lys Asp Ser Ala Tyr Asn Thr Arg Thr Ile Val His Tyr Ser Pro Asn
```

```
                    850                 855                 860
Leu Val Phe Ser Gly Ile Glu Ala Ile Gln Lys Asp Ser Cys Glu Ser
865                 870                 875                 880

Asn His Asn Ile Thr Cys Lys Val Gly Tyr Pro Phe Leu Arg Arg Gly
                    885                 890                 895

Glu Met Val Thr Phe Lys Ile Leu Phe Gln Phe Asn Thr Ser Tyr Leu
                    900                 905                 910

Met Glu Asn Val Thr Ile Tyr Leu Ser Ala Thr Ser Asp Ser Glu Glu
                    915                 920                 925

Pro Pro Glu Thr Leu Ser Asp Asn Val Val Asn Ile Ser Ile Pro Val
                    930                 935                 940

Lys Tyr Glu Val Gly Leu Gln Phe Tyr Ser Ser Ala Ser Glu Tyr His
945                 950                 955                 960

Ile Ser Ile Ala Ala Asn Glu Thr Val Pro Glu Val Ile Asn Ser Thr
                    965                 970                 975

Glu Asp Ile Gly Asn Glu Ile Asn Ile Phe Tyr Leu Ile Arg Lys Ser
                    980                 985                 990

Gly Ser Phe Pro Met Pro Glu Leu Lys Leu Ser Ile Ser Phe Pro Asn
                    995                1000                1005

Met Thr Ser Asn Gly Tyr Pro Val Leu Tyr Pro Thr Gly Leu Ser
    1010                1015                1020

Ser Ser Glu Asn Ala Asn Cys Arg Pro His Ile Phe Glu Asp Pro
    1025                1030                1035

Phe Ser Ile Asn Ser Gly Lys Lys Met Thr Thr Ser Thr Asp His
    1040                1045                1050

Leu Lys Arg Gly Thr Ile Leu Asp Cys Asn Thr Cys Lys Phe Ala
    1055                1060                1065

Thr Ile Thr Cys Asn Leu Thr Ser Ser Asp Ile Ser Gln Val Asn
    1070                1075                1080

Val Ser Leu Ile Leu Trp Lys Pro Thr Phe Ile Lys Ser Tyr Phe
    1085                1090                1095

Ser Ser Leu Asn Leu Thr Ile Arg Gly Glu Leu Arg Ser Glu Asn
    1100                1105                1110

Ala Ser Leu Val Leu Ser Ser Asn Gln Lys Arg Glu Leu Ala
    1115                1120                1125

Ile Gln Ile Ser Lys Asp Gly Leu Pro Gly Arg Val Pro Leu Trp
    1130                1135                1140

Val Ile Leu Leu Ser Ala Phe Ala Gly Leu Leu Leu Met Leu
    1145                1150                1155

Leu Ile Leu Ala Leu Trp Lys Ile Gly Phe Phe Lys Arg Pro Leu
    1160                1165                1170

Lys Lys Lys Met Glu Lys
    1175

<210> SEQ ID NO 7
<211> LENGTH: 798
<212> TYPE: PRT
<213> ORGANISM: Homo sapiens

<400> SEQUENCE: 7

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30
```

-continued

```
Lys Ser Cys Gly Glu Cys Ile Gln Ala Gly Pro Asn Cys Gly Trp Cys
         35                  40                  45
Thr Asn Ser Thr Phe Leu Gln Glu Gly Met Pro Thr Ser Ala Arg Cys
 50                  55                  60
Asp Asp Leu Glu Ala Leu Lys Lys Gly Cys Pro Pro Asp Asp Ile
 65                  70                  75                  80
Glu Asn Pro Arg Gly Ser Lys Asp Ile Lys Lys Asn Lys Asn Val Thr
                 85                  90                  95
Asn Arg Ser Lys Gly Thr Ala Glu Lys Leu Lys Pro Glu Asp Ile Thr
             100                 105                 110
Gln Ile Gln Pro Gln Gln Leu Val Leu Arg Leu Arg Ser Gly Glu Pro
         115                 120                 125
Gln Thr Phe Thr Leu Lys Phe Lys Arg Ala Glu Asp Tyr Pro Ile Asp
     130                 135                 140
Leu Tyr Tyr Leu Met Asp Leu Ser Tyr Ser Met Lys Asp Asp Leu Glu
145                 150                 155                 160
Asn Val Lys Ser Leu Gly Thr Asp Leu Met Asn Glu Met Arg Arg Ile
                165                 170                 175
Thr Ser Asp Phe Arg Ile Gly Phe Gly Ser Phe Val Glu Lys Thr Val
             180                 185                 190
Met Pro Tyr Ile Ser Thr Thr Pro Ala Lys Leu Arg Asn Pro Cys Thr
         195                 200                 205
Ser Glu Gln Asn Cys Thr Ser Pro Phe Ser Tyr Lys Asn Val Leu Ser
     210                 215                 220
Leu Thr Asn Lys Gly Glu Val Phe Asn Glu Leu Val Gly Lys Gln Arg
225                 230                 235                 240
Ile Ser Gly Asn Leu Asp Ser Pro Glu Gly Gly Phe Asp Ala Ile Met
                245                 250                 255
Gln Val Ala Val Cys Gly Ser Leu Ile Gly Trp Arg Asn Val Thr Arg
             260                 265                 270
Leu Leu Val Phe Ser Thr Asp Ala Gly Phe His Phe Ala Gly Asp Gly
         275                 280                 285
Lys Leu Gly Gly Ile Val Leu Pro Asn Asp Gly Gln Cys His Leu Glu
     290                 295                 300
Asn Asn Met Tyr Thr Met Ser His Tyr Tyr Asp Tyr Pro Ser Ile Ala
305                 310                 315                 320
His Leu Val Gln Lys Leu Ser Glu Asn Asn Ile Gln Thr Ile Phe Ala
                325                 330                 335
Val Thr Glu Glu Phe Gln Pro Val Tyr Lys Glu Leu Lys Asn Leu Ile
             340                 345                 350
Pro Lys Ser Ala Val Gly Thr Leu Ser Ala Asn Ser Ser Asn Val Ile
         355                 360                 365
Gln Leu Ile Ile Asp Ala Tyr Asn Ser Leu Ser Ser Glu Val Ile Leu
     370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
                405                 410                 415
Asn Ile Ser Ile Gly Asp Glu Val Gln Phe Glu Ile Ser Ile Thr Ser
             420                 425                 430
Asn Lys Cys Pro Lys Lys Asp Ser Asp Ser Phe Lys Ile Arg Pro Leu
         435                 440                 445
Gly Phe Thr Glu Glu Val Glu Val Ile Leu Gln Tyr Ile Cys Glu Cys
```

```
                    450                 455                 460
Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 8
<211> LENGTH: 583
<212> TYPE: PRT
<213> ORGANISM: Homo sapiens

<400> SEQUENCE: 8

Met Asp Leu Leu Pro Lys Pro Lys Tyr Asn Pro Leu Arg Asn Glu
1               5                   10                  15

Ser Leu Ser Ser Leu Glu Glu Gly Ala Ser Gly Ser Thr Pro Pro Glu
                20                  25                  30
```

-continued

```
Glu Leu Pro Ser Pro Ser Ala Ser Leu Gly Pro Ile Leu Pro Pro
             35                  40                  45

Leu Pro Gly Asp Asp Ser Pro Thr Thr Leu Cys Ser Phe Phe Pro Arg
 50                  55                  60

Met Ser Asn Leu Arg Leu Ala Asn Pro Ala Gly Gly Arg Pro Gly Ser
 65                  70                  75                  80

Lys Gly Glu Pro Gly Arg Ala Ala Asp Asp Gly Glu Gly Ile Val Gly
                     85                  90                  95

Ala Ala Met Pro Asp Ser Gly Pro Leu Pro Leu Leu Gln Asp Met Asn
             100                 105                 110

Lys Leu Ser Gly Gly Gly Arg Arg Thr Arg Val Glu Gly Gly Gln
             115                 120                 125

Leu Gly Gly Glu Glu Trp Thr Arg His Gly Ser Phe Val Asn Lys Pro
 130                 135                 140

Thr Arg Gly Trp Leu His Pro Asn Asp Lys Val Met Gly Pro Gly Val
 145                 150                 155                 160

Ser Tyr Leu Val Arg Tyr Met Gly Cys Val Glu Val Leu Gln Ser Met
                 165                 170                 175

Arg Ala Leu Asp Phe Asn Thr Arg Thr Gln Val Thr Arg Glu Ala Ile
             180                 185                 190

Ser Leu Val Cys Glu Ala Val Pro Gly Ala Lys Gly Ala Thr Arg Arg
             195                 200                 205

Arg Lys Pro Cys Ser Arg Pro Leu Ser Ser Ile Leu Gly Arg Ser Asn
 210                 215                 220

Leu Lys Phe Ala Gly Met Pro Ile Thr Leu Thr Val Ser Thr Ser Ser
 225                 230                 235                 240

Leu Asn Leu Met Ala Ala Asp Cys Lys Gln Ile Ile Ala Asn His His
             245                 250                 255

Met Gln Ser Ile Ser Phe Ala Ser Gly Gly Asp Pro Asp Thr Ala Glu
             260                 265                 270

Tyr Val Ala Tyr Val Ala Lys Asp Pro Val Asn Gln Arg Ala Cys His
             275                 280                 285

Ile Leu Glu Cys Pro Glu Gly Leu Ala Gln Asp Val Ile Ser Thr Ile
             290                 295                 300

Gly Gln Ala Phe Glu Leu Arg Phe Lys Gln Tyr Leu Arg Asn Pro Pro
 305                 310                 315                 320

Lys Leu Val Thr Pro His Asp Arg Met Ala Gly Phe Asp Gly Ser Ala
                 325                 330                 335

Trp Asp Glu Glu Glu Glu Pro Asp His Gln Tyr Tyr Asn Asp
             340                 345                 350

Phe Pro Gly Lys Glu Pro Leu Gly Gly Val Val Asp Met Arg Leu
             355                 360                 365

Arg Glu Gly Ala Ala Pro Gly Ala Arg Pro Thr Ala Pro Asn Ala
             370                 375                 380

Gln Thr Pro Ser His Leu Gly Ala Thr Leu Pro Val Gly Gln Pro Val
 385                 390                 395                 400

Gly Gly Asp Pro Glu Val Arg Lys Gln Met Pro Pro Pro Pro Cys
                 405                 410                 415

Pro Gly Arg Glu Leu Phe Asp Asp Pro Ser Tyr Val Asn Val Gln Asn
                 420                 425                 430

Leu Asp Lys Ala Arg Gln Ala Val Gly Gly Ala Gly Pro Pro Asn Pro
 435                 440                 445

Ala Ile Asn Gly Ser Ala Pro Arg Asp Leu Phe Asp Met Lys Pro Phe
```

```
                450            455             460
Glu Asp Ala Leu Arg Val Pro Pro Pro Gln Ser Val Ser Met Ala
465                 470                 475                 480

Glu Gln Leu Arg Gly Glu Pro Trp Phe His Gly Lys Leu Ser Arg Arg
                485                 490                 495

Glu Ala Glu Ala Leu Leu Gln Leu Asn Gly Asp Phe Leu Val Arg Glu
                500                 505                 510

Ser Thr Thr Thr Pro Gly Gln Tyr Val Leu Thr Gly Leu Gln Ser Gly
                515                 520                 525

Gln Pro Lys His Leu Leu Leu Val Asp Pro Glu Gly Val Val Arg Thr
            530                 535                 540

Lys Asp His Arg Phe Glu Ser Val Ser His Leu Ile Ser Tyr His Met
545                 550                 555                 560

Asp Asn His Leu Pro Ile Ile Ser Ala Gly Ser Glu Leu Cys Leu Gln
                565                 570                 575

Gln Pro Val Glu Arg Lys Leu
            580

<210> SEQ ID NO 9
<211> LENGTH: 577
<212> TYPE: PRT
<213> ORGANISM: Homo sapiens

<400> SEQUENCE: 9

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
                20                  25                  30

Val Val Lys Thr Ile Gly Leu Arg Glu Val Trp Phe Phe Gly Leu Gln
            35                  40                  45

Tyr Gln Asp Thr Lys Gly Phe Ser Thr Trp Leu Lys Leu Asn Lys Lys
50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
                100                 105                 110

Asp Asp Ile Tyr Cys Pro Pro Glu Thr Ala Val Leu Leu Ala Ser Tyr
            115                 120                 125

Ala Val Gln Ser Lys Tyr Gly Asp Phe Asn Lys Glu Val His Lys Ser
            130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
                180                 185                 190

Lys Ile Ala Gln Asp Leu Glu Met Tyr Gly Val Asn Tyr Phe Ser Ile
            195                 200                 205

Lys Asn Lys Lys Gly Ser Glu Leu Trp Leu Gly Val Asp Ala Leu Gly
            210                 215                 220

Leu Asn Ile Tyr Glu Gln Asn Asp Arg Leu Thr Pro Lys Ile Gly Phe
225                 230                 235                 240
```

```
Pro Trp Ser Glu Ile Arg Asn Ile Ser Phe Asn Asp Lys Lys Phe Val
            245                 250                 255

Ile Lys Pro Ile Asp Lys Lys Ala Pro Asp Phe Val Phe Tyr Ala Pro
        260                 265                 270

Arg Leu Arg Ile Asn Lys Arg Ile Leu Ala Leu Cys Met Gly Asn His
        275                 280                 285

Glu Leu Tyr Met Arg Arg Lys Pro Asp Thr Ile Glu Val Gln Gln
    290                 295                 300

Met Lys Ala Gln Ala Arg Glu Lys His Gln Lys Met Glu Arg
305                 310                 315                 320

Ala Met Leu Glu Asn Glu Lys Lys Arg Glu Met Ala Glu Lys Glu
                325                 330                 335

Lys Glu Lys Ile Glu Arg Glu Lys Glu Leu Met Glu Arg Leu Lys
                340                 345                 350

Gln Ile Glu Glu Gln Thr Lys Lys Ala Gln Gln Leu Glu Gln
        355                 360                 365

Thr Arg Arg Ala Leu Glu Leu Glu Gln Glu Arg Lys Arg Ala Gln Ser
    370                 375                 380

Glu Ala Glu Lys Leu Ala Lys Glu Arg Gln Glu Ala Glu Ala Lys
385                 390                 395                 400

Glu Ala Leu Leu Gln Ala Ser Arg Asp Gln Lys Lys Thr Gln Glu Gln
                405                 410                 415

Leu Ala Leu Glu Met Ala Glu Leu Thr Ala Arg Ile Ser Gln Leu Glu
                420                 425                 430

Met Ala Arg Gln Lys Lys Glu Ser Glu Ala Val Glu Trp Gln Gln Lys
            435                 440                 445

Ala Gln Met Val Gln Glu Asp Leu Glu Lys Thr Arg Ala Glu Leu Lys
450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
                485                 490                 495

Asp Ala Met Ala Lys Asp Arg Ser Glu Glu Arg Thr Thr Glu Ala
            500                 505                 510

Glu Lys Asn Glu Arg Val Gln Lys His Leu Lys Ala Leu Thr Ser Glu
                515                 520                 525

Leu Ala Asn Ala Arg Asp Glu Ser Lys Lys Thr Ala Asn Asp Met Ile
                530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met

<210> SEQ ID NO 10
<211> LENGTH: 822
<212> TYPE: PRT
<213> ORGANISM: Homo sapiens

<400> SEQUENCE: 10

Met Gly Phe Gly Ser Asp Leu Lys Asn Ser His Glu Ala Val Leu Lys
1               5                   10                  15

Leu Gln Asp Trp Glu Leu Arg Leu Leu Glu Thr Val Lys Lys Phe Met
                20                  25                  30
```

-continued

Ala Leu Arg Ile Lys Ser Asp Lys Glu Tyr Ala Ser Thr Leu Gln Asn
         35                  40                  45

Leu Cys Asn Gln Val Asp Lys Glu Ser Thr Val Gln Met Asn Tyr Val
 50                  55                  60

Ser Asn Val Ser Lys Ser Trp Leu Leu Met Ile Gln Gln Thr Glu Gln
 65                  70                  75                  80

Leu Ser Arg Ile Met Lys Thr His Ala Glu Asp Leu Asn Ser Gly Pro
                 85                  90                  95

Leu His Arg Leu Thr Met Met Ile Lys Asp Lys Gln Gln Val Lys Lys
             100                 105                 110

Ser Tyr Ile Gly Val His Gln Gln Ile Glu Ala Glu Met Ile Lys Val
         115                 120                 125

Thr Lys Thr Glu Leu Glu Lys Leu Lys Cys Ser Tyr Arg Gln Leu Ile
 130                 135                 140

Lys Glu Met Asn Ser Ala Lys Glu Lys Tyr Lys Glu Ala Leu Ala Lys
 145                 150                 155                 160

Gly Lys Glu Thr Glu Lys Ala Lys Glu Arg Tyr Asp Lys Ala Thr Met
                 165                 170                 175

Lys Leu His Met Leu His Asn Gln Tyr Val Leu Ala Leu Lys Gly Ala
             180                 185                 190

Gln Leu His Gln Asn Gln Tyr Tyr Asp Ile Thr Leu Pro Leu Leu Leu
         195                 200                 205

Asp Ser Leu Gln Lys Met Gln Glu Glu Met Ile Lys Ala Leu Lys Gly
 210                 215                 220

Ile Phe Asp Glu Tyr Ser Gln Ile Thr Ser Leu Val Thr Glu Glu Ile
 225                 230                 235                 240

Val Asn Val His Lys Glu Ile Gln Met Ser Val Glu Gln Ile Asp Pro
                 245                 250                 255

Ser Thr Glu Tyr Asn Asn Phe Ile Asp Val His Arg Thr Thr Ala Ala
             260                 265                 270

Lys Glu Gln Glu Ile Glu Phe Asp Thr Ser Leu Leu Glu Glu Asn Glu
         275                 280                 285

Asn Leu Gln Ala Asn Glu Ile Met Trp Asn Asn Leu Thr Ala Glu Ser
 290                 295                 300

Leu Gln Val Met Leu Lys Thr Leu Ala Glu Glu Leu Met Gln Thr Gln
 305                 310                 315                 320

Gln Met Leu Leu Asn Lys Glu Glu Ala Val Leu Glu Leu Glu Lys Arg
                 325                 330                 335

Ile Glu Glu Ser Ser Glu Thr Cys Glu Lys Lys Ser Asp Ile Val Leu
             340                 345                 350

Leu Leu Ser Gln Lys Gln Ala Leu Glu Glu Leu Lys Gln Ser Val Gln
         355                 360                 365

Gln Leu Arg Cys Thr Glu Ala Lys Phe Ser Ala Gln Lys Glu Leu Leu
 370                 375                 380

Glu Gln Lys Val Gln Glu Asn Asp Gly Lys Glu Pro Pro Val Val
 385                 390                 395                 400

Asn Tyr Glu Glu Asp Ala Arg Ser Val Thr Ser Met Glu Arg Lys Glu
                 405                 410                 415

Arg Leu Ser Lys Phe Glu Ser Ile Arg His Ser Ile Ala Gly Ile Ile
             420                 425                 430

Arg Ser Pro Lys Ser Ala Leu Gly Ser Ser Ala Leu Ser Asp Met Ile
         435                 440                 445

Ser Ile Ser Glu Lys Pro Leu Ala Glu Gln Asp Trp Tyr His Gly Ala

```
            450                 455                 460
Ile Pro Arg Ile Glu Ala Gln Glu Leu Leu Lys Lys Gln Gly Asp Phe
465                 470                 475                 480

Leu Val Arg Glu Ser His Gly Lys Pro Gly Glu Tyr Val Leu Ser Val
                485                 490                 495

Tyr Ser Asp Gly Gln Arg His Phe Ile Ile Gln Tyr Val Asp Asn
                500                 505                 510

Met Tyr Arg Phe Glu Gly Thr Gly Phe Ser Asn Ile Pro Gln Leu Ile
            515                 520                 525

Asp His His Tyr Thr Thr Lys Gln Val Ile Thr Lys Ser Gly Val
                530                 535                 540

Val Leu Leu Asn Pro Ile Pro Lys Asp Lys Lys Trp Ile Leu Ser His
545                 550                 555                 560

Glu Asp Val Ile Leu Gly Glu Leu Leu Gly Lys Gly Asn Phe Gly Glu
                565                 570                 575

Val Tyr Lys Gly Thr Leu Lys Asp Lys Thr Ser Val Ala Val Lys Thr
                580                 585                 590

Cys Lys Glu Asp Leu Pro Gln Glu Leu Lys Ile Lys Phe Leu Gln Glu
                595                 600                 605

Ala Lys Ile Leu Lys Gln Tyr Asp His Pro Asn Ile Val Lys Leu Ile
            610                 615                 620

Gly Val Cys Thr Gln Arg Gln Pro Val Tyr Ile Ile Met Glu Leu Val
625                 630                 635                 640

Ser Gly Gly Asp Phe Leu Thr Phe Leu Arg Arg Lys Lys Asp Glu Leu
                645                 650                 655

Lys Leu Lys Gln Leu Val Lys Phe Ser Leu Asp Ala Ala Gly Met
                660                 665                 670

Leu Tyr Leu Glu Ser Lys Asn Cys Ile His Arg Asp Leu Ala Ala Arg
            675                 680                 685

Asn Cys Leu Val Gly Glu Asn Asn Val Leu Lys Ile Ser Asp Phe Gly
            690                 695                 700

Met Ser Arg Gln Glu Asp Gly Gly Val Tyr Ser Ser Ser Gly Leu Lys
705                 710                 715                 720

Gln Ile Pro Ile Lys Trp Thr Ala Pro Glu Ala Leu Asn Tyr Gly Arg
                725                 730                 735

Tyr Ser Ser Glu Ser Asp Val Trp Ser Phe Gly Ile Leu Leu Trp Glu
                740                 745                 750

Thr Phe Ser Leu Gly Val Cys Pro Tyr Pro Gly Met Thr Asn Gln Gln
                755                 760                 765

Ala Arg Glu Gln Val Glu Arg Gly Tyr Arg Met Ser Ala Pro Gln His
            770                 775                 780

Cys Pro Glu Asp Ile Ser Lys Ile Met Met Lys Cys Trp Asp Tyr Lys
785                 790                 795                 800

Pro Glu Asn Arg Pro Lys Phe Ser Glu Leu Gln Lys Glu Leu Thr Ile
                805                 810                 815

Ile Lys Arg Lys Leu Thr
            820

<210> SEQ ID NO 11
<211> LENGTH: 556
<212> TYPE: PRT
<213> ORGANISM: Homo sapiens

<400> SEQUENCE: 11
```

```
Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
            100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
        130                 135                 140

Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
                165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
            195                 200                 205

Glu Asn Ile Leu Leu Asn Glu Asp Met His Ile Gln Ile Thr Asp Phe
        210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
            275                 280                 285

Leu Ile Phe Gln Lys Ile Ile Lys Leu Glu Tyr Asp Phe Pro Glu Lys
        290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
                325                 330                 335

Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
            355                 360                 365

Asp Glu Asp Cys Tyr Gly Asn Tyr Asp Asn Leu Leu Ser Gln Phe Gly
        370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
```

```
                420             425             430
Asp Glu Lys Arg Leu Leu Glu Lys Gln Ala Gly Gly Asn Pro Trp
            435                 440                 445

His Gln Phe Val Glu Asn Asn Leu Ile Leu Lys Met Gly Pro Val Asp
            450                 455                 460

Lys Arg Lys Gly Leu Phe Ala Arg Arg Gln Leu Leu Leu Thr Glu
465                 470                 475                 480

Gly Pro His Leu Tyr Tyr Val Asp Pro Val Asn Lys Val Leu Lys Gly
            485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
            530                 535                 540

Gln Arg Tyr Gln Ser His Pro Asp Ala Ala Val Gln
545                 550                 555

<210> SEQ ID NO 12
<211> LENGTH: 339
<212> TYPE: PRT
<213> ORGANISM: Homo sapiens

<400> SEQUENCE: 12

Met Asp Gln Asn Asn Ser Leu Pro Pro Tyr Ala Gln Gly Leu Ala Ser
1               5                   10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
            35                  40                  45

Leu Ser Ile Leu Glu Glu Gln Gln Arg Gln Gln Gln Gln Gln Gln Gln
50                  55                  60

Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Ala
            85                  90                  95

Val Ala Ala Ala Val Gln Gln Ser Thr Ser Gln Gln Ala Thr Gln
            100                 105                 110

Gly Thr Ser Gly Gln Ala Pro Gln Leu Phe His Ser Gln Thr Leu Thr
            115                 120                 125

Thr Ala Pro Leu Pro Gly Thr Thr Pro Leu Tyr Pro Ser Pro Met Thr
130                 135                 140

Pro Met Thr Pro Ile Thr Pro Ala Thr Pro Ala Ser Glu Ser Ser Gly
145                 150                 155                 160

Ile Val Pro Gln Leu Gln Asn Ile Val Ser Thr Val Asn Leu Gly Cys
            165                 170                 175

Lys Leu Asp Leu Lys Thr Ile Ala Leu Arg Ala Arg Asn Ala Glu Tyr
            180                 185                 190

Asn Pro Lys Arg Phe Ala Ala Val Ile Met Arg Ile Arg Glu Pro Arg
            195                 200                 205

Thr Thr Ala Leu Ile Phe Ser Ser Gly Lys Met Val Cys Thr Gly Ala
210                 215                 220

Lys Ser Glu Glu Gln Ser Arg Leu Ala Ala Arg Lys Tyr Ala Arg Val
225                 230                 235                 240
```

```
Val Gln Lys Leu Gly Phe Pro Ala Lys Phe Leu Asp Phe Lys Ile Gln
            245                 250                 255

Asn Met Val Gly Ser Cys Asp Val Lys Phe Pro Ile Arg Leu Glu Gly
        260                 265                 270

Leu Val Leu Thr His Gln Gln Phe Ser Ser Tyr Glu Pro Glu Leu Phe
        275                 280                 285

Pro Gly Leu Ile Tyr Arg Met Ile Lys Pro Arg Ile Val Leu Leu Ile
        290                 295                 300

Phe Val Ser Gly Lys Val Val Leu Thr Gly Ala Lys Val Arg Ala Glu
305                 310                 315                 320

Ile Tyr Glu Ala Phe Glu Asn Ile Tyr Pro Ile Leu Lys Gly Phe Arg
                325                 330                 335

Lys Thr Thr

<210> SEQ ID NO 13
<211> LENGTH: 114
<212> TYPE: PRT
<213> ORGANISM: Homo sapiens

<400> SEQUENCE: 13

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly Pro
            20                  25                  30

Pro Ile Ala Ser Ala Gly Pro Ala Ala Val Leu Arg Glu Leu Arg
        35                  40                  45

Cys Val Cys Leu Gln Thr Thr Gln Gly Val His Pro Lys Met Ile Ser
    50                  55                  60

Asn Leu Gln Val Phe Ala Ile Gly Pro Gln Cys Ser Lys Val Glu Val
65                  70                  75                  80

Val Ala Ser Leu Lys Asn Gly Lys Glu Ile Cys Leu Asp Pro Glu Ala
                85                  90                  95

Pro Phe Leu Lys Lys Val Ile Gln Lys Ile Leu Asp Gly Gly Asn Lys
            100                 105                 110

Glu Asn

<210> SEQ ID NO 14
<211> LENGTH: 210
<212> TYPE: PRT
<213> ORGANISM: Homo sapiens

<400> SEQUENCE: 14

Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Ser Thr Leu Pro
            20                  25                  30

Pro Phe Leu Ala Pro Glu Trp Asp Leu Leu Ser Pro Arg Val Val Leu
        35                  40                  45

Ser Arg Gly Ala Pro Ala Gly Pro Pro Leu Leu Phe Leu Leu Glu Ala
    50                  55                  60

Gly Ala Phe Arg Glu Ser Ala Gly Ala Pro Ala Asn Arg Ser Arg Arg
65                  70                  75                  80

Gly Val Ser Glu Thr Ala Pro Ala Ser Arg Arg Gly Glu Leu Ala Val
                85                  90                  95

Cys Asp Ala Val Ser Gly Trp Val Thr Asp Arg Arg Thr Ala Val Asp
            100                 105                 110
```

-continued

```
Leu Arg Gly Arg Glu Val Glu Val Leu Gly Glu Val Pro Ala Ala Gly
            115                 120                 125
Gly Ser Pro Leu Arg Gln Tyr Phe Phe Glu Thr Arg Cys Lys Ala Asp
130                 135                 140
Asn Ala Glu Glu Gly Gly Pro Gly Ala Gly Gly Gly Gly Cys Arg Gly
145                 150                 155                 160
Val Asp Arg Arg His Trp Val Ser Glu Cys Lys Ala Lys Gln Ser Tyr
                165                 170                 175
Val Arg Ala Leu Thr Ala Asp Ala Gln Gly Arg Val Gly Trp Arg Trp
            180                 185                 190
Ile Arg Ile Asp Thr Ala Cys Val Cys Thr Leu Leu Ser Arg Thr Gly
        195                 200                 205
Arg Ala
    210

<210> SEQ ID NO 15
<211> LENGTH: 1106
<212> TYPE: PRT
<213> ORGANISM: Homo sapiens

<400> SEQUENCE: 15

Met Arg Leu Pro Gly Ala Met Pro Ala Leu Ala Leu Lys Gly Glu Leu
1               5                   10                  15
Leu Leu Leu Ser Leu Leu Leu Leu Glu Pro Gln Ile Ser Gln Gly
                20                  25                  30
Leu Val Val Thr Pro Pro Gly Pro Glu Leu Val Leu Asn Val Ser Ser
            35                  40                  45
Thr Phe Val Leu Thr Cys Ser Gly Ser Ala Pro Val Val Trp Glu Arg
        50                  55                  60
Met Ser Gln Glu Pro Pro Gln Glu Met Ala Lys Ala Gln Asp Gly Thr
65                  70                  75                  80
Phe Ser Ser Val Leu Thr Leu Thr Asn Leu Thr Gly Leu Asp Thr Gly
                85                  90                  95
Glu Tyr Phe Cys Thr His Asn Asp Ser Arg Gly Leu Glu Thr Asp Glu
            100                 105                 110
Arg Lys Arg Leu Tyr Ile Phe Val Pro Asp Pro Thr Val Gly Phe Leu
        115                 120                 125
Pro Asn Asp Ala Glu Glu Leu Phe Ile Phe Leu Thr Glu Ile Thr Glu
    130                 135                 140
Ile Thr Ile Pro Cys Arg Val Thr Asp Pro Gln Leu Val Val Thr Leu
145                 150                 155                 160
His Glu Lys Lys Gly Asp Val Ala Leu Pro Val Pro Tyr Asp His Gln
                165                 170                 175
Arg Gly Phe Ser Gly Ile Phe Glu Asp Arg Ser Tyr Ile Cys Lys Thr
            180                 185                 190
Thr Ile Gly Asp Arg Glu Val Asp Ser Asp Ala Tyr Tyr Val Tyr Arg
        195                 200                 205
Leu Gln Val Ser Ser Ile Asn Val Ser Val Asn Ala Val Gln Thr Val
    210                 215                 220
Val Arg Gln Gly Glu Asn Ile Thr Leu Met Cys Ile Val Ile Gly Asn
225                 230                 235                 240
Glu Val Val Asn Phe Glu Trp Thr Tyr Pro Arg Lys Glu Ser Gly Arg
                245                 250                 255
Leu Val Glu Pro Val Thr Asp Phe Leu Leu Asp Met Pro Tyr His Ile
```

```
                260                 265                 270
Arg Ser Ile Leu His Ile Pro Ser Ala Glu Leu Glu Asp Ser Gly Thr
        275                 280                 285
Tyr Thr Cys Asn Val Thr Glu Ser Val Asn Asp His Gln Asp Glu Lys
290                 295                 300
Ala Ile Asn Ile Thr Val Val Glu Ser Gly Tyr Val Arg Leu Leu Gly
305                 310                 315                 320
Glu Val Gly Thr Leu Gln Phe Ala Glu Leu His Arg Ser Arg Thr Leu
                325                 330                 335
Gln Val Val Phe Glu Ala Tyr Pro Pro Thr Val Leu Trp Phe Lys
                340                 345                 350
Asp Asn Arg Thr Leu Gly Asp Ser Ser Ala Gly Glu Ile Ala Leu Ser
                355                 360                 365
Thr Arg Asn Val Ser Glu Thr Arg Tyr Val Ser Glu Leu Thr Leu Val
                370                 375                 380
Arg Val Lys Val Ala Glu Ala Gly His Tyr Thr Met Arg Ala Phe His
385                 390                 395                 400
Glu Asp Ala Glu Val Gln Leu Ser Phe Gln Leu Gln Ile Asn Val Pro
                405                 410                 415
Val Arg Val Leu Glu Leu Ser Glu Ser His Pro Asp Ser Gly Glu Gln
                420                 425                 430
Thr Val Arg Cys Arg Gly Arg Gly Met Pro Gln Pro Asn Ile Ile Trp
                435                 440                 445
Ser Ala Cys Arg Asp Leu Lys Arg Cys Pro Arg Glu Leu Pro Pro Thr
450                 455                 460
Leu Leu Gly Asn Ser Ser Glu Glu Ser Gln Leu Glu Thr Asn Val
465                 470                 475                 480
Thr Tyr Trp Glu Glu Gln Glu Phe Glu Val Val Ser Thr Leu Arg
                485                 490                 495
Leu Gln His Val Asp Arg Pro Leu Ser Val Arg Cys Thr Leu Arg Asn
                500                 505                 510
Ala Val Gly Gln Asp Thr Gln Glu Val Ile Val Val Pro His Ser Leu
                515                 520                 525
Pro Phe Lys Val Val Val Ile Ser Ala Ile Leu Ala Leu Val Val Leu
                530                 535                 540
Thr Ile Ile Ser Leu Ile Ile Leu Ile Met Leu Trp Gln Lys Lys Pro
545                 550                 555                 560
Arg Tyr Glu Ile Arg Trp Lys Val Ile Glu Ser Val Ser Ser Asp Gly
                565                 570                 575
His Glu Tyr Ile Tyr Val Asp Pro Met Gln Leu Pro Tyr Asp Ser Thr
                580                 585                 590
Trp Glu Leu Pro Arg Asp Gln Leu Val Leu Gly Arg Thr Leu Gly Ser
                595                 600                 605
Gly Ala Phe Gly Gln Val Val Glu Ala Thr Ala His Gly Leu Ser His
                610                 615                 620
Ser Gln Ala Thr Met Lys Val Ala Val Lys Met Leu Lys Ser Thr Ala
625                 630                 635                 640
Arg Ser Ser Glu Lys Gln Ala Leu Met Ser Glu Leu Lys Ile Met Ser
                645                 650                 655
His Leu Gly Pro His Leu Asn Val Val Asn Leu Leu Gly Ala Cys Thr
                660                 665                 670
Lys Gly Gly Pro Ile Tyr Ile Ile Thr Glu Tyr Cys Arg Tyr Gly Asp
                675                 680                 685
```

-continued

```
Leu Val Asp Tyr Leu His Arg Asn Lys His Thr Phe Leu Gln His His
    690                 695                 700
Ser Asp Lys Arg Arg Pro Ser Ala Glu Leu Tyr Ser Asn Ala Leu
705                 710                 715                 720
Pro Val Gly Leu Pro Leu Pro Ser His Val Ser Leu Thr Gly Glu Ser
                    725                 730                 735
Asp Gly Gly Tyr Met Asp Met Ser Lys Asp Glu Ser Val Asp Tyr Val
                740                 745                 750
Pro Met Leu Asp Met Lys Gly Asp Val Lys Tyr Ala Asp Ile Glu Ser
            755                 760                 765
Ser Asn Tyr Met Ala Pro Tyr Asp Asn Tyr Val Pro Ser Ala Pro Glu
770                 775                 780
Arg Thr Cys Arg Ala Thr Leu Ile Asn Glu Ser Pro Val Leu Ser Tyr
785                 790                 795                 800
Met Asp Leu Val Gly Phe Ser Tyr Gln Val Ala Asn Gly Met Glu Phe
                805                 810                 815
Leu Ala Ser Lys Asn Cys Val His Arg Asp Leu Ala Ala Arg Asn Val
                820                 825                 830
Leu Ile Cys Glu Gly Lys Leu Val Lys Ile Cys Asp Phe Gly Leu Ala
                835                 840                 845
Arg Asp Ile Met Arg Asp Ser Asn Tyr Ile Ser Lys Gly Ser Thr Phe
850                 855                 860
Leu Pro Leu Lys Trp Met Ala Pro Glu Ser Ile Phe Asn Ser Leu Tyr
865                 870                 875                 880
Thr Thr Leu Ser Asp Val Trp Ser Phe Gly Ile Leu Leu Trp Glu Ile
                885                 890                 895
Phe Thr Leu Gly Gly Thr Pro Tyr Pro Glu Leu Pro Met Asn Glu Gln
                900                 905                 910
Phe Tyr Asn Ala Ile Lys Arg Gly Tyr Arg Met Ala Gln Pro Ala His
            915                 920                 925
Ala Ser Asp Glu Ile Tyr Glu Ile Met Gln Lys Cys Trp Glu Glu Lys
            930                 935                 940
Phe Glu Ile Arg Pro Pro Phe Ser Gln Leu Val Leu Leu Leu Glu Arg
945                 950                 955                 960
Leu Leu Gly Glu Gly Tyr Lys Lys Lys Tyr Gln Gln Val Asp Glu Glu
                965                 970                 975
Phe Leu Arg Ser Asp His Pro Ala Ile Leu Arg Ser Gln Ala Arg Leu
            980                 985                 990
Pro Gly Phe His Gly Leu Arg Ser Pro Leu Asp Thr Ser Ser Val Leu
            995                 1000                1005
Tyr Thr Ala Val Gln Pro Asn Glu Gly Asp Asn Asp Tyr Ile Ile
    1010                1015                1020
Pro Leu Pro Asp Pro Lys Pro Glu Val Ala Asp Glu Gly Pro Leu
    1025                1030                1035
Glu Gly Ser Pro Ser Leu Ala Ser Ser Thr Leu Asn Glu Val Asn
    1040                1045                1050
Thr Ser Ser Thr Ile Ser Cys Asp Ser Pro Leu Glu Pro Gln Asp
    1055                1060                1065
Glu Pro Glu Pro Glu Pro Gln Leu Glu Leu Gln Val Glu Pro Glu
    1070                1075                1080
Pro Glu Leu Glu Gln Leu Pro Asp Ser Gly Cys Pro Ala Pro Arg
    1085                1090                1095
```

Ala Glu Ala Glu Asp Ser Phe Leu
    1100            1105

<210> SEQ ID NO 16
<211> LENGTH: 219
<212> TYPE: PRT
<213> ORGANISM: Homo sapiens

<400> SEQUENCE: 16

Met Lys Asp Asn Asp Ile Lys Arg Leu Leu Tyr Thr His Leu Leu Cys
1               5                   10                  15

Ile Phe Ser Ile Ile Leu Ser Val Phe Ile Pro Ser Leu Phe Leu Glu
            20                  25                  30

Asn Phe Ser Ile Leu Glu Thr His Leu Thr Trp Leu Cys Ile Cys Ser
        35                  40                  45

Gly Phe Val Thr Ala Val Asn Leu Val Leu Tyr Leu Val Val Lys Pro
    50                  55                  60

Asn Thr Ser Ser Lys Arg Ser Ser Leu Ser His Lys Val Thr Gly Phe
65                  70                  75                  80

Leu Lys Cys Cys Ile Tyr Phe Leu Met Ser Cys Phe Ser Phe His Val
                85                  90                  95

Ile Phe Val Leu Tyr Gly Ala Pro Leu Ile Glu Leu Ala Leu Glu Thr
            100                 105                 110

Phe Leu Phe Ala Val Ile Leu Ser Thr Phe Thr Thr Val Pro Cys Leu
        115                 120                 125

Cys Leu Leu Gly Pro Asn Leu Lys Ala Trp Leu Arg Val Phe Ser Arg
    130                 135                 140

Asn Gly Val Thr Ser Ile Trp Glu Asn Ser Leu Gln Ile Thr Thr Ile
145                 150                 155                 160

Ser Ser Phe Val Gly Ala Trp Leu Gly Ala Leu Pro Ile Pro Leu Asp
                165                 170                 175

Trp Glu Arg Pro Trp Gln Val Trp Pro Ile Ser Cys Thr Leu Gly Ala
            180                 185                 190

Thr Phe Gly Tyr Val Ala Gly Leu Val Ile Ser Pro Leu Trp Ile Tyr
        195                 200                 205

Trp Asn Arg Lys Gln Leu Thr Tyr Lys Asn Asn
    210                 215

<210> SEQ ID NO 17
<211> LENGTH: 522
<212> TYPE: PRT
<213> ORGANISM: Homo sapiens

<400> SEQUENCE: 17

Met Asp Phe Leu Leu Gly Leu Cys Leu Tyr Trp Leu Leu Arg Arg
1               5                   10                  15

Pro Ser Gly Val Val Leu Cys Leu Leu Gly Ala Cys Phe Gln Met Leu
            20                  25                  30

Pro Ala Ala Pro Ser Gly Cys Pro Gln Leu Cys Arg Cys Glu Gly Arg
        35                  40                  45

Leu Leu Tyr Cys Glu Ala Leu Asn Leu Thr Glu Ala Pro His Asn Leu
    50                  55                  60

Ser Gly Leu Leu Gly Leu Ser Leu Arg Tyr Asn Ser Leu Ser Glu Leu
65                  70                  75                  80

Arg Ala Gly Gln Phe Thr Gly Leu Met Gln Leu Thr Trp Leu Tyr Leu
                85                  90                  95

```
Asp His Asn His Ile Cys Ser Val Gln Gly Asp Ala Phe Gln Lys Leu
            100                 105                 110

Arg Arg Val Lys Glu Leu Thr Leu Ser Ser Asn Gln Ile Thr Gln Leu
        115                 120                 125

Pro Asn Thr Thr Phe Arg Pro Met Pro Asn Leu Arg Ser Val Asp Leu
    130                 135                 140

Ser Tyr Asn Lys Leu Gln Ala Leu Ala Pro Asp Leu Phe His Gly Leu
145                 150                 155                 160

Arg Lys Leu Thr Thr Leu His Met Arg Ala Asn Ala Ile Gln Phe Val
                165                 170                 175

Pro Val Arg Ile Phe Gln Asp Cys Arg Ser Leu Lys Phe Leu Asp Ile
            180                 185                 190

Gly Tyr Asn Gln Leu Lys Ser Leu Ala Arg Asn Ser Phe Ala Gly Leu
        195                 200                 205

Phe Lys Leu Thr Glu Leu His Leu Glu His Asn Asp Leu Val Lys Val
    210                 215                 220

Asn Phe Ala His Phe Pro Arg Leu Ile Ser Leu His Ser Leu Cys Leu
225                 230                 235                 240

Arg Arg Asn Lys Val Ala Ile Val Val Ser Ser Leu Asp Trp Val Trp
                245                 250                 255

Asn Leu Glu Lys Met Asp Leu Ser Gly Asn Glu Ile Glu Tyr Met Glu
            260                 265                 270

Pro His Val Phe Glu Thr Val Pro His Leu Gln Ser Leu Gln Leu Asp
        275                 280                 285

Ser Asn Arg Leu Thr Tyr Ile Glu Pro Arg Ile Leu Asn Ser Trp Lys
    290                 295                 300

Ser Leu Thr Ser Ile Thr Leu Ala Gly Asn Leu Trp Asp Cys Gly Arg
305                 310                 315                 320

Asn Val Cys Ala Leu Ala Ser Trp Leu Asn Asn Phe Gln Gly Arg Tyr
                325                 330                 335

Asp Gly Asn Leu Gln Cys Ala Ser Pro Glu Tyr Ala Gln Gly Glu Asp
            340                 345                 350

Val Leu Asp Ala Val Tyr Ala Phe His Leu Cys Glu Asp Gly Ala Glu
        355                 360                 365

Pro Thr Ser Gly His Leu Leu Ser Ala Val Thr Asn Arg Ser Asp Leu
    370                 375                 380

Gly Pro Pro Ala Ser Ser Ala Thr Thr Leu Ala Asp Gly Gly Glu Gly
385                 390                 395                 400

Gln His Asp Gly Thr Phe Glu Pro Ala Thr Val Ala Leu Pro Gly Gly
                405                 410                 415

Glu His Ala Glu Asn Ala Val Gln Ile His Lys Val Val Thr Gly Thr
            420                 425                 430

Met Ala Leu Ile Phe Ser Phe Leu Ile Val Val Leu Val Leu Tyr Val
        435                 440                 445

Ser Trp Lys Cys Phe Pro Ala Ser Leu Arg Gln Leu Arg Gln Cys Phe
    450                 455                 460

Val Thr Gln Arg Arg Lys Gln Lys Gln Thr Met His Gln Met
465                 470                 475                 480

Ala Ala Met Ser Ala Gln Glu Tyr Tyr Val Asp Tyr Lys Pro Asn His
                485                 490                 495

Ile Glu Gly Ala Leu Val Ile Ile Asn Glu Tyr Gly Ser Cys Thr Cys
            500                 505                 510

His Gln Gln Pro Ala Arg Glu Cys Glu Val
```

-continued

```
                515                 520

<210> SEQ ID NO 18
<211> LENGTH: 282
<212> TYPE: PRT
<213> ORGANISM: Homo sapiens

<400> SEQUENCE: 18

Met Ala Leu Lys Gln Ile Ser Ser Asn Lys Cys Phe Gly Gly Leu Gln
1               5                   10                  15

Lys Val Phe Glu His Asp Ser Val Glu Leu Asn Cys Lys Met Lys Phe
            20                  25                  30

Ala Val Tyr Leu Pro Pro Lys Ala Glu Thr Gly Lys Cys Pro Ala Leu
        35                  40                  45

Tyr Trp Leu Ser Gly Leu Thr Cys Thr Glu Gln Asn Phe Ile Ser Lys
    50                  55                  60

Ser Gly Tyr His Gln Ser Ala Ser Glu His Gly Leu Val Val Ile Ala
65                  70                  75                  80

Pro Asp Thr Ser Pro Arg Gly Cys Asn Ile Lys Gly Glu Asp Glu Ser
                85                  90                  95

Trp Asp Phe Gly Thr Gly Ala Gly Phe Tyr Val Asp Ala Thr Glu Asp
            100                 105                 110

Pro Trp Lys Thr Asn Tyr Arg Met Tyr Ser Tyr Val Thr Glu Glu Leu
        115                 120                 125

Pro Gln Leu Ile Asn Ala Asn Phe Pro Val Asp Pro Gln Arg Met Ser
    130                 135                 140

Ile Phe Gly His Ser Met Gly Gly His Gly Ala Leu Ile Cys Ala Leu
145                 150                 155                 160

Lys Asn Pro Gly Lys Tyr Lys Ser Val Ser Ala Phe Ala Pro Ile Cys
                165                 170                 175

Asn Pro Val Leu Cys Pro Trp Gly Lys Lys Ala Phe Ser Gly Tyr Leu
            180                 185                 190

Gly Thr Asp Gln Ser Lys Trp Lys Ala Tyr Asp Ala Thr His Leu Val
        195                 200                 205

Lys Ser Tyr Pro Gly Ser Gln Leu Asp Ile Leu Ile Asp Gln Gly Lys
    210                 215                 220

Asp Asp Gln Phe Leu Leu Asp Gly Gln Leu Leu Pro Asp Asn Phe Ile
225                 230                 235                 240

Ala Ala Cys Thr Glu Lys Lys Ile Pro Val Val Phe Arg Leu Gln Glu
                245                 250                 255

Gly Tyr Asp His Ser Tyr Tyr Phe Ile Ala Thr Phe Ile Thr Asp His
            260                 265                 270

Ile Arg His His Ala Lys Tyr Leu Asn Ala
        275                 280

<210> SEQ ID NO 19
<211> LENGTH: 810
<212> TYPE: PRT
<213> ORGANISM: Homo sapiens

<400> SEQUENCE: 19

Met Glu His Lys Glu Val Val Leu Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
```

```
                35                  40                  45
Cys Ala Ala Lys Cys Glu Glu Asp Glu Glu Phe Thr Cys Arg Ala Phe
 50                  55                  60

Gln Tyr His Ser Lys Glu Gln Gln Cys Val Ile Met Ala Glu Asn Arg
 65                  70                  75                  80

Lys Ser Ser Ile Ile Ile Arg Met Arg Asp Val Val Leu Phe Glu Lys
                 85                  90                  95

Lys Val Tyr Leu Ser Glu Cys Lys Thr Gly Asn Gly Lys Asn Tyr Arg
                100                 105                 110

Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
        130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
                180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
        210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
                260                 265                 270

Tyr Gln Cys Leu Lys Gly Thr Gly Glu Asn Tyr Arg Gly Asn Val Ala
            275                 280                 285

Val Thr Val Ser Gly His Thr Cys Gln His Trp Ser Ala Gln Thr Pro
        290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460
```

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
            485                 490                 495

Val Thr Gly Thr Pro Cys Gln Asp Trp Ala Ala Gln Glu Pro His Arg
        500                 505                 510

His Ser Ile Phe Thr Pro Glu Thr Asn Pro Arg Ala Gly Leu Glu Lys
            515                 520                 525

Asn Tyr Cys Arg Asn Pro Asp Gly Asp Val Gly Gly Pro Trp Cys Tyr
530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 20
<211> LENGTH: 1437
<212> TYPE: DNA
<213> ORGANISM: Homo sapiens

<400> SEQUENCE: 20
atggccacca tcacctgcac ccgcttcacg gaagagtacc agctcttcga ggaattgggc    60
aagggagcct tctcggtggt gcgaaggtgt gtgaaggtgc tggctggcca ggagtatgct   120

-continued

| | |
|---|---|
| gccaagatca tcaacacaaa gaagctgtca gccagagacc atcagaagct ggagcgtgaa | 180 |
| gcccgcatct gccgcctgct gaagcacccc aacatcgtcc gactacatga cagcatctca | 240 |
| gaggagggac accactacct gatcttcgac ctggtcactg gtggggaact gtttgaagat | 300 |
| atcgtggccc gggagtatta cagtgaggcg gatgccagtc actgtatcca gcagatcctg | 360 |
| gaggctgtgc tgcactgcca ccagatgggg gtggtgcacc gggacctgaa gcctgagaat | 420 |
| ctgttgctgg cctccaagct caagggtgcc gcagtgaagc tggcagactt tggcctggcc | 480 |
| atagaggtgg aggggagca gcaggcatgg tttgggtttg cagggactcc tggatatctc | 540 |
| tccccagaag tgctgcggaa ggacccgtac gggaagcctg tggacctgtg gcttgtggg | 600 |
| gtcatcctgt acatcctgct ggttgggtac cccccgttct gggatgagga ccagcaccgc | 660 |
| ctgtaccagc agatcaaagc cggcgcctat gatttcccat cgccggaatg ggacactgtc | 720 |
| accccggaag ccaaggatct gatcaataag atgctgacca ttaacccatc caaacgcatc | 780 |
| acagctgccg aagcccttaa gcaccccctgg atctcgcacc gctccaccgt ggcatcctgc | 840 |
| atgcacagac aggagaccgt ggactgcctg aagaagttca atgccaggag gaaactgaag | 900 |
| ggagccattc tcaccacgat gctggccacc aggaacttct ccggagggaa gagtggggga | 960 |
| aacaagaaga gcgatggtgt gaaggaatcc tcagagagca ccaacaccac catcgaggat | 1020 |
| gaagacacca aagtgcggaa acaggaaatt ataaaagtga cagagcagct gattgaagcc | 1080 |
| ataagcaatg gagattttga gtcctacacg aagatgtgcg accctggcat gacagccttc | 1140 |
| gaacctgagg ccctggggaa cctggttgag ggcctggact ccatcgatt ctattttgaa | 1200 |
| aacctgtggt cccggaacag caagcccgtg cacaccacca tcctgaatcc ccacatccac | 1260 |
| ctgatgggcg acgagtcagc ctgcatcgcc tacatccgca tcacgcagta cctggacgct | 1320 |
| ggcggcatcc cacgcaccgc ccagtcggag gagacccgtg tctggcaccg ccgggatggc | 1380 |
| aaatggcaga tcgtccactt ccacagatct ggggcgccct ccgtcctgcc ccactga | 1437 |

<210> SEQ ID NO 21
<211> LENGTH: 2001
<212> TYPE: DNA
<213> ORGANISM: Homo sapiens

<400> SEQUENCE: 21

| | |
|---|---|
| atggccacca cggtgacctg cacccgcttc accgacgagt accagctcta cgaggatatt | 60 |
| ggcaagggg ctttctctgt ggtccgacgc tgtgtcaagc tctgcaccgg ccatgagtat | 120 |
| gcagccaaga tcatcaacac caagaagctg tcagccagag atcaccagaa gctggagaga | 180 |
| gaggctcgga tctgccgcct tctgaagcat tccaacatcg tgcgtctcca cgacagcatc | 240 |
| tccgaggagg gcttccacta cctggtcttc gatctggtca ctggtgggga gctctttgaa | 300 |
| gacattgtgg cgagagagta ctacagcgag gctgatgcca gtcactgtat ccagcagatc | 360 |
| ctggaggccg ttctccattg tcaccaaatg ggggtcgtcc acagagacct caagccggag | 420 |
| aacctgcttc tggccagcaa gtgcaaaggg ctgcagtgaa gctggcagac ttcggcctta | 480 |
| gctatcgagg tgcaggggga ccagcaggca tggtttggtt cgctggcac accaggctac | 540 |
| ctgtcccctg aggtccttcg caaagaggcg tatggcaagc tgtggacat ctgggcatgt | 600 |
| ggggtgatcc tgtacatcct gctcgtgggc tacccaccct tctgggacga ggaccagcac | 660 |
| aagctgtacc agcagatcaa ggctggtgcc tatgacttcc cgtcccctga gtgggacacc | 720 |
| gtcactccta agccaaaaaa cctcatcaac cagatgctga ccatcaaccc tgccaagcgc | 780 |
| atcacagccc atgaggccct gaagcacccg tgggtctgcc aacgctccac ggtagcatcc | 840 |

```
atgatgcaca gacaggagac tgtggagtgt ctgaaaaagt tcaatgccag gagaaagctc      900
aagggagcca tcctcaccac catgctggcc acacggaatt tctcagtggg cagacagacc      960
accgctccgg ccacaatgtc caccgcggcc tccggcacca ccatgggact ggtggaacaa     1020
gccaagagtt tactcaacaa gaaagcagat ggagtcaagc cccagacgaa tagcaccaaa     1080
aacagtgcag ccgccaccag ccccaaaggg acgcttcctc ctgccgccct ggagcctcaa     1140
accaccgtca tccataaccc agtggacggg attaaggagt cttctgacag tgccaatacc     1200
accatagagg atgaagacgc taaagccccc agggtccccg acatcctgag ctcagtgagg     1260
aggggctcgg gagccccaga agccgagggg cccctgccct gcccatctcc ggctcccttt     1320
agccccctgc cagccccatc ccccaggatc tctgacatcc tgaactctgt gagaaggggt     1380
tcaggaaccc cagaagccga gggccccctc tcagcggggc cccgccctg cctgtctccg      1440 gctctcctag gccccctgtc ctccccgtcc ccaggatct ctgacatcct gaactctgtg      1500
aggaggggct cagggacccc agaagccgag ggccctcgc cagtggggcc cccgccctgc      1560
ccatctccga ctatccctgg ccccctgccc accccatccc ggaagcagga gatcattaag     1620
accacggagc agctcatcga ggccgtcaac aacggtgact ttgaggccta cgcgaaaatc     1680
tgtgacccag gctgacctc gtttgagcct gaagcactgg gcaacctggt tgaagggatg      1740
gacttccaca gattctactt cgagaacctg ctggccaaga acagcaagcc gatccacacg     1800
accatcctga cccacacgt gcacgtcatt ggagaggatg ccgcctgcat cgcttacatc      1860
cggctcacgc agtacattga cgggcagggc cggccccgca ccagccagtc tgaggagacc     1920
cgcgtgtggc accgccgcga cggcaagtgg cagaacgtgc acttccactg ctcgggcgcg     1980
cctgtggccc cgctgcagtg a                                              2001
```

<210> SEQ ID NO 22
<211> LENGTH: 1500
<212> TYPE: DNA
<213> ORGANISM: Homo sapiens

<400> SEQUENCE: 22

```
atggcttcga ccacaacctg caccaggttc acggacgagt atcagctttt cgaggagctt       60 ggaaagggg cattctcagt ggtgagaaga tgtatgaaaa ttcctactgg acaagaatat      120
gctgccaaaa ttatcaacac caaaaagctt tctgctaggg atcatcagaa actagaaaga      180
gaagctagaa tctgccgtct tttgaagcac cctaatattg tgcgacttca tgatagcata      240
tcagaagagg gctttcacta cttggtgttt gatttagtta ctggaggtga actgtttgaa      300
gacatagtgg caagagaata ctacagtgaa gctgatgcca gtcattgtat acagcagatt     360
ctagaaagtg ttaatcattg tcacctaaat ggcatagttc acagggacct gaagcctgag      420
aatttgcttt tagctagcaa atccaaggga gcagctgtga aattggcaga ctttggctta      480
gccatagaag ttcaaggga ccagcaggcg tggtttggtt ttgctggcac acctggatat      540
ctttctccag aagttttacg taaagatcct tatggaaagc cagtggatat gtgggcatgt     600
ggtgtcattc tctatattct acttgtgggg tatccaccct ctggatgaa agaccaacac      660 agactctatc agcagatcaa ggctggagct tatgattttc catcaccaga atgggacacg      720
gtgactcctg aagccaaaga cctcatcaat aaaatgctta ctatcaaccc tgccaaacgc     780
atcacagcct cagaggcact gaagcaccca tggatctgtc aacgttctac tgttgcttcc     840
atgatgcaca gacaggagac tgtagactgc ttgaagaaat ttaatgctag aagaaaacta      900
```

| | |
|---|---|
| aagggtgcca tcttgacaac tatgctggct acaaggaatt tctcagcagc caagagtttg | 960 |
| ttgaagaaac cagatggagt aaaggagtca actgagagtt caaatacaac aattgaggat | 1020 |
| gaagatgtga agcacgaaag caagagatt atcaaagtca ctgaacaact gatcgaagct | 1080 |
| atcaacaatg gggactttga agcctacaca aaaatctgtg acccaggcct tactgctttt | 1140 |
| gaacctgaag ctttgggtaa tttagtggaa gggatggatt ttcaccgatt ctactttgaa | 1200 |
| aatgctttgt ccaaaagcaa taaaccaatc cacactatta ttctaaaccc tcatgtacat | 1260 |
| ctggtagggg atgatgccgc ctgcatagca tatattaggc tcacacagta catggatggc | 1320 |
| agtggaatgc caaagacaat gcagtcagaa gagactcgtg tgtggcaccg ccgggatgga | 1380 |
| aagtggcaga atgttcattt tcatcgctcg gggtcaccaa cagtacccat caagccaccc | 1440 |
| tgtattccaa atgggaaaga aaacttctca ggaggcacct ctttgtggca aacatctaa | 1500 |

<210> SEQ ID NO 23
<211> LENGTH: 2961
<212> TYPE: DNA
<213> ORGANISM: Homo sapiens

<400> SEQUENCE: 23

| | |
|---|---|
| atgcccggcg tggcccgcct gccgctgctg ctcgggctgc tgctgctccc cgtcccggc | 60 |
| cggccgctgg acttggccga ctacacctat gacctggcgg aggaggacga ctcggagccc | 120 |
| ctcaactaca agaccccctg caaggcggct gccttcttg gggacattgc cctggacgaa | 180 |
| gaggacctga ggccttcca ggtacagcag gctgtggatc tcagacggca cacagctcgt | 240 |
| aagtcctcca tcaaagctgc agttccagga aacacttcta cccccagctg ccagagcacc | 300 |
| aacgggcagc tcagaggggg agcctgtggg agatggagag gtagatcccg tagccggcgg | 360 |
| gcggcgacgt cccgaccaga gcgtgtgtgg cccgatgggg tcatcccctt tgtcattggg | 420 |
| ggaaacttca ctggtagcca gagggcagtc ttccggcagg ccatgaggca ctgggagaag | 480 |
| cacacctgtg tcaccttcct ggagcgcact gacgaggaca gctatattgt gttcaccat | 540 |
| cgaccttgcg ggtgctgctc ctacgtgggt cgccgcggcg ggggccccca ggccatctcc | 600 |
| atcggcaaga actgtgacaa gttcggcatt gtggtccacg agctgggcca cgtcgtcggc | 660 |
| ttctggcacg aacacactcg gccagaccgg gaccgccacg tttccatcgt tcgtgagaac | 720 |
| atccagccag gcaggagta taacttcctg aagatggagc tcaggaggt ggagtccctg | 780 |
| ggggagacct atgacttcga cagcatcatg cattacgctc ggaacacatt ctccaggggc | 840 |
| atcttcctgg ataccattgt ccccaagtat gaggtgaacg gggtgaaacc tcccattggc | 900 |
| caaaggacac ggctcagcaa gggggacatt gcccaagccc gcaagcttta caagtgccca | 960 |
| gcctgtggag agaccctgca agacagcaca ggcaacttct cctcccctga ataccccaat | 1020 |
| ggctactctg ctcacatgca ctgcgtgtgg cgcatctctg tcacacccgg ggagaagatc | 1080 |
| atcctgaact tcacgtccct ggacctgtac cgcagccgcc tgtgctggta cgactatgtg | 1140 |
| gaggtccgag atgcttctg aggaaggcg cccctccgag gccgcttctg cgggtccaaa | 1200 |
| ctccctgagc ctatcgtctc cactgacagc cgcctctggg ttgaattccg cagcagcagc | 1260 |
| aattgggttg gaaagggctt cttttgcagtc tacgaagcca tctgcgggg tgatgtgaaa | 1320 |
| aaggactatg ccacattca atcgcccaac tacccagacg attaccggcc cagcaaagtc | 1380 |
| tgcatctggg gatccaggt gtctgaggg ttccacgtgg gcctcacatt ccagtccttt | 1440 |
| gagattgagc gccacgacag ctgtgcctac gactatctgg aggtgcgcga cgggcacagt | 1500 |
| gagagcagca ccctcatcgg gcgctactgt ggctatgaga agcctgatga catcaagagc | 1560 |

```
acgtccagcc gcctctggct caagttcgtc tctgacgggt ccattaacaa agcgggcttt      1620
gccgtcaact ttttcaaaga ggtggacgag tgctctcggc ccaaccgcgg gggctgtgag      1680
cagcggtgcc tcaacaccct gggcagctac aagtgcagct gtgaccccgg gtacgagctg      1740
gccccagaca agcgccgctg tgaggctgct tgtggcggat tcctcaccaa gctcaacggc      1800
tccatcacca gcccgggctg gcccaaggag tacccccca acaagaactg catctggcag       1860
ctggtggccc ccacccagta ccgcatctcc ctgcagtttg acttctttga cacagagggc      1920
aatgatgtgt gcaagtacga cttcgtggag gtgcgcagtg gactcacagc tgactccaag      1980
ctgcatggca agttctgtgg ttctgagaag cccgaggtca tcacctccca gtacaacaac      2040
atgcgcgtgg agttcaagtc cgacaacacc gtgtccaaaa agggcttcaa ggcccacttc      2100
ttctcagaca aggacgagtg ctccaaggat aacggcggct gccagcagga ctgcgtcaac      2160
acgttcggca gttatgagtg ccaatgccgc agtggcttcg tcctccatga caacaagcac      2220
gactgcaaag aagccggctg tgaccacaag gtgacatcca ccagtggtac catcaccagc      2280
cccaactggc ctgacaagta tcccagcaag aaggagtgca cgtgggccat ctccagcacc      2340
cccgggcacc gggtcaagct gaccttcatg gagatggaca tcgagtccca gcctgagtgt      2400
gcctacgacc acctagaggt gttcgacggg cgagacgcca aggcccccgt cctcggccgc      2460
ttctgtggga gcaagaagcc cgagcccgtc tggccacag gcagccgcat gttcctgcgc      2520
ttctactcag ataactcggt ccagcgaaag ggcttccagg cctcccacgc cacagagtgc      2580 ggggccagg tacgggcaga cgtgaagacc aaggaccttt actcccacgc ccagtttggc      2640
gacaacaact accctggggg tgtggactgt gagtgggtca ttgtggccga ggaaggctac      2700
ggcgtggagc tcgtgttcca gacctttgag gtggaggagg agaccgactg cggctatgac      2760
tacatggagc tcttcgacgg ctacgacagc acagccccca ggctggggcg ctactgtggc      2820
tcagggcctc ctgaggaggt gtactcggcg ggagattctg tcctggtgaa gttccactcg      2880
gatgacacca tcaccaaaaa aggtttccac ctgcgataca ccagcaccaa gttccaggac      2940
acactccaca gcaggaagtg a                                                2961
```

<210> SEQ ID NO 24
<211> LENGTH: 1165
<212> TYPE: DNA
<213> ORGANISM: Homo sapiens

<400> SEQUENCE: 24

```
aacaggaagt cctccataat cattaggatg agagatgtag ttttatttga aaagaaagtg        60
tatctctcag agtgcaagac tgggaatgga aagaactaca gagggacgat gtccaaaaca       120
aaaaatggca tcacctgtca aaaatggagt tccacttctc cccacagacc tagattctca       180
cctgctacac accccctcaga gggactggag gagaactact gcaggaatcc agacaacgat       240 ccgcagggc cctggtgcta ctactactgat ccagaaaaga gatatgacta ctgcgacatt       300
cttgagtgtg aagaggaatg tatgcattgc agtggagaaa actatgacgg caaaatttcc       360
aagaccatgt ctggactgga atgccaggcc tgggactctc agagcccaca cgctcatgga      420
tacattcctt ccaaatttcc aaacaagaac ctgaagaaga attactgtcg taaccccgat       480
agggagctgc ggccttggtg tttcaccacc gaccccaaca gcgctgggga ctttgtgac       540 atccccgct gcaacacacc tccaccatct tctggtccca cctaccagtg tctgaaggga      600
acaggtgaaa actatcgcgg gaatgtggct gttaccgtgt ccgggcacac ctgtcagcac      660
```

| | |
|---|---|
| tggagtgcac agacccctca cacacataac aggacaccag aaaacttccc ctgcaaaaat | 720 |
| ttggatgaaa actactgccg caatcctgac ggaaaaaggg ccccatggtg ccatacaacc | 780 |
| aacagccaag tgcggtggga gtactgtaag ataccgtcct gtgactcctc cccagtatcc | 840 |
| acggaacaat tggctcccac agcaccacct gagctaaccc ctgtggtcca ggactgctac | 900 |
| catggtgatg acagagcta ccgaggcaca tcctccacca ccaccacagg aaagaagtgt | 960 |
| cagtcttggt catctatgac accacaccgg caccagaaga ccccagaaaa ctacccaaat | 1020 |
| gctggcctga caatgaacta ctgcaggaat ccagatgccg ataaaggccc ctggtgtttt | 1080 |
| accacagacc ccagcgtcag gtgggagtac tgcaacctga aaaatgctc aggaacagaa | 1140 |
| gcgagtgttg tagcacctcc gcctg | 1165 |

<210> SEQ ID NO 25
<211> LENGTH: 2433
<212> TYPE: DNA
<213> ORGANISM: Homo sapiens

<400> SEQUENCE: 25

| | |
|---|---|
| atggaacata aggaagtggt tcttctactt cttttatttc tgaaatcagg tcaaggagag | 60 |
| cctctggatg actatgtgaa tacccagggg gcttcactgt tcagtgtcac taagaagcag | 120 |
| ctggagcag gaagtataga agaatgtgca gcaaaatgtg aggaggacga agaattcacc | 180 |
| tgcagggcat tccaatatca cagtaaagag caacaatgtg tgataatggc tgaaaacagg | 240 |
| aagtcctcca taatcattag gatgagagat gtagttttat ttgaaaagaa agtgtatctc | 300 |
| tcagagtgca gactgggaa tggaaagaac tacagaggga cgatgtccaa aacaaaaaat | 360 |
| ggcatcacct gtcaaaaatg gagttccact ctctccccaca gacctagatt ctcacctgct | 420 |
| acacaccct cagagggact ggaggagaac tactgcagga atccagacaa cgatccgcag | 480 |
| gggccctggt gctatactac tgatccagaa aagagatatg actactgcga cattcttgag | 540 |
| tgtgaagagg aatgtatgca ttgcagtgga aaaactatg acggcaaaat ttccaagacc | 600 |
| atgtctggac tggaatgcca ggcctgggac tctcagagcc cacacgctca tggatacatt | 660 |
| ccttccaaat ttccaaacaa gaacctgaag aagaattact gtcgtaaccc cgataggag | 720 |
| ctgcggcctt ggtgtttcac caccgacccc aacaagcgct gggaactttg tgacatcccc | 780 |
| cgctgcacaa cacctccacc atcttctggt cccacctacc agtgtctgaa gggaacaggt | 840 |
| gaaaactatc gcgggaatgt ggctgttacc gtgtccgggc acacctgtca gcactggagt | 900 |
| gcacagaccc ctcacacaca taacaggaca ccagaaaact ccccctgcaa aaatttggat | 960 |
| gaaaactact gccgcaatcc tgacggaaaa agggcccat ggtgccatac aaccaacagc | 1020 |
| caagtgcggt gggagtactg taagataccg tcctgtgact cctccccagt atccacggaa | 1080 |
| caattggctc ccacagcacc acctgagcta accctgtgg tccaggactg ctaccatggt | 1140 |
| gatggacaga gctaccgagg cacatcctcc accaccacca caggaaagaa gtgtcagtct | 1200 |
| tggtcatcta tgacaccaca ccggcaccag aagacccag aaaactaccc aaatgctggc | 1260 |
| ctgacaatga actactgcag gaatccagat gccgataaag cccctggtg ttttaccaca | 1320 |
| gaccccagcg tcaggtggga gtactgcaac ctgaaaaaat gctcaggaac agaagcgagt | 1380 |
| gttgtagcac ctccgcctgt tgtcctgctt ccagatgtag agactccttc gaagaagac | 1440 |
| tgtatgtttg ggaatgggaa aggataccga ggcaagaggg cgaccactgt tactgggacg | 1500 |
| ccatgccagg actgggctgc ccaggagccc catagacaca gcattttcac tccagagaca | 1560 |
| aatccacggg cgggtctgga aaaaaattac tgccgtaacc ctgatggtga tgtaggtggt | 1620 |

```
ccctggtgct acacgacaaa tccaagaaaa ctttacgact actgtgatgt ccctcagtgt    1680
gcggcccctt catttgattg tgggaagcct caagtggagc cgaagaaatg tcctggaagg    1740
gttgtagggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat taa                                 2433
```